(12) United States Patent
Durden et al.

(10) Patent No.: US 10,308,662 B2
(45) Date of Patent: *Jun. 4, 2019

(54) THIENOPYRANONES AS KINASE AND EPIGENETIC INHIBITORS

(71) Applicant: SignalRx Pharmaceuticals, Inc., San Diego, CA (US)

(72) Inventors: Donald L. Durden, San Diego, CA (US); Guillermo A. Morales, Oro Valley, AZ (US); Joseph R. Garlich, Volcano, HI (US)

(73) Assignee: Signal Rx Pharmaceuticals., Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/672,627

(22) Filed: Aug. 9, 2017

(65) Prior Publication Data
US 2017/0334925 A1    Nov. 23, 2017

Related U.S. Application Data

(62) Division of application No. 15/297,293, filed on Oct. 19, 2016, now abandoned, which is a division of application No. 14/702,822, filed on May 4, 2015, now Pat. No. 9,505,780.

(60) Provisional application No. 61/988,352, filed on May 5, 2014.

(51) Int. Cl.
*C07D 495/04* (2006.01)
*A61K 45/06* (2006.01)
*A61K 31/5377* (2006.01)
*A61K 31/541* (2006.01)
*A61K 31/538* (2006.01)

(52) U.S. Cl.
CPC .......... *C07D 495/04* (2013.01); *A61K 31/538* (2013.01); *A61K 31/5377* (2013.01); *A61K 31/541* (2013.01); *A61K 45/06* (2013.01)

(58) Field of Classification Search
CPC .................... C07D 495/04; A61K 31/5377
See application file for complete search history.

(56) References Cited

U.S. PATENT DOCUMENTS

| | | | |
|---|---|---|---|
| 8,557,807 B2 | 10/2013 | Morales et al. | |
| 9,505,780 B2 * | 11/2016 | Durden | C07D 495/04 |
| 9,550,790 B2 * | 1/2017 | Morales | A61K 31/381 |

OTHER PUBLICATIONS

U.S. Appl. No. 14/041,279, filed Mar. 13, 2014, G. Morales et al.
U.S. Appl. No. 14/702,816, filed Nov. 5, 2015, G. Morales et al.
U.S. Appl. No. 14/702,822, filed Dec. 3, 2015, D. Durden et al.

* cited by examiner

*Primary Examiner* — Golam M Shameem
(74) *Attorney, Agent, or Firm* — Thomas D. Webster; TDW Patents & Consulting

(57) ABSTRACT

The invention relates to methods of treating diseases including but not limited to, cancer, non-cancer proliferative disease, sepsis, autoimmune disease, viral infaction, atheroscleosis, Type 1 or 2 diabetes, obesity, inflammatory disease, or Myc-depenent disorder including by modulating biological processes by the inhibition of PI3 kinase and/or bromodomain protein binding to substrates comprising the administration of a compound(s) of Formula I-IX (or pharmaceutically acceptable salts thereof) as defined herein.

11 Claims, 11 Drawing Sheets

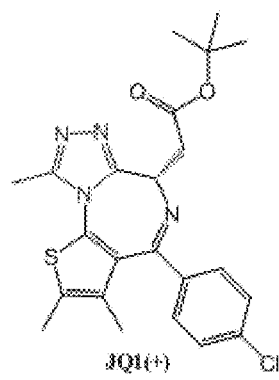
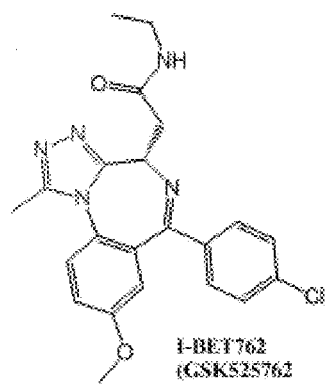
Fig. 1A
Fig. 1B
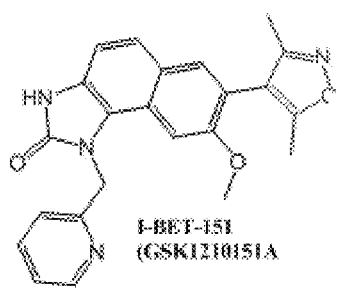
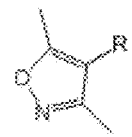
Fig. 1C
Fig. 1D

THIENOPYRANONES AS KINASE AND EPIGENETIC INHIBITORS

CROSS REFERENCE TO RELATED APPLICATIONS

This application is a divisional of application Ser. No. 15/297,293, filed Oct. 19, 2016, which is a divisional of application Ser. No. 14/702,822, filed May 4, 2015, which claims the benefit of U.S. Provisional Application No. 61/988,352, filed May 5, 2014, herein incorporated by reference.

FIELD OF THE INVENTION

The present invention relates to thienopyranone compounds and methods of using the compounds as inhibitors of kinases or bromodomain proteins or both including for treating diseases in mammals

BACKGROUND

Protein kinases play an important role in regulating most cellular functions including proliferation, cell cycle, cell metabolism, survival/apoptosis, DNA damage repair, cell motility, and response to the microenvironment. Not surprisingly kinases have been identified as oncogenes. For example, kinases such as c-Src, c-Abl, mitogen activated protein (MAP) kinase, phosphotidylinositol-3-kinase (PI3-K, PI3K, PI-3 kinase), AKT (also known as PKB), and the epidermal growth factor (EGF) receptor are commonly activated in cancer cells and are known to contribute to tumorigenesis. Many of these mutations occur in the same signaling pathway. For example, HER-kinase family members (HER1 [EGFR], HER3, and HER4) transmit signals through MAP kinase and PI-3 kinase to promote cell proliferation.

PI-3 kinases are a large family of lipid kinases comprising roughly 16 members divided into 3 classes based on sequence homology and the particular product formed by enzyme catalysis. The class I PI-3 kinases are composed of 2 subunits: a 110 kd catalytic subunit and an 85 kd regulatory subunit. Class I PI-3 kinases are involved in important signal transduction events downstream of cytokines, integrins, growth factors and immunoreceptors, and control of this pathway may lead to important therapeutic effects. Inhibition of class I PI-3 kinase induces apoptosis, blocks tumor induced angiogenesis in vivo, and increases radiosensitivity in certain tumors.

Molecular and genetic studies have demonstrated a strong correlation between the PI-3 kinase pathway (also known as PI3K-AKT pathway) and a variety of diseases in humans such as inflammation, autoimmune conditions, and cancers (P. Workman et al., Nat. Biotechnol. 2006, 24, 794-796). The PI-3 kinase pathway controls a number of cellular functions including cell growth, metabolism, differentiation, and apoptosis. Many types of cancer are thought to arise in response to abnormalities in signal transduction pathways of which the PI-3 kinase pathway is a major example.

The PI-3 kinase pathway comprises a number of enzymes including PI-3 kinase, PTEN (Phosphatase and Tensin homolog deleted on chromosome 10), and AKT (a serine/threonine kinase) all of which are involved in producing and maintaining intracellular levels of second messenger molecule PtdIns(3,4,5)P3 (PIP3). Homeostasis in the levels of this important second messenger is maintained by the interaction between PI-3 kinase and PTEN. When either PI-3 kinase or PTEN are mutated and/or reduced in activity PIP3 levels are perturbed which may act as a trigger in the development of cancer. Indeed, both PI-3 kinase and PTEN have been found to be mutated in multiple cancers including glioblastoma, ovarian, breast, endometrial, hepatic, melanoma, gut, lung, renal cell, thyroid and lymphoid cancer. Multiple studies have now shown that p110α, which is a Class IA isoform of the regulatory subunit of PI-3 kinase, is frequently over-expressed and mutated in many cancers including gliomas, colon, brain, breast, lung, prostate, gynecological and other tumor types (Y. Samuels et al., Science 2004, 304, 554). Thus, a rational approach to treating cancer relates to developing drugs that act on kinases including those of the PI-3 kinase pathway.

Another putative mechanism for cancer involving kinase dependency is through loss of a negative regulator. Perhaps the best example of this comes from tumors with mutations in the PTEN tumor suppressor gene. This gene, which is mutated or deleted in a number of different cancers, encodes a lipid phosphatase that regulates signaling through the PI-3 kinase pathway. Specifically, PTEN dephosphorylates PIP3, the product of PI-3 kinase (for review see L. C. Cantley et al., Proc. Natl. Acad. Sci. 1999, 96, 4240-4245). As a consequence of PTEN loss and the resultant increase in PIP3 levels, signal propagation through downstream kinases such as AKT is constitutively elevated. Preclinical studies suggest that this indirect mode of constitutive kinase activation in tumor cells (i.e., through loss of the PTEN suppressor gene), creates a kinase dependency analogous to that seen in tumors with direct, activating mutations in the kinase itself.

Genetic and biochemical evidence from several model systems has established that constitutive levels of AKT can regulate TOR (mTOR in mammalian systems) through phosphorylation of the tuberous sclerosis complex (K. Inoki et al., Nat. Cell Biol. 2002, 4, 648-657). Hence, tumors with loss-of-function mutations in PTEN exhibit constitutive activation of AKT, as well as other downstream kinases such as mTOR. Many such tumors in murine models have been shown to be sensitive to mTOR inhibitors (M. S. Neshat et al., Proc. Natl. Acad. Sci. 2001, 98, 10314-10319).

At the cytocellular level, the induction and/or progression of cancer appears to involve a sub-population of cells within a tumor known as cancer stem cells. Within a population of cancer cells there exist a small number of cells that are capable of fully re-establishing a tumor. These cells are called cancer stem cells and are thought to be responsible for the inability to cure cancer with current drugs. These cells are characterized as having enhanced drug efflux properties, lacking in cell cycle progression (quiescent), and possessing resistance to anoikis (apoptosis upon experiencing loss of anchorage). Cancer stem cells have been described in the literature in solid tumor types, for example, see the review and references incorporated therein by J. E. Visvader et al., Nat. Rev. Cancer 2008, 8, 755-768: "Cancer Stem Cells in Solid Tumors: accumulating evidence and unresolved questions". Non-solid tumor cancer stem cells have also been reviewed recently, for example, see the review and references incorporated therein by J. E. Dick et al., Blood 2008, 112, 4793-4807: "Stem cell concepts renew cancer research". To date the only documented clinical example of an approved cancer therapeutic drug that decreases cancer stem cells is Lapatinib which was shown to decrease the number of breast cancer stem cells in biopsies of women with breast tumors possessing high levels of HER2 protein (decreased from 11% down to 5% of cells) [C. Schmidt et al., *J. Natl. Cancer I.* 2008, 100, 694-695: "Lapatinib Study Supports Cancer Stem Cell Hypothesis, Encourages Industry Research"].

While therapeutic agents that act as modulators of signaling pathways are of clear therapeutic interest as agonists or antagonists of particular enzymes within a signaling pathway, e.g. inhibitors of PI-3 kinase, recent evidence indicates that independent mechanisms exist for providing therapeutic efficacy including, for example, oxidative stress. The generation of oxidative stress in cancer cells is a recent but well described cancer treatment approach. Examples of agents that induce such stress include clinically evaluated compounds such as buthionine sulfoximine/melphalan, imexon, arsenic trioxide, and motexafin gadolinium, and the like [see for example the review and references incorporated therein by R. H. Engel et al., *Front. Biosci* 2006, 11, 300-312: "Oxidative Stress and Apoptosis: a new treatment paradigm in cancer"]. Cromenones such as LY294002 and the related analog LY3035111 have been reported to induce apoptosis in tumor cells due to intracellular hydrogen peroxide production independent of their PI3 kinase inhibition activity [T. W. Poh et al., *Cancer Res.* 2005, 65, 6264-6274: "LY294002 and LY303511 Sensitize Tumor Cells to Drug-Induced Apoptosis via Intracellular Hydrogen Peroxide Production Independent of the Phosphoinositide 3-Kinase-Akt Pathway"]. This ability to induce oxidative stress in cancer cells is a positive attribute for an anticancer agent. Oxidative stress induction has also been demonstrated to enhance sensitivity of prostate cancer cells to nonapoptotic concentrations of the chemotherapeutic agent vincristine.

LY294002 (2-(4-morpholinyl)-8-phenyl-4H-1-benzopyran-4-one) is a potent, non-selective inhibitor of PI-3 kinases with an IC50 of 1.4 µM (C. J. Vlahos et al., *J. Biol. Chem.* 1994, 269, 5241-5248). While LY294002 is an effective inhibitor of PI-3 kinase it has several undesirable attributes for clinical use including lack of aqueous solubility, poor pharmacokinetics, unacceptable toxicity, lack of tissue specificity, rapid metabolism in animals, and a synthetic route that involves the use of carbon disulfide, a highly toxic compound. As such, LY294002 has never been developed for clinical use.

A growing list of diseases including cancer can arise by epigenetically-induced changes in gene expression and cellular phenotype by mechanisms other than changes in DNA nucleotide sequence. Epigenetic effects can be controlled by three types of proteins: the writers (i.e., DNA methyltransferase which adds methyl groups to DNA), the erasers (i.e., histone deacetylase, HDAC, which removes acetyl groups from histones), and the readers (i.e., BET bromodomain proteins such as BRD2, BRD3, BRD4 and BRDT). Bromodomain proteins serve as "readers" for the chromatin to recruit regulatory enzymes such as the writers and erasers leading to regulation of gene expression. Inhibitors of bromodomain proteins are potentially useful in the treatment of diseases including obesity, inflammation, and cancer (A. C. Belkina et al., *Nat. Rev. Cancer* 2012, 12, 465-477).

BET inhibitors act as acetylated lysine mimetics that disrupt the binding interaction of BET proteins with acetylated lysine residues on histones (D. S. Hewings et al., *J. Med. Chem.* 2012, 55, 9393-9413). This leads to suppression of transcription of some key genes involved in cancer including c-MYC, MYCN, BCL-2, and some NF-kB-dependent genes (J. E. Delmore et al., *Cell* 2011, 146, 904-917) (A. Puissant et al., *Cancer Discov.* 2013, 3, 308-323). Most B-cell malignancies are associated with the activation of the c-MYC gene which is partially controlled by the PI-3 kinase-AKT-GSK3beta signaling axis (J. E. Delmore et al., *Cell* 2011, 146, 904-917). MYC (encompassing c-MYC and MYCN) is an oncoprotein that has been difficult to inhibit using small molecule approaches (E. V. Prochownik et al., *Genes Cancer* 2010, 1, 650-659). Recently it has been shown that BET inhibition prevents the transcription of MYCN, (A. Puissant et al., *Cancer Discov.* 2013, 3, 308-323), and blocking PI-3K enhances MYC degradation (L. Chesler et al., *Cancer Res.* 2006, 66, 8139-8146). Therefore, a single molecule that inhibits both PI-3K and bromodomain proteins would provide a novel and more effective way to inhibit MYC activity. FIG. 1 shows the structures of several reported BET inhibitors some of which contain the 3,5-dimethylisoxazole chemotype as the acetyl-lysine mimetic moiety (D. S. Hewings, *J. Med. Chem.* 2011, 54, 6761-6770) (D. S. Hewings et al., *J. Med. Chem.* 2012, 55, 9393-9413) (D. S. Hewings et al., *J. Med. Chem.* 2013, 56, 3217-3227).

Several recent reviews cover the inception and status of the bromodomain inhibitor field including D. Gallenkamp et al., *ChemMedChem* 2014, 9, 438-464 and S. Muller et al., *Med. Chem. Commun.* 2014, 5, 288-296.

The need for better treatments for cancer and other diseases has lead to combination therapies using multiple anticancer agents, or alternatively multitargeting agents in which a single drug blocks more than one target (see D. Melisi et al., *Curr. Opin. Pharm.*, 2013, 13, 536-542).

Recently, it has been shown that some kinase inhibitors also inhibit bromodomain proteins. For example, PI3 kinase inhibitor LY294002 was found to modestly inhibit BET bromodomains (A. Dittmann et al., *ACS Chem. Biol.* 2014, 9, 495-502). Replacement of the morpholine group of LY294002 with a piperizine group (LY303511) causes it to lose PI3K inhibition activity but retain BET bromodomain inhibition. The morpholine ring is critical for binding in the PI3K catalytic pocket and cannot be replaced even by the structually similar thiomorpholine (C. J. Vlahos et al., *J. Biol. Chem.* 1994, 269, 5241-5248). Other kinases have also been shown to have some BET inhibition activity. For example the PLK1 inhibitor BI2536 and the JAK2 inhibitor TG101209 also potently inhibit the BET protein BRD4-1 (S. W. J. Ember, *ACS Chem. Biol.* 2014, 9, 1160-1171). However, the ability of kinase inhibitors to inhibit bromodomain proteins is not a general property. As demonstrated by a recent study, of 628 kinase inhibitors tested only 7 inhibitors, namely BI2536, BI6727 (volasertib), the RSK inhibitor NI-F1870, the JAK inhibitor TG-101348, the FAK inhibitor PF-431396, the beta-isoform selective PI3K inhibitor GSK2636771, and the mTOR kinase inhibitor PP-242, showed some degree of BRD4-1 inhibitory activity (P. Ciceri et al., *Nat. Chem. Biol.* 2014, 10, 305-312).

There remains a need for potent inhibitors of bromodomain proteins, especially BRD4, as well as a need for small molecules that inhibit both bromodomain proteins and PI3K especially ones that inhibit both PI3K and BRD4.

SUMMARY OF THE INVENTION

The present invention relates to thienopyranone compounds that are useful in therapeutic methods including as inhibitors of kinases including PI-3 kinase and/or inhibitors of bromodomain proteins. In particular, the invention relates to new thienopyranone compounds, conjugates thereof, pharmaceutical compositions containing the thienopyranones or conjugates thereof as active ingredients, and use of the thienopyranone compounds as therapeutic agents including antitumor agents for the treatment of disorders including but not limited to cancer. Some of the compounds disclosed in this application have been previously described in U.S. Pat. No. 8,557,807, the entire contents of which is herein incorporated by reference.

The present invention relates in one aspect to methods of treating diseases in mammals using thienopyranone (7H-thieno[3,2-b]pyran-7-ones) compounds of the general Formula I or a pharmaceutically acceptable salt thereof:

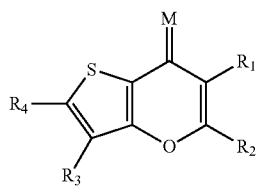

Formula I wherein M is oxygen (O) or sulfur (S);
R1 is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;
R2 is selected from R1 or

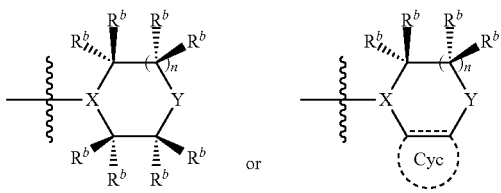

where X is C, N, P, P(O), SiR$^b$;
n is 0, 1, or 2;
Y is C—R1, O, S, NR$^a$, —C(O)(NH$_2$), —P(Z)$_m$R$^a$, SiR$^a$R$^b$, BR$^b$;
Z is O or S;
m=0 or 1;
R$^a$ is hydrogen (H) or independently at each instance any group defined in R1;
R$^b$ is hydrogen (H) or independently at each instance any group defined in R1;
R3 is selected from R1;
R4 is selected from R1; and
Cyc is an aryl, substituted aryl, heterocycle, substituted heterocycle, carbocycle, and substituted carbocycle.

As used herein, the expression "a compound of Formula X" (e.g. Formula I-IX), or the expression "a compound of the invention" includes the compound, conjugates thereof, and any conventional prodrug thereof, as well as a pharmaceutically acceptable salt of said compound, conjugate, or prodrug. The compounds of the present invention also encompass polymorphic forms, solvates, hydrates, salts and complexes thereof.

Compounds of of the invention, e.g. Formula I are useful as inhibitors of kinases including, for example and not limited to, mTOR kinase, PIM-1 kinase, PLK-1 kinase, DNA-PK kinase, and PI-3 kinases.

Compounds of the invention, e.g. Formula I are also useful as inhibitors of bromodomain proteins including for example but not limited to BRD2, BRD3, and BRD4. Compounds of Formula I are also useful as inhibitors of both kinases and bromodomain proteins. Compounds of Formula I are useful as inhibitors of PI3K and bromodomain proteins including but not limited to BRD4.

In addition, various compounds of Formula I are useful inhibitors of tumor growth and for the treatment of cancer as well as for treating inflammation, obesity, and acting as antiviral agents.

Accordingly, it is an object of the present invention to provide compounds, compositions, and methods for treating disease and for inhibiting kinases, for example PI-3 kinases, and/or for inhibiting bromodomain proteins and their associated epigenetic mechanisms, useful for inhibiting cancerous tumor growth and for treating other diseases and conditions.

Compounds (or salts thereof) of the present invention are useful as an active ingredient in the manufacture of a medicament for use in inhibiting kinase activity e.g. PI-3 kinase activity and/or for inhibiting a bromodomain protein(s).

The present invention also relates to a method of inhibiting kinase activity in a mammal including a human comprising administering to a mammal in need of treatment, a kinase inhibiting dose of a compound of Formulas I-IX or conjugate or prodrug thereof having any of the definitions herein.

The present invention further relates to a method of inhibiting PI-3 kinase comprising administering to a mammal in need of treatment, including a human, a PI-3 kinase-inhibiting dose of a compound of Formulas I-IX or conjugate or prodrug thereof having any of the definitions herein. The present invention further relates to a method of inhibiting PI-3 kinase comprising administering to insects or fungi for agricultural uses.

Further, the present invention provides a method of inhibiting tumor growth comprising administering to a mammal in need of treatment, including a human, an effective dose of a compound of Formulas I-IX, or conjugate or prodrug thereof, having any of the definitions herein.

In another aspect the invention relates to a method of regulating gene transcription in a cell comprising exposing a bromodomain containing protein to a compound of Formula I-IX.

In another aspect the present invention relates to a method of inhibiting bromodomain-mediated recognition of an acetyl lysine region of a protein comprising exposing the bromodomain to a compound of Formula I-IX.

As an additional feature of the invention there is provided a pharmaceutical formulation comprising in association with a pharmaceutically acceptable carrier, diluent or excipient, a conjugate of a compound of Formulas I-IX (or of a pharmaceutically acceptable salt thereof) as provided in any of the descriptions herein.

In another aspect, the present invention relates to treating a disease, including but not limited to, cancer, non-cancer proliferative disease, sepsis, autoimmune disease, viral infection, atherosclerosis, Type 2 diabetes, obesity, inflammatory disease, and Myc-dependent disorder by administering a compound of the invention.

These and other objects of the invention are evidenced by the summary of the invention, the description of the preferred embodiments and the claims.

BRIEF DESCRIPTION OF THE DRAWINGS

FIG. 1A provides the structure of known BET inhibitor JQ1(+).

FIG. 1B shows the structure of known BET inhibitor I-BET762.

FIG. 1C shows the structure of known BET inhibitor I-BET151.

FIG. 1D shows the general structure for acetyl-lysine mimetics acting as broomodomain ligands.

DETAILED DESCRIPTION

A. Definitions

Figure 2:
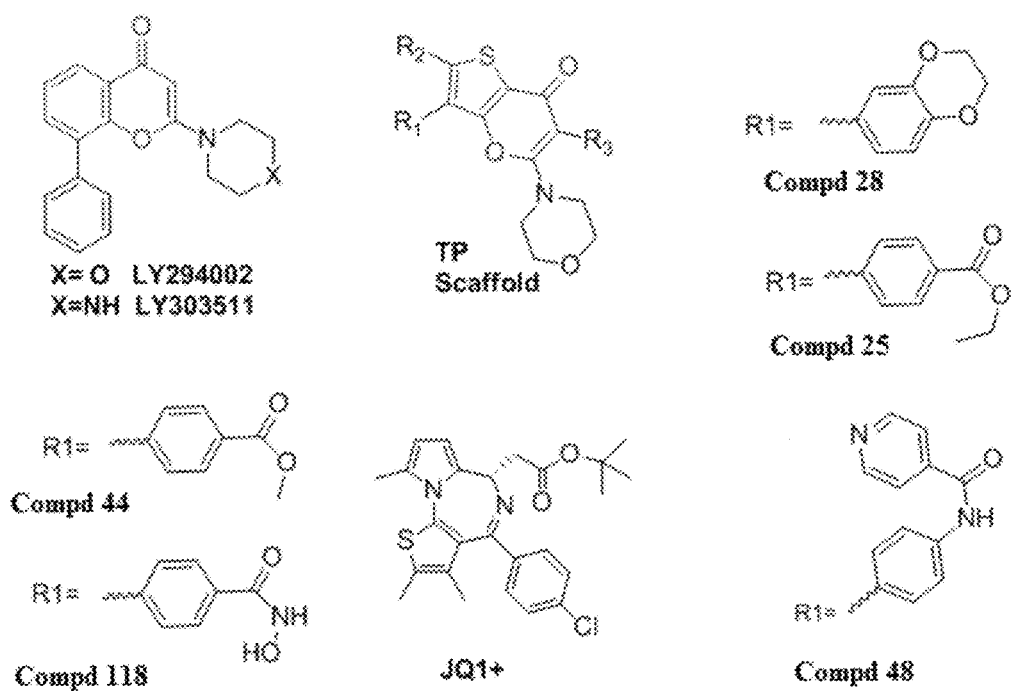
FIG. 2 shows the structures of LY294002, LY303511, TP Scaffolds, Compound 28, Compound 44, Compound 118, Compound 48, and JQ1+.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Adrenal Glands: neuroblastoma; and breast cancer.

The term "cancerous cell" as provided herein, includes a cell affected by any one of the above-identified cancers. The term "cancer stem cell" refers to a subpopulation of cells in a solid or non-solid tumor that demonstrate enhanced drug efflux properties, are lacking in cell cycle progression, and are resistant to anoikis.

As used herein, the term "branched" refers to a group containing from 1 to 24 backbone atoms wherein the backbone chain of the group contains one or more subordinate branches from the main chain. Preferred branched groups herein contain from 1 to 12 backbone atoms. Examples of branched groups include, but are not limited to, isobutyl, t-butyl, isopropyl, —$CH_2CH_2CH(CH_3)CH_2CH_3$, —$CH_2CH(CH_2CH_3)CH_2CH_3$, —$CH_2CH_2C(CH_3)_2CH_3$, —$CH_2CH_2C(CH_3)_3$ and the like.

The term "unbranched" as used herein refers to a group containing from 1 to 24 backbone atoms wherein the backbone chain of the group extends in a direct line. Preferred unbranched groups herein contain from 1 to 12 backbone atoms.

The term "cyclic" or "cyclo" as used herein alone or in combination refers to a group having one or more closed rings, whether unsaturated or saturated, possessing rings of from 3 to 12 backbone atoms, preferably 3 to 7 backbone atoms.

The term "lower" as used herein refers to a group with 1 to 6 backbone atoms.

The term "saturated" as used herein refers to a group where all available valence bonds of the backbone atoms are attached to other atoms. Representative examples of saturated groups include, but are not limited to, butyl, cyclohexyl, piperidine and the like.

The term "unsaturated" as used herein refers to a group where at least one available valence bond of two adjacent backbone atoms is not attached to other atoms. Representative examples of unsaturated groups include, but are not limited to, —$CH_2CH_2CH=CH_2$, phenyl, pyrrole and the like.

The term "aliphatic" as used herein refers to an unbranched, branched or cyclic hydrocarbon group, which may be substituted or unsubstituted, and which may be saturated or unsaturated, but which is not aromatic. The term aliphatic further includes aliphatic groups, which comprise oxygen, nitrogen, sulfur or phosphorous atoms replacing one or more carbons of the hydrocarbon backbone.

The term "aromatic" as used herein refers to an unsaturated cyclic hydrocarbon group which may be substituted or unsubstituted having 4n+2 delocalized π(pi) electrons. The term aromatic further includes aromatic groups, which comprise a nitrogen atom replacing one or more carbons of the hydrocarbon backbone. Examples of aromatic groups include, but are not limited to, phenyl, naphthyl, thienyl, furanyl, pyridinyl, (is)oxazoyl and the like.

The term "substituted" as used herein refers to a group having one or more hydrogens or other atoms removed from a carbon or suitable heteroatom and replaced with a further group. Preferred substituted groups herein are substituted with one to five, most preferably one to three substituents. An atom with two substituents is denoted with "di," whereas an atom with more than two substituents is denoted by "poly". Representative examples of such substituents include, but are not limited to aliphatic groups, aromatic groups, alkyl, alkenyl, alkynyl, aryl, alkoxy, halo, aryloxy, carbonyl, acryl, cyano, amino, nitro, phosphate-containing groups, sulfur-containing groups, hydroxyl, alkylcarbonyloxy, arylcarbonyloxy, alkoxycarbonyloxy, aryloxycarbonyloxy, alkylcarbonyl, arylcarbonyl, alkoxycarbonyl, aminocarbonyl, alkylaminocarbonyl, dialkylaminocarbonyl, alkylthiocarbonyl, acylamino, amidino, imino, alkylthio, arylthio, thiocarboxylate, alkylsulfinyl, trifluoromethyl, azido, heterocyclyl, alkylaryl, heteroaryl, semicarbazido, thiosemicarbazido, maleimido, oximino, imidate, cycloalkyl, cycloalkylcarbonyl, dialkylamino, arylcycloalkyl, arylcarbonyl, arylalkylcarbonyl, arylcycloalkylcarbonyl, arylphosphinyl, arylalkylphosphinyl, arylcycloalkylphosphinyl, arylphosphonyl, arylalkylphosphonyl, arylcycloalkylphosphonyl, arylsulfonyl, arylalkylsulfonyl, arylcycloalkylsulfonyl, combinations thereof, and substitutions thereto.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

The terms "optionally substituted", "optionally substituted alkyl", "optionally substituted alkenyl", "optionally substituted alkynyl", "optionally substituted carbocyclic", "optionally substituted aryl", "optionally substituted heteroaryl", "optionally substituted heterocyclic", and any other optionally substituted group as used herein, refer to groups that are substituted or unsubstituted by independent replacement of one, two, or three or more of the hydrogen atoms thereon with substituents including, but not limited to: —F, —Cl, —Br, —I, —OH, protected hydroxy, alkoxy, oxo, thiooxo, —$NO2$, —CN, —$CF3$, —$N3$, —$NH_2$, protected amino, —NH— alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl, —$CONH2$, —CONH-alkyl, —CONH-alkenyl, —CONH-alkynyl, —CONH-cycloalkyl, —CONH-aryl, —CONH-heteroaryl, —CONH-heterocycloalkyl, —$OCO2$-alkyl, —$OCO2$-alkenyl, —$OCO2$-alkynyl, —$OCO2$-cycloalkyl, —$OCO2$-aryl, —$OCO2$-heteroaryl, —$OCO2$-heterocycloalkyl, —$OCONH2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —NHCO2-alkyl, —NHCO2-alkenyl, —NHCO2-alkynyl, —NHCO2-cycloalkyl, —NHCO2-aryl, —NHCO2-heteroaryl, —NHCO2-heterocycloalkyl, —NHC(O)NH$_2$, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, —NHC(S)NH$_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —NHC(NH)NH$_2$, —NHC(NH)NH-alkyl, —NHC(NH)NH-alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl —SO2NH2, —SO2NH-alkyl, —SO2NH-alkenyl, —SO2NH-alkynyl, —SO2NH-cycloalkyl, —SO2NH-aryl, —SO2NH-heteroaryl, —SO2NH-heterocycloalkyl, —NHSO2-alkyl, —NHSO2-alkenyl, —NHSO2-alkynyl, —NHSO2-cycloalkyl, —NHSO2-aryl, —NHSO2-heteroaryl, —NHSO2-heterocycloalkyl, —CH2NH2, —CH2SO2CH3, -alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

The term "unsubstituted" as used herein refers to a group that does not have any further groups attached thereto or substituted therefore.

The term "alkyl" as used herein, alone or in combination, refers to a branched or unbranched, saturated aliphatic group. The alkyl radical may be optionally substituted independently with one or more substituents described herein. Lower alkyl refers to alkyl groups of from one to six carbon atoms. Examples of lower alkyl groups include methyl, ethyl, propyl, isopropyl, butyl, s-butyl, t-butyl, isobutyl, pentyl, and the like. Higher alkyl refers to alkyl groups containing more than seven carbon atoms. Exemplary alkyl groups are those of C$_{20}$ or below. In this application, alkyl refers to alkanyl, alkenyl, and alkynyl residues (and combinations thereof); it is intended to include vinyl, allyl, isoprenyl, and the like. Thus when an alkyl residue having a specific number of carbons is named, all geometric isomers having that number of carbons are intended to be encompassed; thus, for example, either "butyl" or "C$_4$ alkyl" is meant to include n-butyl, sec-butyl, isobutyl, t-butyl, isobutenyl and but-2-ynyl groups; and for example, "propyl" or "C$_3$ alkyl" each include n-propyl, propenyl, and isopropyl. Representative examples of alkyl groups include, but are not limited to, methyl, ethyl, n-propyl, isopropyl, n-butyl, isobutyl, sec-butyl, tert-butyl, octyl, decyl, tetradecyl, hexadecyl, eicosyl, tetracosyl and the like. The terms "alkyl" or "alk" as used herein refer to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (1-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)$_2$), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, 1-heptyl, 1-octyl, and the like.

The terms "carbocycle", "carbocyclyl", "carbocyclic ring", and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. The cycloalkyl radical may be optionally substituted independently with one or more substituents described herein. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The term "alkenyl" as used herein alone or in combination refers to a branched or unbranched, unsaturated aliphatic group containing at least one carbon-carbon double bond which may occur at any stable point along the chain. The alkenyl radical may be optionally substituted independently with one or more substituents described herein, and includes radicals having "cis" and "trans" orientations, or alternatively, "E" and "Z" orientations. Representative examples of alkenyl groups include, but are not limited to, ethenyl, E- and Z-pentenyl, decenyl and the like.

The term "alkynyl" as used herein alone or in combination refers to a branched or unbranched, unsaturated aliphatic group containing at least one carbon-carbon triple bond which may occur at any stable point along the chain. The alkynyl radical may be optionally substituted independently with one or more substituents described herein. Representative examples of alkynyl groups include, but are not limited to, ethynyl, propynyl, propargyl, butynyl, hexynyl, decynyl and the like.

The term "aryl" as used herein alone or in combination refers to a substituted or unsubstituted aromatic group, which may be optionally fused to other aromatic or non-aromatic cyclic groups. Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "heteroaryl" and "heteroar-", used alone or as part of a larger moiety, e.g., "heteroaralkyl", or "heteroaralkoxy", refer to groups having 5 to 18 ring atoms, preferably 5, 6, 7, 9, or 14 ring atoms; having 6, 10, or 14 π (pi) electrons shared in a cyclic array; and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heteroaryl may be a single ring, or two or more fused rings. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. Examples include, but are not limited to, pyridinylmethyl, pyrimidinylethyl and the like.

The term "alkoxy" as used herein alone or in combination refers to an alkyl, alkenyl or alkynyl group bound through a single terminal ether linkage. Examples of alkoxy groups include, but are not limited to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, 3-methylpentoxy, fluoromethoxy, difluoromethoxy, trifluoromethoxy, chloromethoxy, dichloromethoxy, and trichloromethoxy.

The term "aryloxy" as used herein alone or in combination refers to an aryl group bound through a single terminal ether linkage.

The terms "halogen", "halo", and "hal" as used herein refer to monovalent atoms of fluorine, chlorine, bromine, iodine and astatine.

The term "hetero" or "heteroatom" as used herein combination refers to a group that includes one or more atoms of any element other than carbon or hydrogen. Representative examples of hetero groups include, but are not limited to, those groups that contain heteroatoms including, but not limited to, nitrogen, oxygen, sulfur and phosphorus.

The term "heterocycle", "heterocyclyl", "heterocyclic ring" or "heterocyclic" as used herein refers to a cyclic group containing a heteroatom in a 3 to 7-membered ring moiety. The heterocyclic radical may be optionally substituted independently with one or more substituents described herein. Representative examples of heterocycles include, but are not limited to, pyridine, piperadine, pyrimidine, pyridazine, piperazine, pyrrole, pyrrolidinone, pyrrolidine, morpholine, thiomorpholine, indole, isoindole, imidazole, triazole, tetrazole, furan, benzofuran, dibenzofuran, thiophene, thiazole, benzothiazole, benzoxazole, benzothiophene, quinoline, isoquinoline, azapine, naphthopyran, furanobenzopyranone and the like.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical" are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

The term "substituent" means any group selected from H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, halo, haloalkyl, haloalkoxy, hydroxy, oxo (valency rules permitting), lower alkanyl, lower alkenyl, lower alkynyl, alkoxy, optionally substituted cycloalkyl, optionally substituted heterocycloalkyl, optionally substituted aryl, optionally substituted heteroaryl, alkylaminoalkyl, dialkylaminoalkyl, carboxy, carboxy ester, —C(O)NR$^5$R" (where R$^5$ is hydrogen or alkyl and R" is hydrogen, alkyl, aryl, or heterocyclyl), —NR$^5$C(O)R" (where R$^5$ is hydrogen or alkyl and R" is alkyl, aryl, or heterocyclyl), amino, alkylamino, dialkylamino, —NHR", and —NHS(O)$_2$R' (where R' is alkyl, aryl, or heteroaryl).

The term "carbonyl" or "carboxy" as used herein alone or in combination refers to a group that contains a carbon-oxygen double bond. Representative examples of groups which contain a carbonyl include, but are not limited to, aldehydes (i.e., formyls), ketones (i.e., acyls), carboxylic acids (i.e., carboxyls), amides (i.e., amidos), imides (i.e., imidos), esters, anhydrides and the like.

The term "carbamate" as used herein alone or in combination refers to an ester group represented by the general structure —NH(CO)O—. Carbamate esters may have alkyl or aryl groups substituted on the nitrogen, or the amide function.

The term "cyanate", "isocyanate", "thiocyanate", or "isothiocyanate" as used herein alone or in combination refers to an oxygen- or sulfur-carbon double bond carbon-nitrogen double bond. Representative examples of cyano groups include, but are not limited to, isocyanate, isothiocyanate and the like.

The term "cyano", "cyanide", "isocyanide", "nitrile", or "isonitrile" as used herein alone or in combination refers to a carbon-nitrogen triple bond.

The term "amino" as used herein alone or in combination refers to a group containing a backbone nitrogen atom.

Representative examples of amino groups include, but are not limited to, alkylamino, dialkylamino, arylamino, diarylamino, alkylarylamino, alkylcarbonylamino, arylcarbonylamino, carbamoyl, ureido and the like.

The term "phosphate-containing group" as used herein refers to a group containing at least one phosphorous atom in an oxidized state. Representative examples include, but are not limited to, phosphonic acids, phosphinic acids, phosphate esters, phosphinidenes, phosphinos, phosphinyls, phosphinylidenes, phosphos, phosphonos, phosphoranyls, phosphoranylidenes, phosphorosos and the like.

The term "sulfur-containing group" as used herein refers to a group containing a sulfur atom. Representative examples include, but are not limited to, sulfhydryls, sulfenos, sulfinos, sulfinyls, sulfos, sulfonyls, thios, thioxos and the like.

The term "optional" or "optionally" as used herein means that the subsequently described event or circumstance may or may not occur, and that the description includes instances where said event or circumstance occurs and instances where it does not. For example, the phrase "optionally substituted alkyl" means that the alkyl group may or may not be substituted and that the description includes both unsubstituted alkyl and substituted alkyl.

The term "targeting agent" as used herein means any moiety whose attachment to a compound of the invention allows the increase in concentration of the compound at a site of treatment, for example, a tumor site. Examplary targeting agents include but are not limited to carbohydrates, peptides, vitamins, nanoparticles (including albumin nanoparticles), liposomal encapsulation, and antibodies.

The term "effective amount" or "effective concentration" when used in reference to a compound, product, or composition as provided herein, means a sufficient amount of the compound, product or composition to provide the desired pharmaceutical or therapeutic result. The exact amount required will vary depending on the particular compound, product or composition used, its mode of administration and the like. Thus, it is not always possible to specify an exact "effective amount". However, an appropriate effective amount may be determined by one of ordinary skill in the art informed by the instant disclosure using only routine experimentation.

The term "hydrolyzable" as used herein refers to whether the group is capable of or prone to hydrolysis (i.e., splitting of the molecule or group into two or more new molecules or groups).

The term "pharmaceutically acceptable salt" of a compound of the instant invention (e.g., Formula I) is one which is the acid addition salt of a basic compound of the invention with an inorganic or organic acid which affords a physiologically acceptable anion or which is the salt formed by an acidic compound of the invention with a base which affords a physiologically acceptable cation.

The term "prodrug" or "procompound" as used in this application refers to a precursor or derivative form of a compound of the invention that may be less cytotoxic to cells compared to the parent compound or drug and is capable of being enzymatically, non-enzymatically, radically, irradiatively, or hydrolytically activated or converted into the more active parent form. See, e.g., Wilman, "Prodrugs in Cancer Chemotherapy", *Biochem. Soc. Trans.* 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "conjugate" as used herein refers to a compound that has been formed by the joining of two or more compounds via either a covalent or non-covalent bond.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the terms "treatment", "treat", and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (i.e., in light of a history of symptoms and/or in light of genetic or other susceptibility factors). Treatment may also be continued after symptoms have resolved, for example to prevent or delay their recurrence.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention" and "compounds of the present invention" include compounds of Formulas I-IX and stereoisomers, geometric isomers, tautomers, solvates, metabolites, and pharmaceutically acceptable salts, prodrugs, and conjugates thereof.

The term "TP scaffold" or "Thienopyranone scaffold" refers to a compound of general Formula I as described herein.

B. Compounds

The present invention relates in part to compounds and therapeutic methods of use of compounds of the Formula I:

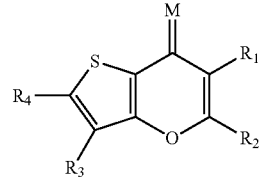

Formula I wherein M is O or S;
R1 is selected from H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;
R2 is selected from R1 or

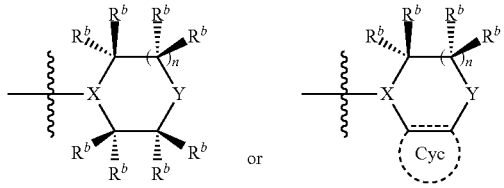

Where X is C, N, P, P(O), SiR$^b$;
n is 0, 1, or 2;
Y is C—R1, O, S, NR$^a$, —C(O)(NH$_2$), —P(Z)$_m$R$^a$, SiR$^a$R$^b$, BR$^b$;
Z is O or S;
m=0 or 1;
R$^a$ is hydrogen (H) or independently at each instance any group defined in R1;
R$^b$ is hydrogen (H) or independently at each instance any group defined in R1;
R3 is selected from R1;
R4 is selected from R1; and
Cyc is an aryl, substituted aryl, heterocycle, substituted heterocycle, carbocycle, and substituted carbocycle.

A particular compound of Formula I is one wherein a substitutent of R1 comprises a bone directing group such as, for example, amino phosphonic acid, bisphsphonate, or the like.

The present invention also provides methods of use for compounds of Formulas II-IV:

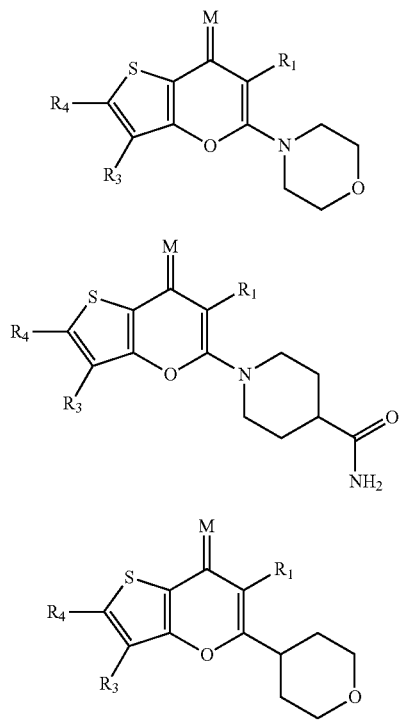

Formula II

Formula III

Formula IV wherein M is O or S;
R1 is selected from H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;
R3 is independently, at each instance, R1; and
R4 is independently, at each instance, R1.

A particular compound of Formulas II-IV is one wherein a substitutent of R1 comprises a bone directing group such as, for example, amino phosphonic acid, bisphsphonate, or the like.

The present invention also provides methods of use for compounds of Formulas V-VII:

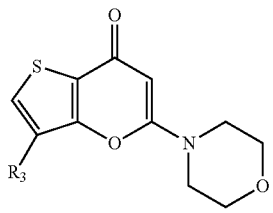

Formula V

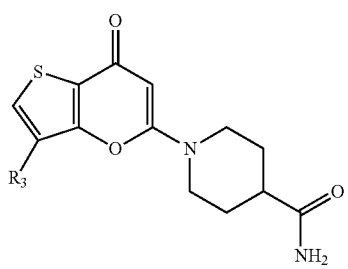

Formula VI

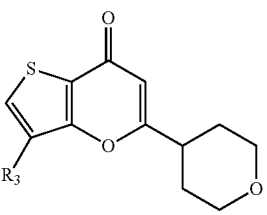

Formula VII wherein R3 is selected from H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate.

A particular compound of Formulas V-VII is one wherein a substitutent of R3 comprises a bone directing group such as, for example, amino phosphonic acid, bisphsphonate, or the like.

C. Conjugates

The present invention also provides methods of use for conjugates of Formula I. In one embodiment conjugates are formed by alkylating a compound of Formula I with a linker group (L), the linker group optionally being substituted with a targeting agent (T). Methods for producing conjugates for this aspect of the invention include alkylation procedures disclosed in U.S. Pat. Nos. 6,949,537 and 7,396,828 the entire contents of which is herein incorporated by reference. In one embodiment of this aspect of the invention a compound of Formula I is reacted with a halomethyl ester compound of Formula Q:

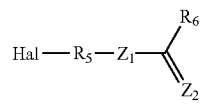

wherein Hal is a halogen; R5 is $CH_2$, $CH(CH_3)$, $CH(Ph)$, $C(CH_3)(COOH)$, or $CH(CH(CH_3)2)$;

Z1 and Z2 are independently S or O;

R6 is hydrogen, optionally substituted aliphatic, optionally substituted aryl, alkoxy, carboxy, amino, heterocycle, aryloxy, and optionally substituted therewith a targeting agent (T) to form R6-T.

Targeting Agent.

In another embodiment, conjugates used in methods of the present invention are those compounds wherein, $R_6$ further comprises one or more targeting agents (T) covalently attached thereto. Targeting agents allow the conjugates used in methods of the present invention to be delivered selectively to specific types of cells, tissues, organs or extracellular structures such as receptors. In some applications it may be desirable to limit the location of a drug or prodrug to the area of treatment or at least prevent it from reaching tissues where it can cause undesirable side effects, and to ensure that at any particular time effective, but not excessive, amounts of the drug are used. The use of targeting agents may allow the conjugates of the present invention to be concentrated at the site of treatment. Once delivered to a site of treatment, the linker may be enzymatically cleaved or hydrolyzed to yield a compound of formula I. Moreover, the use of a targeting agent may limit the dosage required to achieve an effective concentration of a drug at the site of treatment. The use of targeting agents may also reduce the frequency of dosages required.

Suitable targeting agents are preferentially attached to compounds used in methods of the present invention via a covalent bond which may be formed by methods including, but not limited to, a nucleophilic or electrophilic group of the targeting agent that is covalently reacted with an electrophilic or nucleophilic group (respectively) on the linker. In one embodiment, suitable targeting agents are those disclosed in U.S. Pat. No. 6,949,537, the entire contents of which is herein incorporated by reference.

In one embodiment of the present invention, conjugates used in methods of the present invention are those compounds wherein, R6-T is selected from the group consisting of the following:

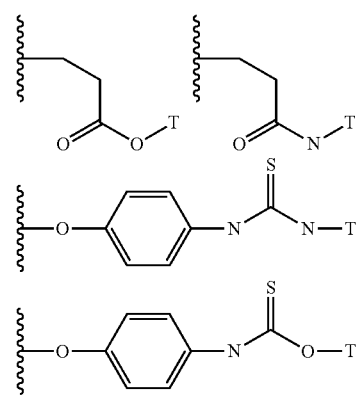

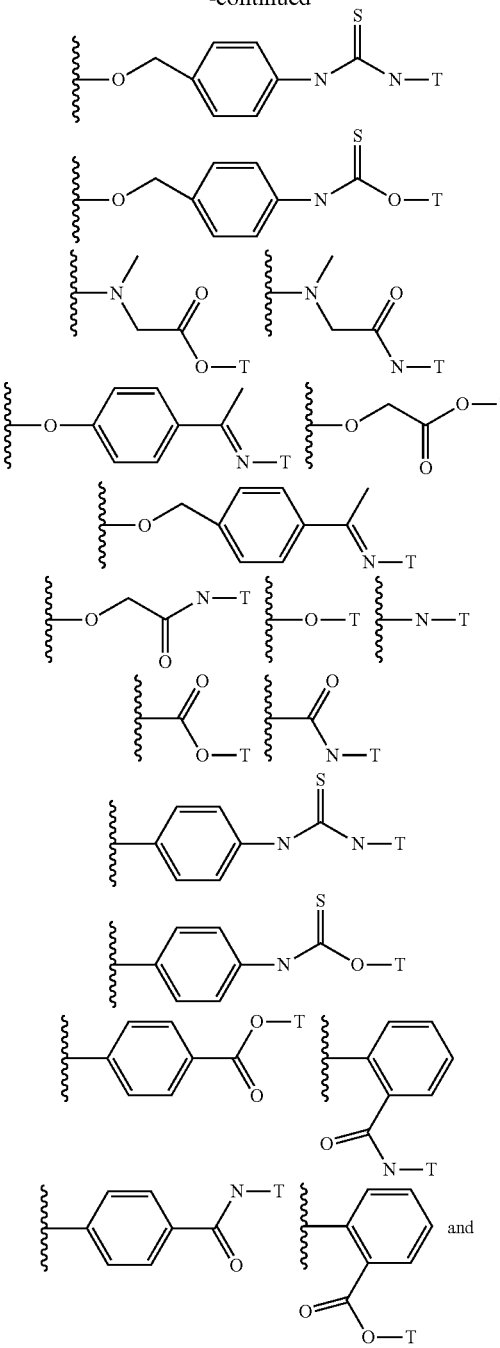

Targeting agents which may be reacted with the conjugates used in methods of the present invention include, but are not limited to, carbohydrates, vitamins, peptides, proteins, nucleosides, nucleotides, nucleic acids, liposomes, lipids, nanoparticles (including albumin nanoparticles), bone-seeking agents and cartilage-seeking agents. The targeting agent may also be a molecule which is bound by a receptor in a desired tissue and optionally transported into a cell by a receptor-mediated process. Representative examples of such targeting agents include, but are not limited to, diazepines that bind to peripheral benzodiazepine receptors (PBRs) present in glial cells in the brain. Representative examples of such diazepines are discussed in G. Trapani et al., *Bioconjugate Chem.* 2003, 14, 830-839 entitled "Peripheral Benzodiazepine Receptor Ligand-Melphalan Conjugates for Potential Selective Drug Delivery to Brain Tumors," the contents of which are incorporated by reference.

Representative vitamins that may be used as targeting agents include, but are not limited to, folate, vitamin $B_{12}$ or vitamin C. The term "folate" encompasses folic acid derivatives with capacity to bind with folate-receptors. Representative examples of folates that may be used as targeting agents include, but are not limited to, folic acid, folinic acid, pteropolyglutamic acid, and folate receptor-binding pteridines such as tetrahydropterins, dihydrofolates, tetrahydrofolates and their deaza and dideaza analogs. Other suitable folates are folate analogs including, but not limited to, aminopterin, amethopterin (methotrexate), $N_{10}$-methylfolate, 2-deamino-hydroxyfolate, deaza analogs such as 1-deazamethopterin or 3-deazamethopterin, and 3'5'-dichloro4-amino-4-deoxy-$N_{10}$-methylpteroyl-glutamic acid (dichloromethotrexate). Methods of conjugating molecules to folates that are suitable for covalent attachment to compounds of the present invention are disclosed in U.S. Pat. Nos. 6,576,239, 5,820,847, 5,688,488, 5,108,921, 5,635,382, and 5,416,016 the contents of which are incorporated herein by reference. Methods of conjugating molecules to vitamin C that are suitable for covalent attachment of compounds of the present invention are disclosed in S. Manfrdini et al., *J. Med. Chem.* 2002, 45, 559-562, the contents of which are incorporated herein by reference.

Representative peptides and peptidomimetics that may be used as targeting agents include, but are not limited to, an RGD-containing peptide selected from the group consisting of RGDs, c(RGDfK), vitronectin, fibronectin, somatostatin-receptor agonists and somatostatin-receptor antagonists. Molecules that bind to the αvβ3 integrin receptor and act as antagonists may be used as targeting agents are described in U.S. Pat. Nos. 6,552,079, 6,426,353B, WO 2002/40505A2, and U.S. Patent Publications 2002/0055499, 2002/0061885, 2002/0065291, 2002/0072500, U.S. 2002/0072518; W. Arap et al., *Science* 1998, 279, 377-380; R. J. Kok et al., *Biojonjugate Chem.* 2002, 13, 128-135; D. A. Sipkins et al., *Nat. Med.* 1998, 4, 623-626; P. M. Winter et al., *Cancer Res.* 2003, 63, 5838-5843; and J. D. Hood et al., *Science* 2002, 296, 2404-2407; the contents of which are incorporated herein by reference. Representative proteins that may be used as targeting agents include, but are not limited to, antibodies or fragments thereof, such as a tumor-specific monoclonal antibody or fragment thereof. Representative bone-seeking agents that may be used as targeting agents include, but are not limited to, phosphonate, phosphonic acid, aminomethylphosphonic acid, phosphate, polyphosphate, and hydroxyapatite-binding polypeptides. Other peptides include chlorotoxin (U.S. Pat. No. 6,429,187B1) and tissue factor (G. M. Lanza et al., *Circulation* 2002, 106, 2842-2847).

Other suitable targeting agents include antibodies. The antibodies may be of classes IgG, IgM, IgA, IgD or IgE, or fragments or derivatives thereof, including Fab, $F(ab')_2$, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to a desired epitope or a sequence derived therefrom. The antibodies may also be a chimeric antibody. The antibodies may be directed against a variety of antigenic determinants including those associated with tumors, histocompatibility and other cell surface antigens, bacteria, fungi, viruses, enzymes, toxins, drugs and other biologically active molecules. Antigens associated with tumors for which antibodies may be specifically reactive include, but are not limited to, such antigens as are and include, but are not limited to, carcinoembryonic antigen (CEA), mucins such as TAG-72, human milk fat globule antigens, prostate serum antigent (PSA), prostate specific membrane antigen (PSMA), PS (phosphatidyl serine), and receptors including, but not limited to, the IL-2, EGF, VEGF and transferrin receptors. Other representative antigens associated with tumors include, but are not limited to, those tumor associated antigens described in J. R. Zalcberg et al., *J. Clin. Oncology* 1985, 3, 876-882, WO 01/68709A1, and U.S. Patent Publication US2004/0009122A1, the contents of which are incorporated herein by reference.

Other suitable targeting agents include glucose, galactose, mannose, mannose 6-phosphate, hormones (e.g., insulin, growth hormone, and the like), growth factors or cytokines (e.g., TGF-beta., EGF, insulin-like growth factor, and the like), $YEE(GalNAcAH)_3$ or derivatives, cobalamin, .alpha-2 macroglobulins, asialoglycoprotein, albumin, texaphyrin, metallotexaphyrin, antibodies, antibody fragments (e.g., Fab), single-chain antibody variable region (scFv), transferrin, any vitamin and any coenzyme.

The targeting agent may also be an agent that delivers a compound in a method of the invention to bone. Bone targeting agents include, but are not limited to, bisphosphonates, EDTMP DOTMP, and ABEDTMP, which are disclosed in U.S. Pat. Nos. 4,937,333, 4,882,142, 5,064,633 and WO-94/00143, the contents of which are incorporated herein by reference. DOTMP and EDTMP may be attached to the linker moiety by any suitable coupling method including, but not limited to, coupling chemistry where the R group can have an appropriate electrophilic or nucleophilic group that reacts with the nucleophilic or electrophilic (respectively) group of the linker moiety. Further details of the coupling chemistry are provided in *Tetrahedron* 1999, 55, 12997-13010, the contents of which are incorporated by reference. Further details of bone-targeted prodrugs and coupling chemistry are provided in *Proc. SPIE-Int. Soc. Opt. Eng.* 1999, 3600 (Biomedical Imagn. Reporters Dyes & Instrumental, 99-106; U.S. Pat. No. 5,177,054; *J. Med. Chem.* 1994, 37, 498-511; *Tetrahedron Lett.* 1989, 30, 7141-7144; T. J. Houghton et al., *J. Med. Chem.* 2008, 51, 6955-6969; and U.S. Pat. No. 5,955,453, the contents of which are incorporated by reference.

The targeting agent may be used to deliver a conjugate used in the methods of the invention (or salt thereof) to bone tissue as a slow release reservoir site for the compounds of the present invention. The targeting agent may be a bone seeking (osteotropic) moiety attached to the compounds of the present invention via an acid cleavable linker. Examples of an acid cleavable linker include, but are not limited to, an ortho acid-amide linkage. Under acidic conditions the protein-ACL-3 amide linkage is readily cleaved freeing the native amino group of the amide functionality as described in WO-94/00143 the contents of which are incorporated by reference. During osteoclastic bone resorption, which involves an acidic mediated mechanism, the attachment tethering the prodrug to bone may be cleaved releasing the compounds of the present invention. Methods and particular bone-targeting agents are disclosed in U.S. Pat. No. 6,949,537, the entire contents of which are herein incorporated by reference.

The targeting agent may also comprise an RGD peptide moiety. As discussed in F. Curnis et al., *Cancer Res.* 2004, 64, 565-571, RGD moieties target RGD fusion proteins to vasculature by interacting with cell adhesion receptors, including αvβ3 integrin.

Conjugate compounds used in methods according to another aspect of the invention are depicted by Formula VIII or Formula IX wherein a hydrolyzable linker Rc is in either of two positions (as shown).

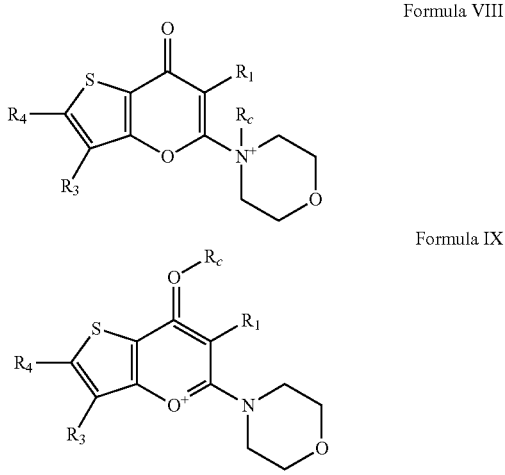

Formula VIII

Formula IX wherein R1, R3, and R4 independently represent H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

Rc comprises a hydrolyzable linker group (L) which is optionally substituted with a targeting agent (T).

In one embodiment, a targeted conjugate used in the methods of the invention of Formula I is one in which Rc has the structure:

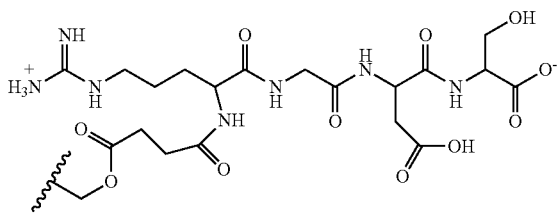 [SMILES: *COC(=O)CCC(=O)NC(CCCNC(=N)N)C(=O)NCC(=O)NC(CC(=O)O)C(=O)NC(CO)C(=O)[O-]]

A pharmaceutically acceptable salt of a compound used in the methods of the instant invention is one which is the acid addition salt of a basic compound of formula I with an inorganic or organic acid which affords a physiologically acceptable anion or which is the salt formed by an acidic compound of Formula I with a base which affords a physiologically acceptable cation and provides a particular aspect of the invention. Examples of such acids and bases are provided hereinbelow.

As an additional aspect of the invention there is provided methods of using a pharmaceutical formulation comprising in association with a pharmaceutically acceptable carrier, diluent or excipient, a compound of Formula I-IX (or a pharmaceutically acceptable salt thereof) as provided in any of the descriptions herein.

In addition, compounds (or salts thereof) used in the methods of the present invention are useful as an active ingredient in the manufacture of a medicament for use in inhibiting kinase activity, e.g., PI-3 kinase activity.

The present invention also provides a method for treating a disease in a human or other mammal including, but not limited to, cancer, non-cancer proliferative disease, sepsis, autoimmune disease, viral infaction, atheroscleosis, Type 1 or 2 diabetes, obesity, inflammatory disease, and Myc-depenent disorder by administering a therapeutically effective amount of a compound(s) of Formula I-IX or conjugate or prodrug thereof having any of the definitions herein.

The present invention further provides a method of inhibiting PI-3 kinase and/or bromodomain protein by providing a compound of Formula I-IX, including administering to a human in need of such treatment, an effective dose of a compound of Formula I-IX or conjugate or prodrug thereof having any of the definitions herein.

Further, the present invention provides a method of inhibiting tumor growth comprising administering to a mammal in need of treatment, an effective dose of a compound of Formula I-IX, or conjugate or prodrug thereof, having any of the definitions herein.

Also, there is provided a compound of Formula I-IX (or conjugate, prodrug, or salt thereof) having any of the definitions herein for use as an anticancer agent.

In addition, there is provided use of a compound of Formula I-IX having any of the definitions herein for the manufacture of a medicament, including a medicament for treatment of cancer.

As an additional feature of the invention there is provided a pharmaceutical formulation comprising in association with a pharmaceutically acceptable carrier, diluent or excipient, a conjugate of a compound of Formula I-IX (or of a pharmaceutically acceptable salt thereof) as provided in any of the descriptions herein.

The present invention also includes methods of use of isotopically-labeled compounds, and pharmaceutically acceptable salts thereof, which are identical to those recited in Formulas I through IX, but replace one or more atoms by a corresponding isotope. Examples of isotopes that can be incorporated into compounds of the invention include isotopes of hydrogen, carbon, nitrogen, oxygen, phosphorous, fluorine and chlorine. Compounds of the present disclosure, conjugates thereof, and pharmaceutically acceptable salts of said compounds or of said conjugates which contain the aforementioned isotopes and/or other isotopes of other atoms are within the scope of this disclosure. Certain isotopically-labeled compounds of the present disclosure, for example those into which radioactive isotopes, such as $^2$H, $^3$H, $^{14}$C, $^{15}$N, $^{32}$P and $^{131}$I are incorporated, are useful in drug and/or substrate tissue distribution assays for example when imaging tumors. Fluorine-18 ($^{18}F$) is particularly preferred for ease of preparation and detectability. Isotopically labeled compounds of the invention can generally be prepared by carrying out the procedures disclosed in the Schemes and/or in the Examples and Preparations below, by substituting a readily available isotopically labeled reagent for a non-isotopically labeled reagent.

It will be appreciated that certain compounds used in the methods of the invention of Formula I-IX (or salts, procompounds, conjugates, etc.) may exist in, and be isolated in, isomeric forms, including tautomeric forms, cis- or trans-isomers, as well as optically active, racemic, enantiomeric or diastereomeric forms. It is to be understood that the present invention encompasses a compound of Formula I-IX in any of the tautomeric forms or as a mixture thereof; or as a mixture of diastereomers, as well as in the form of an individual diastereomer, and that the present invention encompasses a compound of Formula I-IX as a mixture of enantiomers, as well as in the form of an individual enantiomer, any of which mixtures or form possesses inhibitory properties against kinases including PI-3 kinase, it being well known in the art how to prepare or isolate particular forms and how to determine inhibitory properties against kinases by standard tests including those described herein below.

In addition, a compound of Formula I-IX (or salt, procompound, conjugate thereof, etc.) used in the methods of the invention may exhibit polymorphism or may form a solvate with water or an organic solvent. The present invention also encompasses any such polymorphic form, any solvate or any mixture thereof.

As mentioned above, the methods of using the invention includes a pharmaceutically acceptable salt of a compound defined by the above Formula I-IX. A basic compound used in the methods of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

D.1. Synthesis of Compounds and Conjugates

The compounds of the present invention may be prepared by the examples herein as well as processes known in the chemical art and described in U.S. Pat. No. 8,557,807 and references therein as well as G. A. Morales et al., *J. Med. Chem.* 2013, 56, 1922-1939 the entire contents of which are herein incorporated by reference. Starting materials and intermediates used to prepare a compound of the invention are either commercially available or can be prepared by one of ordinary skill in the art. Conjugates used in the methods of the invention can be made, for example, by the procedures disclosed in U.S. Pat. Nos. 6,949,537, 7,396,828, and 8,557,807 the entire contents of which are herein incorporated by reference.

The compounds used in the methods of the invention, or their pharmaceutically acceptable salts, may have asymmetric carbon atoms or quaternized nitrogen atoms in their structure. It will be appreciated that certain compounds of Formula I (or salts, conjugates, etc.) may exist in, and be isolated in, isomeric forms, including tautomeric forms, cis- or trans-isomers, as well as optically active, racemic, enantiomeric, or diastereomeric forms. It is to be understood that the present invention encompasses a compound of general Formula I in any of the tautomeric forms or as a mixture thereof; or as a mixture of diastereomers, as well as in the form of an individual diastereomer, and that the present invention encompasses a compound of Formula I as a mixture of enantiomers, as well as in the form of an individual enantiomer, any of which mixtures or form possesses inhibitory properties against kinases, for example PI3 kinases. The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of the compounds used in the methods of the invention.

E. Formulations

As an additional aspect of the invention there is provided a pharmaceutical formulation or composition comprising in association with a pharmaceutically acceptable carrier, diluent or excipient, a compound of the invention, e.g. Formula I-IX (or a pharmaceutically acceptable salt or procompound or conjugate thereof) as provided in any of the descriptions herein for use in a method of the invention. Compositions of the present invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions used in the methods of the present invention may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Compositions used in the methods of the present invention may also be formulated as suppositories, which may contain suppository bases including, but not limited to, cocoa butter or glycerides. Compositions of the present invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of the present invention may also be formulated transdermal formulations comprising aqueous or nonaqueous vehicles including, but not limited to, creams, ointments, lotions, pastes, medicated plaster, patch, or membrane.

Compositions used in the methods of the present invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions used in the methods of the present invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions used in the methods of the present invention may also be formulated as a liposome preparation. The liposome preparation can comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh et al., U.S. Pat. No. 4,621,023 of Redziniak et al., or U.S. Pat. No. 4,508,703 of Redziniak et al., can be used. Other suitable formulations can employ niosomes. Niosomes are lipid vesicles similar to liposomes, with membranes consisting largely of non-ionic lipids, some forms of which are effective for transporting compounds across the stratum corneum.

The following formulation examples are illustrative only and are not intended to limit the scope of the compounds used in the methods of the invention in any way. The phrase "active ingredient" refers herein to a compound according to Formula I-IX or a pharmaceutically acceptable salt, procompound, conjugate, or solvate thereof.

Formulation 1: Tablet Containing the Following Components:

| Ingredient | Amount (mg/tablet) |
| --- | --- |
| Active ingredient | 250 |
| Dried starch | 200 |
| Magnesium stearate | 10 |
| Total | 460 mg |

Formulation 2: Capsules Containing the Following Components:

| Ingredient | Amount (mg/tablet) |
| --- | --- |
| Active ingredient | 60 |
| Dried starch | 44 |
| Magnesium stearate | 1.5 |
| Microcrystalline cellulose | 44 |
| Total | 150 mg |

Parenteral dosage forms for administration to patients by various routes including, but not limited to, subcutaneous, intravenous (including bolus injection), intramuscular, and intra-arterial are also contemplated by the present invention. Parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

An example parenteral composition used in the method of the invention would be intended for dilution with aqueous solution(s) comprising for example 5% Dextrose Injection, USP, or 0.9% Sodium Chloride Injection, USP, prior to administration to a patient, and is an aqueous solution that comprises irinotecan, sorbitol NF powder, and lactic acid, USP, and has a pH of from about 3.0 to about 3.8.

F. Therapeutic Use

Compounds and compositions described herein are generally useful for treating diseases and disorders including, but not limited to, cancer, non-cancer proliferative disease, sepsis, autoimmune disease, viral infaction, atherosclerosis, Type 2 diabetes, obesity, inflammatory disease, or Myc-dependent disorder by administering a therapeutically effective dose of a compound of Formula I-IX including but not limited to a compound disclosed in Table 3. Some aspects of a method of the invention relate to the inhibition of activity of PI3K and/or one or more proteins involved in epigenetic regulation mediated by bromodomain proteins.

In one embodiment the invention provides a method of modulating the PI3K pathway by inhibiting PI3K.

In another embodiment the invention provides a method to modulate epigenetic regulation in a cell mediated by bromodomains (e.g., BET proteins, such as BRD2, BRD3, BRD4, and/or BRDT, and non-BET proteins, such as CBP, ATAD2A, GCN5L, BAZ2B, FALZ, TAF1, and/or BRPF1), by administering a compound as described herein. In some embodiments, the compounds described herein are capable of inhibiting the activity of a bromodomain-containing protein, such as a BET protein (e.g., BRD2, BRD3, BRD4 and/or BRDT), non-BET proteins (e.g., CBP, ATAD2A, GCN5L, BAZ2B, FALZ, TAF1, and/or BRPF1) or a mutant thereof, in a biological sample useful for purposes including, but are not limited to, blood transfusion, organ-transplantation, biological specimen storage, and biological assays.

In some embodiments, the present invention provides a method of inhibiting the activity of a bromodomain-containing protein, such as a BET protein (e.g., BRD2, BRD3, BRD4 and/or BRDT), non-BET proteins (e.g., CBP, ATAD2A, GCN5L, BAZ2B, FALZ, TAF1, and/or BRPF1) or a mutant thereof, in a patient comprising the step of administering to said patient a compound or composition of the invention.

The present invention encompasses methods of treatment comprising administration of a compound(s) of Formula I-IX including methods of treatment of a patient suffering from a condition or disease associated with aberrant kinase activity including PI-3 kinase, or associated with MYC (c-MYC or MYCN) driven disease, or any disease abated by a bromodomain inhibitor. In one aspect, kinase activity may be abnormal, excessive, or constitutively active in a patient in need of such treatment.

The present invention also relates to a method for treating inflammatory disease comprising administering to a patient in need thereof a therapeutically effective amount of compound(s) of Formula I-IX. Exemplary, but non-exclusive diseases and adverse health conditions attributable to kinase activity, in particular inappropriate PI-3 kinase signaling activity, have been disclosed in the art, for example U.S. 2002/0150954A1; U.S. Pat. Nos. 5,504,103; 6,518,277B1; 6,403,588; 6,482,623; 6,518,277; 6,667,300; U.S.20030216389; U.S.20030195211; U.S.20020037276 and U.S. Pat. No. 5,703,075 the contents of which are herein incorporated by reference.

The methods of the invention also include treatment of CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; and attention deficit/hyperactivity disorder (ADHD).

In another aspect, the present invention provides a method for treating Alzheimer's Disease comprising administering to a patient in need thereof a therapeutically effective amount of a compound of Formula I-IX. It has been reported that increasing PIP2 concentrations by, for example, inhibiting PI-3 kinase decreases levels of neurotoxins associated with Alzheimer's Disease (US 2008/0312187; incorporated herein by reference).

In another aspect, the present invention provides a method for enhancing the chemosensitivity of tumor cells comprising administering to a patient in need thereof a therapeutically effective amount of a compound of Formula I-IX.

In another aspect, the present invention provides a method for enhancing the radiosensitivity of tumor cells comprising administering to a patient in need thereof a therapeutically effective amount of a compound of Formula I-IX.

In another aspect, the present invention provides a method for inhibiting or reducing tumor growth comprising administering to a patient in need thereof a therapeutically effective amount of a compound of a compound of Formula I-IX.

In another aspect, the present invention provides a method for inducing oxidative stress in tumor cells comprising administering to a patient in need thereof a therapeutically effective amount of a compound of Formula I-IX.

In another aspect, the present invention provides a method for inhibiting or reducing tumor growth by inhibiting cancer stem cell growth and/or proliferation comprising administering to a patient in need thereof a therapeutically effective amount of a compound of Formula I-IX.

In another aspect, the present invention provides a method for inhibiting tumor induced angiogenesis comprising administering to a patient in need thereof a therapeutically effective amount of a compound of Formula I-IX.

Further, the present invention provides a method for inhibiting angiogenesis associated with non-cancer diseases comprising administering to a patient in need thereof a therapeutically effective amount of a compound of Formula I-IX.

In yet another aspect, the present invention provides a therapeutic method for increasing apoptosis in cancer cells and cancerous tumors comprising administering to a patient in need thereof a therapeutically effective amount of a compound of Formula I-IX.

The present invention also provides a method of treating cancer comprising administering to a patient in need thereof a therapeutically effective amount of a compound of Formula I-IX.

Inhibitory activity can be determined routinely using known methods and also from commercial vendors offering this service for kinases and bromodomain proteins. For example, in vitro kinase inhibition (e.g., PI3K inhibition) can be detected by a standard kinase inhibition assay using labeled ATP to determine if a test compound inhibits the transfer of phosphate from ATP to the kinase substrate. In vivo, PI3K inhibition can be determined from target tissue biopsies by standard tissue processing to disrupt cells and then performing Western Blot analysis to determine the presence or absence of pAKT (substrate of PI3K) relative to a control sample. The activity of a compound of the invention as an inhibitor of a bromodomain-containing protein, such as a BET protein, such as BRD2, BRD3, BRD4, and/or BRDT, or an isoform or mutant thereof, may be determined in vitro, in vivo, or in a cell line. In vitro assays include assays that determine inhibition of bromodomain-containing proteins. Alternatively, inhibitor binding may be determined by running a competition experiment where a provided compound is incubated with a bromodomain-containing protein, such as a BET protein bound to known ligands, labeled or unlabeled. For example, bromodomain inhibition can be determined in vitro using Alpha Screen Technology (http://www.reactionbiology.com/webapps/site/NewsPDFs/Bromodomain%20Assay%20Platform%20for%20Drug%20Screening%20and%20Discovery.pdf). In vivo bromodomain inhibition can be determined indirectly by evaluating the amount of protein present of proteins whose genes' transcription is influenced or controlled by the bromodomain protein, for example, the MYCN protein transcription is controlled by BRD4 (J. E. Delmore et al., *Cell* 2011, 146, 904-917; A. Puissant, *Cancer Discov.* 2013, 3, 308-323).

Bromodomain inhibition may also be predicted by in silico modeling as described below in the Examples.

In certain embodiments, the invention provides a method of treating a disorder (as described above) in a subject, comprising administering to the subject identified as in need thereof, a compound of the invention. The identification of those patients who are in need of treatment for the disorders described herein is within the ability and knowledge of one skilled in the art. Certain of the methods for identification of patients who are at risk of developing the above disorders which can be treated by the subject method are appreciated in the medical arts, such as family history, and the presence of risk factors associated with the development of that disease state in the subject patient.

Assessing the efficacy of a treatment in a patient includes determining the pre-treatment extent of a disorder by methods known in the art (i.e., determining tumor size or screening for tumor markers where the cell proliferative disorder is cancer), then administering a therapeutically effective amount of a compound of the invention, to the patient. After an appropriate period of time after administration (e.g., 1 day, 1 week, 2 weeks, one month, six months), the extent of the disorder is again determined. Modulation (e.g., decrease) of the extent or invasiveness of the disorder (i.e., reduced tumor size) would indicate efficacy of the treatment. The extent or invasiveness of the disorder may be determined periodically throughout treatment. For example, the extent or invasiveness of the disorder may be assessed every few hours, days or weeks to assess the further efficacy of the treatment. A decrease in extent or invasiveness of the disorder indicates that the treatment is efficacious. The methods described may be used to screen or select patients that may benefit from treatment with a compound of the invention.

A variety of cancers may be treated according to the methods of the present invention including, but not limited to: carcinoma of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma. The methods of the invention may also be used to treat accelerated or metastatic cancers of the bladder, pancreatic cancer, prostate cancer, non-small cell lung cancer, colorectal cancer, and breast cancer.

A method of the invention may be administered simultaneously or metronomically with other anti-cancer treatments such as chemotherapy and radiation therapy. The term "simultaneous" or "simultaneously" as used herein, means that the other anti-cancer treatment and the compound of the present invention are administered within 48 hours, preferably 24 hours, more preferably 12 hours, yet more preferably 6 hours, and most preferably 3 hours or less, of each other. The term "metronomically" as used herein means the administration of the compounds at times different from the chemotherapy and at a certain frequency relative to repeat administration and/or the chemotherapy regimen.

The chemotherapy treatment may comprise administration of a cytotoxic agent or cytostatic agent, or combination thereof. Cytotoxic agents prevent cancer cells from multiplying by: (1) interfering with the cell's ability to replicate DNA, and (2) inducing cell death and/or apoptosis in the cancer cells. Cytostatic agents act via modulating, interfering or inhibiting the processes of cellular signal transduction which regulate cell proliferation and sometimes at low continuous levels.

Classes of compounds that may be used as cytotoxic agents include but are not limited to the following: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, and temozolomide; antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxyco-formycin, mitomycin-c, 1-asparaginase, interferons (preferably IFN-.alpha.), etoposide, and teniposide. Other proliferative cytotoxic agents are navelbene, CPT-11, anastrazole, letrazole, capecitabine, reloxafine, cyclophosphamide, ifosamide, and droloxafine.

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see R. F. Service, *Science* 1996, 274, 2009) estramustine, nocodazole, MAP4, and the like. Examples of such agents are also described in J. C. Bulinski et al., *J. Cell Sci.* 1997, 110, 3055-3064; D. Panda et al., *Proc. Natl. Acad. Sci. USA* 1997, 94, 10560-10564; P. F. Mithlradt et al., *Cancer Res.* 1997, 57, 3344-3346; K. C. Nicolaou et al., *Nature* 1997, 387, 268-272; R. J. Vasquez et al., *Mol. Biol. Cell.* 1997, 8, 973-985; and D. Panda et al., *J. Biol. Chem.* 1996, 271, 29807-29812.

Other suitable cytotoxic agents include but are not limited to epidophyllotoxin; an antineoplastic enzyme; a topoisomerase inhibitor; procarbazine; mitoxantrone; platinum coordination complexes such as cis-platin and carboplatin;

biological response modifiers; growth inhibitors; antihormonal therapeutic agents; leucovorin; tegafur; and haematopoietic growth factors.

Cytostatic agents that may be used according to the methods of the invention include, but are not limited to, hormones and steroids (including synthetic analogs): 17 alpha-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, zoladex. Other cytostatic agents are antiangiogenics such as matrix metalloproteinase inhibitors, and other VEGF inhibitors, such as anti-VEGF antibodies and small molecules such as ZD6474 and SU6668 are also included. Anti-Her2 antibodies from Genentech may also be utilized. A suitable EGFR inhibitor is EKB-569 (an irreversible inhibitor). Also included are Imclone antibody C225 immunospecific for the EGFR, and src inhibitors. Also suitable for use as a cytostatic agent is Casodex® (bicalutamide, Astra Zeneca) which renders androgen-dependent carcinomas non-proliferative. Yet another example of a cytostatic agent is the antiestrogen Tamoxifen® which inhibits the proliferation or growth of estrogen dependent breast cancer. Inhibitors of the transduction of cellular proliferative signals are cytostatic agents. Representative examples include but are not limited to epidermal growth factor inhibitors, Her-2 inhibitors, MEK-1 kinase inhibitors, MAPK kinase inhibitors, PI3K inhibitors, Src kinase inhibitors, and PDGF inhibitors.

The present invention also encompasses a method for treating pancreatitis comprising administering to a patient in need thereof a therapeutically effective amount of a compound or compounds of Formula I-IX. As discussed in I. Gukovsky et al., *Gastroenterology* 2004, 126, 554-566, inhibition of PI-3 kinase may prevent pancreatitis.

The present invention also encompasses a method for treating ulcers comprising administering to a patient in need thereof a therapeutically effective amount of a compound of Formula I-IX. The present invention also encompasses a method for treating gastric cancer, such as stomach cancer, comprising administering to a patient in need thereof a therapeutically effective amount of a compound of the present invention. As discussed in Bacon et al., Digestive Disease Week Abstracts and Itinerary Planner, Vol. 2003, Abstract No. M921 (2003) and Rokutan et al., Digestive Disease Week Abstracts and Itinerary Planner, Vol. 2003, Abstract No. 354 (2003), PI-3 kinase is involved in the adhesion of *Helicobacter pylori* to gastric cells.

The present invention also encompasses a method for treating age-related macular degeneration (AMD) comprising administering to a patient in need thereof a therapeutically effective amount of a compound of Formula I-IX. As discussed in M. R. Barakat et al., Expert Opin. Investig. Drugs 2009, 18, 637-646, inhibition of VEGF inhibits blood vessel overgrowth associated with AMD. The methods of the invention may also treat AMD by inhibiting angiogenesis.

The present invention also encompasses a method for treating conditions associated with a mutant PTEN comprising administering to a patient in need thereof a therapeutically effective amount of a compound of Formula I-IX. PTEN is a tumor suppressor gene located on chromosome 10q23, in which mutations have been identified in patients with Cowden disease. As discussed in A. Vega et al., *J. Invest. Dermatol.* 2003, 121, 1356-1359, mutations in PTEN have reduced ability to inhibit the activation of the proto-oncogene AKT. Inhibitors of PI-3 kinase may inhibit phosphorylation of AKT, thereby reducing the deleterious effect of mutant PTEN.

Tat is the human immunodeficiency virus type 1 (HIV-1) trans-activator protein and is known to be tightly regulated by lysine acetylation (R. E. Kiernan et al., *EMBO Journal* 1999, 18, 6106-6118). It is also known that HIV-1 Tat transcriptional activity is absolutely required for productive HIV viral replication (K. T. Jeang et al., *Curr. Top. Microbiol. Immunol.* 1994, 188, 123-144). Thus, the interaction of the acetyl-lysine of the protein Tat with one or more bromodomain-containing proteins (which are associated with chromatin remodeling) could mediate gene transcription allowing viral replication. Blocking bromodomain-containing proteins can thus serve to inhibit HIV viral replication and act as a therapeutic treatment for diseases involving HIV viral replication such as AIDS. The present invention encompasses a method for treating diseases involving HIV viral replication such as but not limited to AIDS comprising administering to a patient in need thereof a therapeutically effective amount of a compound of Formula I-IX. The methods of this invention comprised of administering one or more compounds of Formula I-IX are useful for treating viral infections such as but not limited to human papillomavirus, Herpesvirus, Epstein-Barr virus, human immunodeficiency virus, hepatis B virus, and hepatitis C virus.

In another aspect, the invention provides a method for inhibiting activity of a bromodomain-containing protein in a patient comprising the step of administering to said patient a compound or compounds of Formula I-IX either alone or in combination with other treatment agents.

In another aspect, the invention provides a method for treating bromodomain-containing protein-mediated disorders in a patient in need thereof, comprising administering to said patient a compound of Formula I-IX.

The methods of the invention also include treating a subject with a MYC-dependent cancer, comprising administration of a compound of Formula I-IX. Subjects with MYC-dependent cancer can be determined by several ways including but not limited to determining MYC mRNA expression levels in the tumor and/or MYC protein expression in the tumor. Preferred subjects for treatment with the methods of the invention can be identified by historical experience or known prevalence of MYC activation in certain cancers such as multiple myeloma (J. E. Delmore, Cell 2011, 146, 904-917), CLL (J. R. Brown et al., *Clin. Cancer Res.* 2012, 18, 3791-3802), leukaemia (M. A. Dawson et al., *Nature* 2013, 478, 529-533), neuroblastoma (A. Puissant et al., *Cancer Discov.* 2013, 3, 308-323), or medulloblastoma (Y. J. Cho et al., *J. Clin. Oncol.* 2010, 29, 1424-1430).

Other diseases and conditions treatable according to the methods of this invention include, but are not limited to, other proliferative disorders, sepsis, autoimmune disease, and viral infection. Diseases such as atherosclerosis and type 2 diabetes (V. A. DeWaskin et al., *Nature Rev. Drug Disc.* 2013, 12, 661-662) and obesity and inflammation (A. C. Belkina et al., *Nature Rev. Cancer* 2012, 12, 465-474) are also treatable according to the methods of the invention.

The invention further provides methods for treating or ameliorating cancer or other proliferative disorder by administration of an effective amount of a compound of Formula I-IX to a mammal including a human in need of such treatment. Examples of cancers treatable using an effective amount of a compound of Formula I-IX include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangio sarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

The methods of this invention further include administering one or more compounds of Formula I-IX for treating benign proliferative disorders such as, but are not limited to, meningioma, cerebri, seborrheic keratoses, stomach polyps, thyroid nodules, cystic neoplasms of the pancreas, hemangiomas, multiple endocrine neoplasia, nasal polyps, pituitary tumors, juvenile polyposis syndrome, prolactinoma, pseudotumor benign soft tissue tumors, bone tumors, brain and spinal tumors, eyelid and orbital tumors, granuloma, lipoma, vocal cord nodules, polyps, and cysts, chronic pilonidal disease, dermatofibroma, pilar cyst, pyogenic granuloma, and Castleman disease.

The methods of this invention further comprise administering one or more compounds of Formula I-IX for treating infectious and noninfectious inflammatory events and autoimmune and other inflammatory diseases. Examples of autoimmune and inflammatory diseases, disorders, and syndromes treated using the compounds and methods described herein include but are not limited to: appendicitis, pancreatitis, cholecystitis, agammaglobulinemia, psoriasis, allergy, Crohn's disease, irritable bowel syndrome, ulcerative colitis, inflammatory pelvic disease, urethritis, skin sunburn, sinusitis, pneumonitis, encephalitis, meningitis, myocarditis, nephritis, osteomyelitis, myositis, asthma, allergic rhinitis, chronic obstructive pulmonary disease, autoimmune polyglandular disease/syndrome, autoimmune alopecia, pernicious anemia, glomerulonephritis, dermatomyositis, multiple sclerosis, scleroderma, hepatitis, gastritis, enteritis, dermatitis, gingivitis, Sjogren's disease, tissue graft rejection, hyperacute rejection of transplanted organs, vasculitis, autoimmune hemolytic and thrombocytopenic states, Goodpasture's syndrome, atherosclerosis, Addison's disease, Parkinson's disease, Alzheimer's disease, Type I or 2 diabetes, septic shock, systemic lupus erythematosus, rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Graves' disease, Guillain-Barre syndrome, Behcet's disease, scleracierma, mycosis fungoides, acute respiratory distress syndrome and ischemia/reperfusion injury. In some embodiments, the present invention provides a method of treating systemic inflammatory response syndromes such as LPS-induced endotoxic shock and/or bacteria-induced sepsis by administration of an effective amount of a compound of Formula I-IX to a mammal in need of such treatment.

G. Administration and Dosage

Compounds of Formula I-IX including those disclosed in Table 3 for use in a method of the present invention can be administered in any manner including but not limited to orally, parenterally, sublingually, transdermally, rectally, transmucosally, topically, pulmonarily, nasally, or bucally. Parenteral administration includes but is not limited to intravenous, intraarterial, intraperitoneal, subcutaneous, intramuscular, intrathecal, and intraarticular. Compounds or compositions of the invention may also be administered via slow controlled i.v. infusion or by release from an implant device.

A therapeutically effective amount of a compound of Formula I to IX for use in a method of the invention varies with the nature of the condition being treated, the length of treatment time desired, the age and the condition of the patient, and is ultimately determined by the attending physician. In general, however, doses employed for adult human treatment typically are in the range of 0.001 mg/kg to about 200 mg/kg per day. The dose may be about 1 µg/kg to about 100 µg/kg per day. The desired dose may be conveniently administered in a single dose, or as multiple doses administered at appropriate intervals, for example as two, three, four or more sub-doses per day. Multiple doses often are desired, or required.

A number of factors may lead to the compounds of Formula I-IX being administered according to the methods of the invention over a wide range of dosages. When given in combination with other therapeutic agents, the dosage of the compounds of the present invention may be given at relatively lower dosages. In addition, the use of targeting agents on a conjugate is expected to lower the effective dosage required for treatment. As a result, the daily dosage of a targeted compound administered according to the methods of the present invention may be from about 1 ng/kg to about 100 mg/kg. The dosage of a compound of Formula I-IX according to the methods of the present invention may be at any dosage including, but not limited to, about 1 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, or 100 mg/kg.

The present invention has multiple aspects, illustrated by the following non-limiting examples. The examples are merely illustrative and do not limit the scope of the invention in any way.

Example 1

Several TP Scaffold compounds (structures shown in FIG. 2 and Table 3) were tested for inhibition activity against isoforms of PI3K (alpha, beta, gamma, and delta isoforms) and the bromodomain protein BRD4 at regions 1 (BRD4-1) and 2 (BRD4-2). The results are shown in Table 1.

TABLE 1

BRD4 and PI3K inhibitor data.

| Compd ID | BRD4-1 IC$_{50}$ (nM) | BRD4-2 IC$_{50}$ (nM) | PI3Kα IC$_{50}$ (nM) | PI3Kβ IC$_{50}$ (nM) | PI3Kδ IC$_{50}$ (nM) | PI3Kγ IC$_{50}$ (nM) |
|---|---|---|---|---|---|---|
| LY294002 | 5330 | 13,100 | 356 | 736 | 3224 | 1060 |
| JQ-1 | 27.1 | 39.1 | >50,000 | NA | >50,000 | >50,000 |
| 28 | 241 | 1547 | 34 | 214 | 960 | 158 |
| 44 | 811 | 1469 | 400 | 3600 | 12 | 547 |
| 118 | 193 | 235 | 90 | NA | 53 | 806 |
| 120 | 326 | 393 | 95 | NA | 21 | 556 |
| 25 | 277 | 628 | 714 | 1750 | 27 | 1170 |
| 121 | 255 | 2,310 | <10,000 | NA | NA | NA |
| 100 | 1,094 | 2,755 | 55.2 | NA | 295 | 259 |
| 122 | 2,568 | 4,879 | 950 | NA | 1350 | 8650 |
| 123 | >50,000 | >50,000 | 7670 | NA | 9750 | >16700 |
| 124 | 519 | 2,795 | 1580 | NA | 480 | 4630 |
| 125 | 1,012 | 1,872 | 29,100 | NA | 2490 | >50000 |
| 126 | >>50,000 | >>50,000 | 889 | NA | 1480 | 2200 |
| 127 | 32,650 | 34,190 | 1720 | NA | 3300 | 9770 |
| 10 | >>50,000 | >>50,000 | 7158 | 9247 | >50,000 | >50,000 |
| 6 | 2169 | 3451 | 297 | 378 | 784 | 1570 |
| 128 | 4002 | 10740 | NA | NA | NA | NA |
| 129 | 2229 | 9411 | NA | NA | NA | NA |
| 130 | 349 | 695 | NA | NA | NA | NA |
| 131 | 231 | 446 | NA | NA | NA | NA |
| 132 | 5482 | 11640 | NA | NA | NA | NA |
| 133 | 558 | 1116 | NA | NA | NA | NA |
| 134 | 662 | 1850 | NA | NA | NA | NA |
| 135 | 646 | 1272 | NA | NA | NA | NA |
| 136 | 6150 | 1256 | NA | NA | NA | NA |
| 137 | 748 | 1256 | NA | NA | NA | NA |
| 11 | 843 | 1742 | 154 | NA | 9807 | 6300 |

(NA = data not yet available)

All thienopyranone-based compounds tested inhibited either PI3K or BRD4 or both PI3K and BRD4. The two clinical stage PI3K inhibitors CAL101/GS1101 and BKM120 showed no BRD4 inhibition in this assay. Both pan- and delta isoform selective thienopyranone-based PI-3K inhibitors (Cmpd 28 and Cmpd 44, respectively) showed activity against BRD4 regions 1 and 2. JQ1+, a known bromodomain inhibitor, was used as reference compound. JQ1+ does not inhibit PI3K.

Example 2

To test the effect of combining a PI3K inhibitor of the invention with a known BET inhibitor, cytotoxicity of Cmpd 28 and JQ1+, alone and in combination was determined in murine cell line NB9464, a human neuroblastoma cell line (SKNBE(2)) (both of which possess MYC amplification), and MYCN-dependent MB patient derived xenograft (PDX) cell line passaged in NOD scid gamma−/− mice). The results of this proliferation study are shown in Table 2.

TABLE 2

Synergistic activity of PI3K inhibitor Cmpd 28 plus BET inhibitor JQ1+

| Cell Line | Cmpd 28 | JQ1(+) | Cmpd 28 plus JQ1(+) | Fold increase IC50 (µM) |
|---|---|---|---|---|
| SKNBE(2) | 7.6 | 1.9 | 0.267 | 7.1 |
| NB9464 | 8.7 | 1.6 | 0.352 | 4.5 |
| PDX MB | 3.6 | 2.2 | 0.46 | 4.8 |

The data presented in Table 2 showed a 5-to-7 fold enhancement effect with the combination of Cmpd 28 and JQ1+ in inhibiting proliferation demonstrating a marked synergy in combining a PI3K pathway inhibitor with a BRD4 inhibitor. These data further show that dual inhibition of PI3K and BET augments cytotoxicity in MYCN cells.

Example 3

Figure 3:
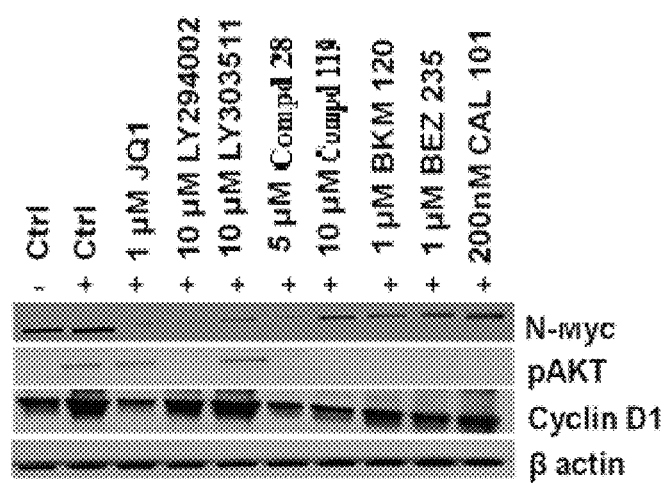
FIG. 3 shows a Western blot analysis of the effects of inhibitors on expression of P-AKT, N-MYC, and Cyclin D1, and β-actin in SKNBE(2) cells.

The thienopyranone (TP)-based PI-3K inhibitor Cmpd 28 induced marked degradation of MYCN in addition to inhibiting pAKT using Western Blot probing experiments (See FIG. 3). SKNBE (2) cells (A) were serum starved for 4 hrs followed by treatment with JQ1, LY294002, LY303511, SF2523, SF1126, BKM 120, BEZ 235 and CAL101 at concentrations indicated for 24 hrs. Cells were stimulated with 50 ng/ml IGF for 30 min and used for lysate preparation. Proteins were quantitated by the BCA protein assay (Pierce). Equal amounts of protein were resolved by polyacrylamide gels, transferred to nitrocellulose membrane and probed by Western blot with the following primary antibodies: p-AKT(Ser473), AKT (Cell Signaling Technologies), N-MYC, CyclinD1 and β-actin (Santa Cruz Biotechnology). The results showed that pure BRD4 inhibitors JQ1 and LY303511 inhibited only MYCN quantities; pure PI-3K inhibitors CAL101, BEZ235, BKM120 decreased pAKT; while dual BRD4/PI-3K inhibitors Cmpd 28 and LY294002 decreased MYCN and pAKT demonstrating that both pathways are inhibited by a single dual inhibition molecule.

Example 4

Figure 4:
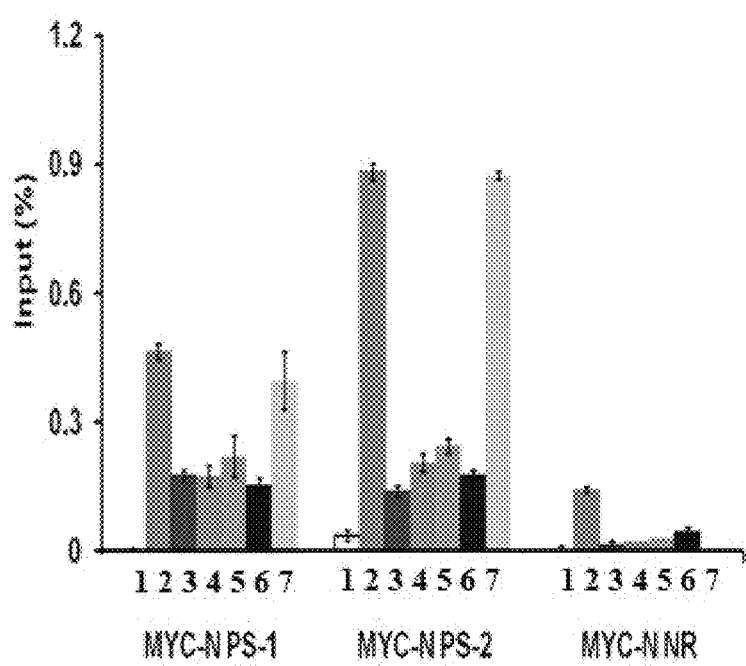
FIG. 4 shows the results of analysis of MYCN gene expression by PCR analysis at two sites in the MYCN promoter region (NPS-1 and NPS-2) and in a gene desert region (MYC-N NR) in SKNBE(2) cells after exposure to: Lane 1—negative control, Lane 2—positive control, Lane 3—1 µM JQ-1, Lane 4—15 µM LY294002, Lane 5—15 µM LY303511, Lane 6—2 µM Cmpd 28, Lane 7—1 µM CAL-101.

MYCN amplified SKNBE(2) cells were exposed to inhibitors for 24 hours then chromatin was precipitated with Brd4 (rabbit polyclonal antibody) along with rabbit IgG as a negative control (IgG). Precipitated chromatin was analyzed for the MYCN gene (2 sites within the MYCN promoter region) by quantitative PCR and enrichment is shown as the percentage of total input DNA (FIG. 4). The negative control region primers amplify within a gene desert region approximately 1 Mb away from MYCN (MYC-N NR). Error bars represent±SEM of triplicate data. P<0.05 as compared to positive control (paired t-test). Positive control: No inhibitor; IP with BRD4 antibody, Negative Control: No inhibitor, IP with rabbit IgG These data show that all BRD4 inhibitors (pure BRD4 inhibitors JQ-1, LY202511 and dual BRD4/PI-3K inhibitors LY294002, Cmpd 28) significantly repressed MYCN expression whereas the pure PI-3K delta inhibitor CAL-101 did not supporting the conclusion that BRD4 inhibition blocks MYCN expression.

Example 5

Figure 5:
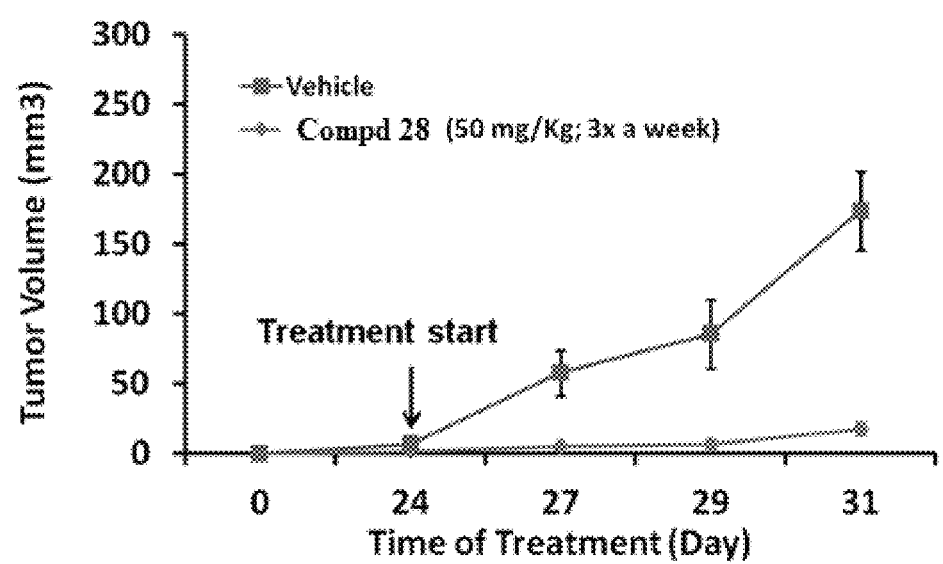
FIG. 5 shows the effect of Cmpd 28 on NB9464 tumor growth in nude mice.

MYCN-overexpressing murine neuroblastoma cells (NB9464) were transplanted into nude mice, grown for 24 days and randomized into two groups. Group 1 were treated with vehicle (DMSO) and group 2 were treated with SF2523 (50 mg/kg), 3 days a week for 1.5 weeks via intra-peritoneal injections. The results (FIG. 5) demonstrate that dual PI-3K/BRD4 inhibitor Cmpd 28 treatment was well tolerated (no body weight loss, data not shown) and significantly blocked tumor growth compared to vehicle.

Example 6

Figure 6A:
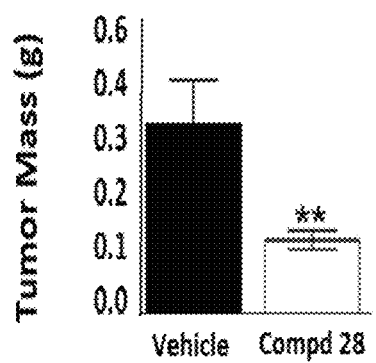
FIG. 6A shows the effect of Cmpd 28 on metastatic tumor mass in nude mice transplanted with Panc02 pancreatic tumor cells.
Figure 6B:
FIG. 6B shows images of pancreatic tumors isolated from Cmpd 28-treated and untreated animals of FIG. 6A.
Figure 6C:
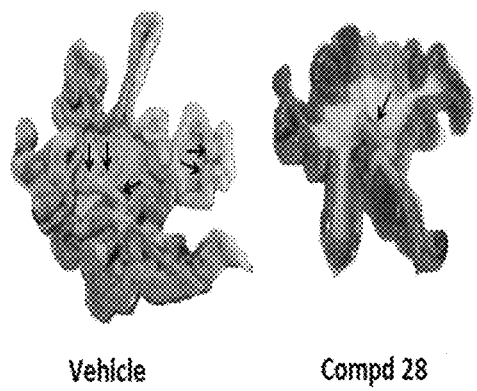
FIG. 6C shows images of Panc02 metastatic mesenteric lymph nodes of WT mice treated with vehicle or Cmpd 28.
Figure 6D:
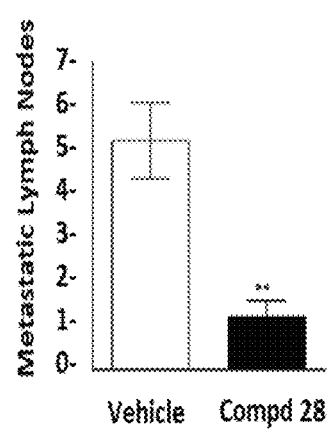
FIG. 6D shows the number of lymph nodes effected by Panc02 metastatic mesenteric lymph node tumors in mice treated with Cmpd 28.

The dual PI3K/BRD4 inhibitor SF2523 blocks spontaneous metastasis in an orthotopic pancreatic model. Panc02 ($1 \times 10^6$) tumor cells were injected into the pancreas of WT mice (n=18). After 20 days, mice were randomized into two groups. One group was treated with DMSO (control) and the other group was treated with 50 mg/kg of SF2523, three times a week. Tumors were removed 35 days after tumor implantation. The results are shown in FIGS. 6A-6D. Values are mean±SEM (n=8 in each gp; P<0.01; pair wise two-sided Student's t test). These results demonstrate that Cmpd 28 blocks spontaneous metastasis in this orthotopic pancreatic model. FIG. 6A shows tumor mass differences; FIG. 6B shows representative images of pancreatic tumors isolated from the pancreas of WT mice treated with DMSO or 50 mg/kg Cmpd 28. FIG. 6C shows macroscopic view of Panc02 metastatic mesenteric lymph nodes (arrows) from WT mice treated with DMSO or 50 mg/kg Cmpd 28. FIG. 6D shows the number of metastatic mesenteric lymph nodes/mesentery. Values are mean±SEM (n=7; P<0.01; pair wise two-sided Student's t test). The data are representative of three independent experiments performed.

Example 7

Figure 7A:
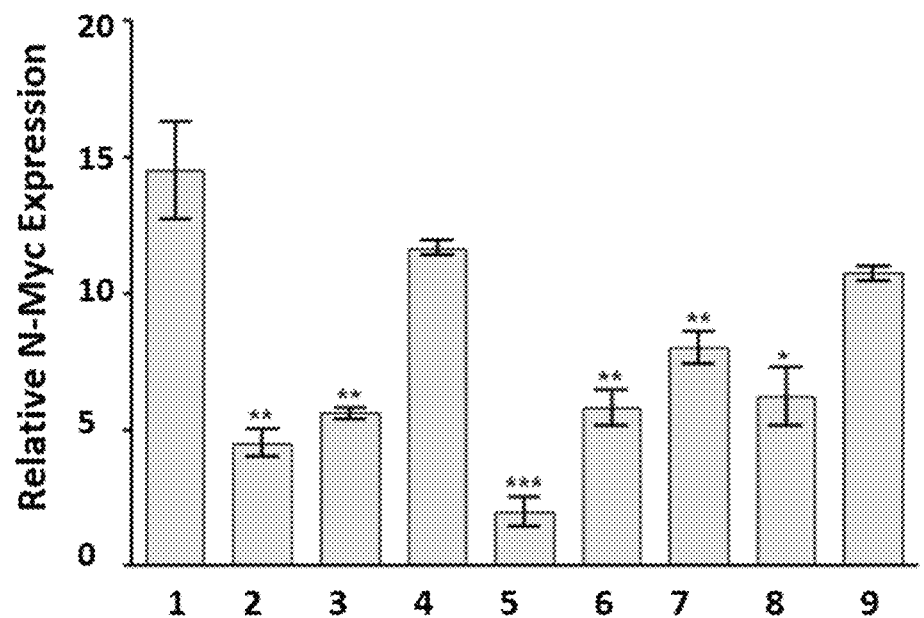
FIG. 7A shows the effects of various PI3K and BET bromodomain inhibitors on the expression of N-myc mRNA in SKNBE(2) cells. Lane 1—control, Lane 2—1 µM JQ-1, Lane 3—10 µM LY294002, Lane 4—10 µM LY303511, Lane 5—5 µM Cmpd 28, Lane 6—10 µM Cmpd 119, Lane 7—1 µM BKM 120, Lane 8—1 µM BEZ 235, Lane 9—200 nM CAL 101.
Figure 7B:
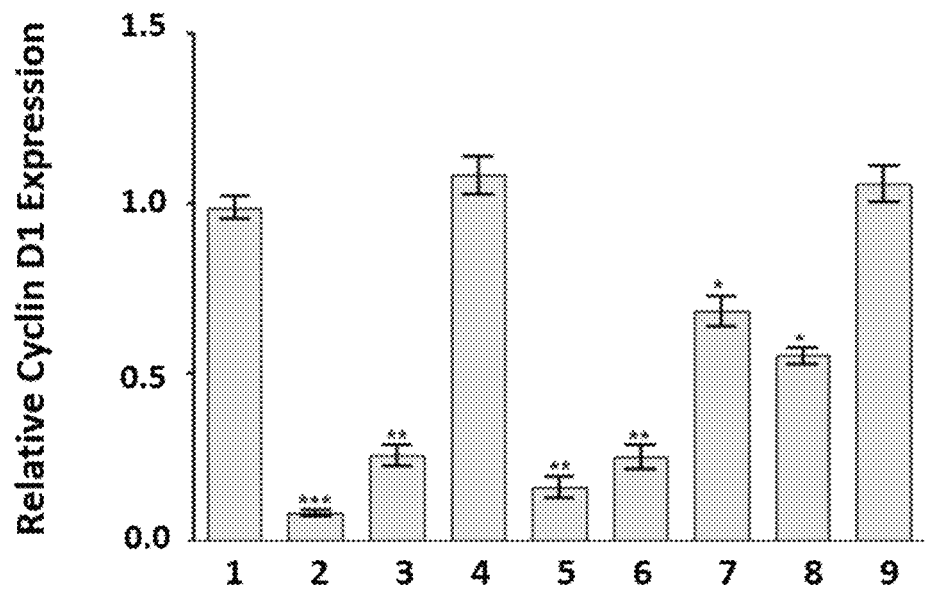
FIG. 7B shows the effects of various PI3K and BET bromodomain inhibitors on the expression of N—myc target Cyclin D1 mRNA in SKNBE(2) cells. Lane 1—control, Lane 2—1 µM JQ-1, Lane 3—10 µM LY294002, Lane 4—10 µM LY303511, Lane 5—5 µM Cmpd 28, Lane 6—10 µM Cmpd 119, Lane 7—1 µM BKM 120, Lane 8—1 µM BEZ 235, Lane 9—200 nM CAL 101.

Messenger RNA expression of N-myc (MYCN) and its target Cyclin D1 was examined by exposure to the dual PI3K/BRD4 inhibitor Cmpd 28 using real-time PCR. SKNBE(2) cells were serum starved for 4 hrs followed by treatment with 1 µM JQ1, 10 µM LY294002, 10 µM LY303511, 5 µM Cmpd 28, 10 µM Cmpd 119, 1 µM BKM 120, 1 µM BEZ 235 and 200 nM CAL101 for 24 hrs. Cells were stimulated with 50 ng/ml IGF and used for RNA isolation after 24 hrs of treatment with various inhibitors. The results for N-Myc are shown in FIG. 7A and for Cyclin D1 in FIG. 7B. FIG. 7A shows the effects of various PI3K and BET bromodomain inhibitors on the expression of N-myc mRNA in SKNBE(2) cells. Lane 1—control, Lane 2—1 µM JQ-1, Lane 3—10 LY294002, Lane 4—10 µM LY303511, Lane 5—5 µM Cmpd 28, Lane 6—10 µM Cmpd 119, Lane 7—1 µM BKM 120, Lane 8—1 µM BEZ 235, Lane 9—200 nM CAL 101. FIG. 7B shows the effects of various PI3K and BET bromodomain inhibitors on the expression of N-myc target Cyclin D1 mRNA in SKNBE(2) cells. Lane 1—control, Lane 2—1 µM JQ-1, Lane 3—10 µM LY294002, Lane 4—10 µM LY303511, Lane 5—5 µM Cmpd 28, Lane 6—10 µM Cmpd 119, Lane 7—1 µM BKM 120, Lane 8—1 µM BEZ 235, Lane 9—200 nM CAL 101.

Example 8

Figure 8A:
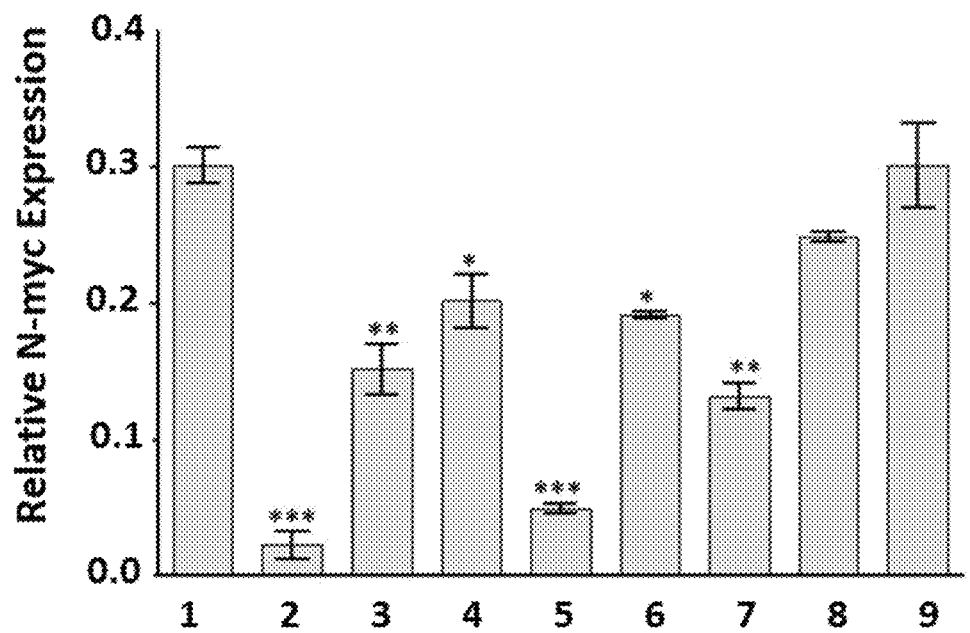
FIG. 8A shows the effects of various PI3K and BET bromodomain inhibitors on the expression of N-myc mRNA in IMR32 cells. Lane 1—control, Lane 2—1 µM JQ-1, Lane 3—10 µM LY294002, Lane 4—10 µM LY303511, Lane 5—5 µM Cmpd 28, Lane 6—10 µM Cmpd 119, Lane 7—1 µM BKM 120, Lane 8—1 µM BEZ 235, Lane 9—200 nM CAL 101.
Figure 8B:
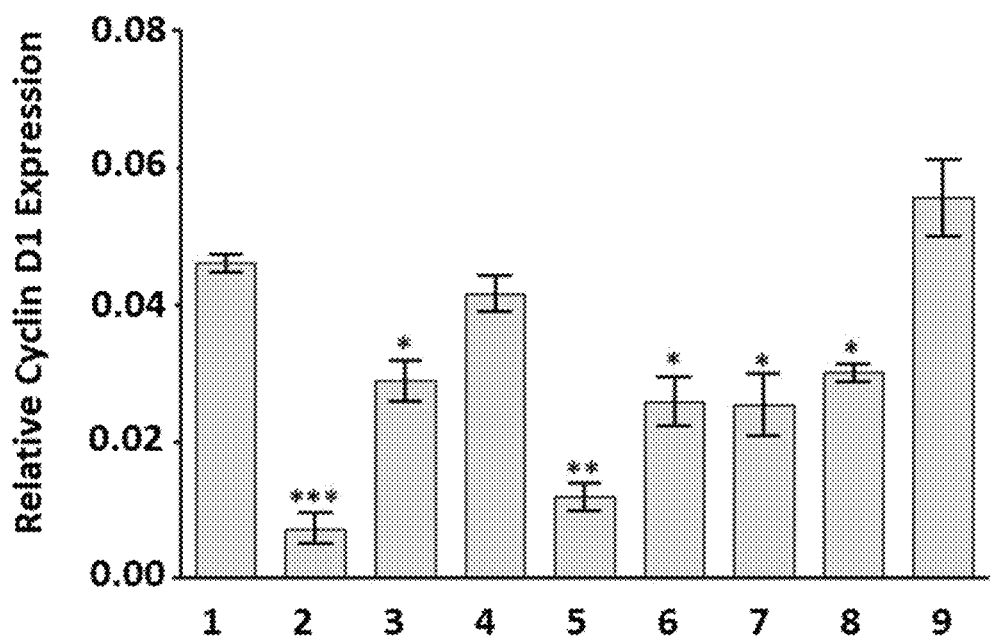
FIG. 8B shows the effects of various PI3K and BET bromodomain inhibitors on the expression of N-myc target Cyclin D1 mRNA in IMR32 cells. Lane 1—control, Lane 2—1 µM JQ-1, Lane 3—10 µM LY294002, Lane 4—10 µM LY303511, Lane 5—5 µM Cmpd 28, Lane 6—10 µM Cmpd 119, Lane 7—1 µM BKM 120, Lane 8—1 µM BEZ 235, Lane 9—200 nM CAL 101.

The experiment of Example 7 was repeated in the IMR32 cell line (MYCN amplified neuroblastoma cancer cell line). The results, shown in FIGS. 8A-8B demonstrate that the dual PI3K/BRD4 inhibitor Cmpd 28 inhibits MYCN expression and its gene expression target Cyclin D1 by reducing mRNA expression. FIG. 8A shows the effects of various PI3K and BET bromodomain inhibitors on the expression of N-myc mRNA in IMR32 cells. Lane 1—control, Lane 2—1 µM JQ-1, Lane 3—10 µM LY294002, Lane 4—10 µM LY303511, Lane 5—5 µM Cmpd 28, Lane 6—10 µM Cmpd 119, Lane 7—1 µM BKM 120, Lane 8—1 µM BEZ 235, Lane 9—200 nM CAL 101. FIG. 8B shows the effects of various PI3K and BET bromodomain inhibitors on the expression of N—myc target Cyclin D1 mRNA in IMR32 cells. Lane 1—control, Lane 2—1 µM JQ-1, Lane 3—10 µM LY294002, Lane 4—10 µM LY303511, Lane 5—5 µM Cmpd 28, Lane 6—10 Cmpd 119, Lane 7—1 µM BKM 120, Lane 8—1 µM BEZ 235, Lane 9—200 nM CAL 101.

Example 9

Figure 9:
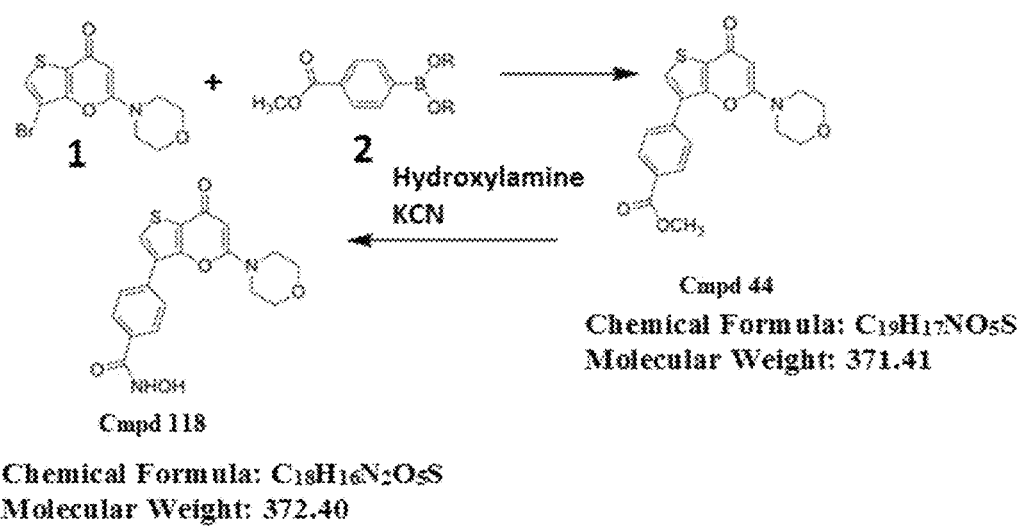
FIG. 9 provides a synthetic scheme for the preparation of Cmpd 118, a dual PI3K/BRD4 inhibitor.

Preparation of kinase/epigenetic inhibitor Cmpd 118 an HDAC/PI3K/BRD4 inhibitor. Cmpd 118 which has a hydroxamic acid moiety was synthesized according to the methods of U.S. Pat. No. 8,557,807 herein incorporated by reference. Hydroxamic acid imparts HDAC inhibiting properties while maintaining the ability to inhibit PI3K and BRD4. Synthesis of Cmpd 118 was accomplished as described below and as depicted schematically in FIG. 9. Methyl 4-(5-morpholino-7-oxo-7H-thieno[3,2-b]pyran-3-yl)benzoate (Cmpd 44) was prepared from the bromo compound 1 using 4-methoxycarbonylphenylboronic acid 2. A 20-mL microwave vial was charged with a magnetic stirring bar, 3-bromo-5-morpholino-7H-thieno[3,2-b]pyran-7-one (1) (1 g, 3.2 mmol), 4-methoxycarbonylphenyllboronic acid (860 mg, 4.8 mmol), cesium carbonate (2.06 g, 6.4 mmol), dichloro[1,bis(diphenylphosphino)ferrocene]palladium(II) dichloromethane adduct (180 mg, 0.16 mmol), and dimethoxyethane (15 mL). The reaction mixture was magnetically stirred and heated via microwave irradiation for 15 minutes at 180° C. Upon cooling to room temperature, the reaction was concentrated in vacuo and purified using high-pressure liquid chromatography to give methyl 4-(5-morpholino-7-oxo-7H-thieno[3,2-b]pyran-3-yl)benzoate (SF2558). Using the HPLC conditions below this compound was found to have a retention time of 4.6 minutes and showed a mass signal of 373.1 corresponding to the M+1 ion.

Conversion of Cmpd 44 to Cmpd 118.

This modified procedure was adapted from *J. Org. Chem.* 2005, 70, 4873-4875. Reaction solvent was prepared by combining THF/CH$_3$OH/50% NH$_2$OH in a ratio of (1:1:0.5). SF-2558 (1 g, 2.7 mmol) was then dissolved in the reaction solvent (20 mL) and the reaction mixture stirred at 35° C. for 24 hours. The crude reaction mixture was then freeze dried and the brown residue stirred in acetonitrile and filtered to recover a solid. The isolated solid was then dissolved in water and purified by prep HPLC. After freeze drying SF2558HA was isolated as a white solid (180 mg, 18%) identified by the analytical HPLC conditions below to have a retention time of 7.3 minutes and showed a mass signal of 372.1 corresponding to the M+1 ion.

Analytical HPLC Conditions:

A Pinnacle C-18 reverse phase column with 3µ packing size was used; acetonitrile (A) and water (B) were used as solvents, both containing 0.1% TFA and a gradient of 5% A initially ramping to 95% A solvent over 10 minutes at a flow rate of 1 mL/min monitoring by UV at a wavelength of 225 nm.

Figure 10:
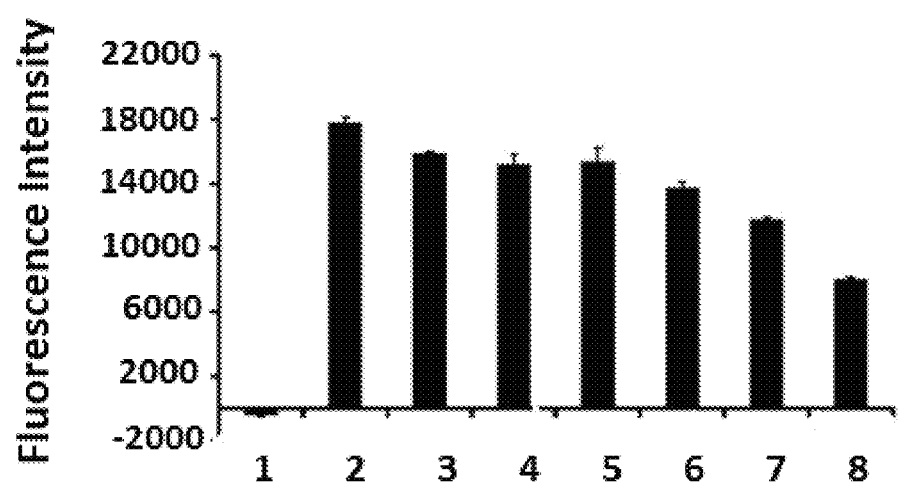
FIG. 10 shows HDAC inhibition activity by Cmpd 44 and Cmpd 118. Lane 1—inhibitor control, Lane 2—positive control, Lane 3—Cmpd 44, 1 µM, Lane 4—Cmpd 44, 10 µM, Lane 5—Cmpd 44, 50 µM, Lane 6—Cmpd 118, 1 µM, Lane 7—Cmpd 118, 10 µM, Lane 8—Cmpd 118, 50 µM.

Enzymatic Inhibitory Activity of Cmpd 118:

A commercially available kit was used to measure HDAC inhibitory activity of Cmpd 44 and Cmpd 118. The results are shown in FIG. 10. No inhibitor activity was observed for the methyl ester Cmpd 44 (lanes 3-5) but significant HDAC inhibitory activity was observed for Cmpd 118 (lanes 6-8). Cmpd 118 showed a concentration dependent effect on HDAC inhibition such that at 1 µM (lane 6), 10 µM (lane 7), and 50 µM (lane 8) the compound inhibited HDAC activity 17%, 25%, and 41%, respectively, versus control (lane 2). Cmpd 118 was also determined to inhibit PI3K (alpha isoform) 76%, delta PI3K isoform 80%, and the PI3K gamma isoform 30% at 300 nM concentration. Cmpd 44 showed 53% 81%, and 26%, respectively, for the three PI3K isoforms.

Additionally, as described in Example 1 and Table 1, Cmpd 118 potently inhibited BRD4-1 (domain 1) and BRD4-2 (domain 2) with an IC$_{50}$ value of 193 nM and 235 nM respectively. These results demonstrate an aspect of the invention, namely potent PI3K and BRD4 inhibition activity by a single molecule.

Example 10

In-silico Modeling of Compounds of Formula I Show BRD4 Binding. Computational modeling was performed using the commercially available FlexX (http://www.biosolveit.de/FlexX/download/flexx_brochure.pdf) software tools. FlexX was used to dock in silico the compounds of the invention (Formulas I) at the site where the LY294002 compound has been described to reside in BRD4-BD1 (bromodomain 1 of BRD4) which has been described in the crystal structure (A. Dittmann et al., *ACS Chem. Biol.* 2014, 9, 495-502). As proof of concept, we docked LY294002 at the same BRD4-BD1 binding site found in the crystal structure of LY294002/BRD4(BR1) and confirmed that the docked LY294002 conformation overlays almost perfectly with the co-crystallized LY294002. The docking results of the compounds of the invention with the empty crystal structure of BRD4 (co-crystallized LY294002 removed) are shown (along with structures of the compounds of the invention) in Table 3 along with the docking score (binding energy) given as delta-G (enthalpy, kcal/mol). It should be noted that the more negative the number or value of the docking score is, the stronger is the predicted binding energy at the BRD4 site that recognizes the acetyl lysine of chromatin. We assayed CAL101, a known PI3K inhibitor (selective for the delta isoform) and the only FDA-approved PI3K inhibitor, and showed no significant BRD4 inhibition (>50, 000 nM). The in silico model showed that CAL101 could not bind to the BRD4-BD1 acetyl-lysine site confirming the observed assay results providing further support for the value of the in silico model for predicting binding potentials of the compounds of the invention with the BRD4 protein structure. It should be noted that in this model LY294002 gives a binding value of −22.61. In Tables 3 an entry of ND indicates that the molecular modeling with FlexX was not performed and, consequently, there is no available data to include in the table. Taken together, the results of Table 1 (PI3K inhibition) with the BRD4 binding data (Tables 1 and 3) demonstrate that compounds of Formula I are inhibitors of PI3K, or inhibitors of bromodomains (illustrated by BRD4 inhibition), or dual inhibitors of both PI3K and bromodomains such as BRD4.

Example 11

Figure 11:
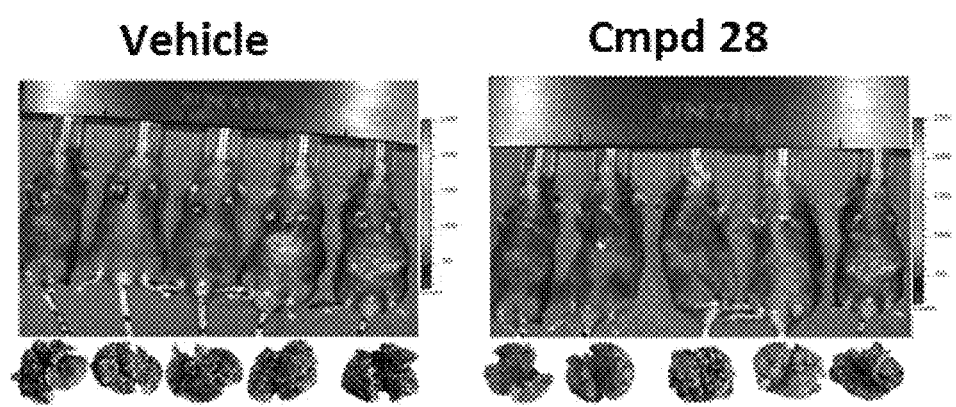
FIG. 11 shows IVIS imaging of mice injected with B16 melanoma cells, untreated (left panel) and treated (right panel) with Cmpd 28; Color Box: min 153-max 2526; Image: min −46-max 3052.

A mouse model of metastasis was used to demonstrate that compounds of Formula I-IX are useful in preventing metastasis of melanoma cells. B16 melanoma cells were injected into WT mice and then treated with or without Cmpd 28 (n=5). B16 F10 luciferase cells (5×10$^5$ cells) were injected through the tail vein, and 50 mg/kg Cmpd 28 was administered every other day until the lungs were removed after 15 days. The luciferase signal was monitored every third day by injecting luciferin, until the lungs were harvested on day 15 (n=5). The results of this experiment are shown in FIG. 11. Bioimaging shows the luciferase signal (blue color) generated by the cancer cells illustrating large areas of tumor growth in the control animals particularly in the lungs (left panel) whereas mice treated with a compound of Formula I (Cmpd 28) show little evidence of the presence of cancer cells. Lungs extracted from these animals are shown below the luciferase imaged pictures supporting the repression of tumor growth in Cmpd 28-treated mice. A 60% (p<0.01) reduction in metastatic nodules was observed in Cmpd 28-treated mice. These results demonstrate that SF2523, a compound of Formula I, blocks spontaneous tumor progression and lymph node metastasis in vivo.

Example 12

Biological testing of compounds of Formula I. Representative compounds of the invention were tested for cellular PI3K inhibitory activity (as measured by the most robust marker of pathway activity pAKT) in a prostate cancer cell line (PC3), which is summarized in Table 3. The concentration needed to inhibit 50% of the pAKT signal (Table 3 PC3 pAKT IC$_{50}$) was determined as follows: PC3 cells were obtained from the American Type Culture Collection (ATCC, Manassas, Va., Cat.#CRL-1435). Two million cells from the prostate cancer line PC3 were placed into 6 cm culture dishes and allowed to grow in complete RPMI 1640 media (Invitrogen, Carlsbad, Calif., Cat.#22400-105) with 10% fetal bovine serum (Invitrogen, Carlsbad, Calif., Cat.#10438-026). After this time period the cells were serum starved for 5 hours followed by application of the test compound. Test compound was added as a DMSO (dimethyl sulfoxide) solution such that the final DMSO concentration in the cell media was less than or equal to 0.2% by volume. After 30 minutes of exposure the growth factor stimulant, human IGF-1 (PeproTech, Inc., Rocky Hill, N.J., Cat.#100-11), was added in each well. After 30 minutes of IGF-1 exposure, cells were removed from the media and cell lysates were prepared using RIPA Lysis buffer (Upstate, Lake Placid, N.Y., Cat.#20-188), keeping on ice. The pAKT serine 473 level was measured in duplicate samples of the cell lysates using commercially available assays such as the Pathscan® Sandwich ELISA kit for Ser473 pAKT (Cell Signaling, Danvers, Mass., Cat.#7160). A SpectraMax Plus spectrophotometric plate reader (Molecular Devices, Sunnydale, Calif.) was used to measure the optical density signal for pAKT at 450 nm (OD450 nm). The pAKT OD450 nm readings were normalized by total protein amount in the cell lysates determined by standard methods. Concentrations of test compounds required to inhibit IGF stimulated pAKT levels to 50% of maximum levels in PC3 cells (termed IC$_{50}$ in Table 3) were calculated by inputting the dose responses in the software package GraphPad Prism4 (GraphPad Software, Inc., San Diego, Calif.).

Example 13. Conversion of Compounds from Carbonyl (M=O) to Thiocarbonyl (Thione, M=S)

A 2-mL conical microwave vial is charged with a magnetic stirring bar, 488 µmol of carbonyl containing compound of Formula I (M=O), Lawesson's reagent (118 mg, 293 µmol), and toluene (2 mL). The reaction mixture is sealed, and the reaction mixture is magnetically stirred and is heated via microwave irradiation at 130° C. for 20 min. The final mixture is poured onto water (approximately 30 mL) and is extracted with dichloromethane (3×5 mL). The combined extracts is dried over anhydrous magnesium sulfate, is filtered, and is concentrated to dryness. The crude reaction mixture is then purified via column chromatography. Elution of the silica gel column is performed with a mix of hexanes/ethyl acetate (1:1). Elution is continued with 100% ethyl acetate to afforded pure thione (Formula I, M=S).

Example 14. Synthesis of Compound 127

N-Acetylthiomorpholine: To a cold solution (−20° C.) of thiomorpholine (9.1 g., 88.2 mmol) and N,N-diisopropylethylamine (22.8 g., 176.4 mmol) in toluene (270.00 mL) was added acetyl chloride (7.34 g., 93.5 mmol) slowly over 30 min. The resulting mixture was stirred at the same temperature for one more hour and then allowed to warm to room temperature. The mixture was stirred for one hour at room temperature. The reaction mixture was diluted with ethyl acetate (200 mL), washed with water, dried (Na2SO4), filtered and concentrated to yield the desired product as a brown oil (10.6 g., 82.7%), which was used in the next step without further purification. TLC (Silica gel plate, 5% MeOH in DCM), single spot, Rf=0.24 (Visualization: PMA stain). The proton NMR was consistent with the expected structure. 1-(4-Bromo-3-hydroxythiophen-2-yl)-3-thiomorpholinopropane: Commercially available methyl-4-bromo-3-hydroxythiophene-2-carboxylate (4.031 g., 17.0 mmol) and N-acetyl thiomorpholine (2.716 g., 18.7 mmol) were dissolved in anhydrous THF (170 mL) and the solution was cooled to 0° C. under nitrogen and stirring. Lithium hexamethyldisilazide (59.5 mL of a 1.0 M solution in THF, 59.5 mmol) was added dropwise during 35 min at 00 C. The reaction mixture was stirred an additional hour at 0° C. and then at room temperature overnight. The reaction mixture was poured into ice cold solution of 1M HCl aqueous (60 mL) very slowly over 30 minutes. Then it was extracted with dichloromethane (2×500 mL), dried (Na2SO4), filtered and concentrated to yield the desired yellow colored solid, crude diol (6.8 g). The crude material was crystallized with boiling acetone (135 mL) to yield light yellow crystals (2.63 g, 44.5%). LC/MS, Peak at 352.1-354.2 (M+1), retention time 4.00 min. TLC (Silica gel plate, 1:1:acetone:hexane), single spot, Rf=0.69. The proton NMR was consistent with the expected structure.
Compound 127 (3-Bromo-5-thiomorpholino-7H-thieno[3,2-b]pyran-7-one): 1-(4-Bromo-3-hydroxythiophen-2-yl)-3-thiomorpholinopropane (2.00 g., 5.71 mmol) from the previous step was dissolved into dichloromethane (45.00 mL) under stirring and nitrogen and cooled to 0° C. Then trifluoromethane sulfonic anhydride (2.43 g., 8.6 mmol) was added dropwise over 30 minutes at 0° C. Then the reaction mixture was stirred at 0° C. for one more hour and then at room temperature for four hours. The reaction was again cooled to 0° C. and treated with MeOH (3.00 mL), the stirred vigorously at 0° C. for 30 more minutes and solvents were removed at 35° C. The tan colored oily residue was dissolved into boiling acetone (20.00 mL) and added hexane (10.00 mL). The mixture was cooled at 0° C. under stirring for 40 minutes which yielded tan colored crystals. The solids were filtered and dried to yield the crude product-Compound 127 (1.35 g., 70%). LC/MS, Peak at 334.3-337.1 (M+1), retention time 4.15 min and 351.9-349.7 (M+1), retention time 4.12 min (starting material diol). TLC on silica gel plate (1:1 Acetone:Hexane), two spots Rf=0.56 of diol and Rf=0.42 of product. Product spot is fluorescent blue (UV). A pure sample of product compound 127 was obtained by preparative TLC plate, eluting with 1:1 hexane/acetone. The proton NMR was consistent with the expected structure.

Example 15. Synthesis of Compound 124

3-(2,3-Dihydrobenzo[b][1.4]dioxan-6-yl)-5-thiomorpholino-7H-thieno[3,2-b]pyran-7-one (compound 124)

3-Bromo-5-thiomorpholino-7H-thieno[3,2-b]pyran-7-one (compound 127) (116.0 mg, 0.35 mmol) prepared as in Example 14, 1,4-benzodioxane-6-boronic acid (94.0 mg, 0.52 mmol) and Pd[Ph3P]4 (22.0 mg., 0.0175 mmol) were taken into a mixture of 2M Na2CO3 (aq) (1.2 mL), toluene (2.8 mL) and EtOH (1.4 mL). The whole mixture was stirred under nitrogen at 90° C. for 1.5 hrs. Then it was cooled and diluted with ethyl acetate (50.0 mL), washed with water and concentrated in vacuo. The crude residue was dissolved into dichloromethane and purified on silica preparative TLC plate (ethyl acetate as the eluent). The extraction of silica yielded final pure compound 124 (37.0 mg., 27.3%). LC/MS, Peak at 3.00 minutes m=388.5-391.4 (M+1). Purity is 99%. The proton NMR was consistent with the expected structure.

Example 16. Synthesis of Compound 125

4-Ethoxycarbonyl phenyl-5-thiomorpholino-7H-thieno[3,2-b]pyran-7-one (compound 125)

This compound was synthesized in the similar fashion as Example 15 above. 3-Bromo-5-thiomorpholino-7H-thieno[3,2-b]pyran-7-one (compound 127) (116.0 mg., 0.35 mmol), 4-ethoxycarbonyl phenyl boronic acid (102.0 mg., 0.52 mmol) and Pd[Ph3P]4 (22.0 mg., 0.0175 mmol) were taken into a solution mixture of 2M Na2CO3 (aq) (1.2 mL), toluene (2.8 mL) and EtOH (1.4 mL). Workup as in example 15 gave the final pure compound 125 (28.0 mg., 20%). LC/MS, Peak at 3.23 minute m=402.1-406.5 (M+1). Purity is 99%. The proton NMR was consistent with the expected structure.

Example 17. Synthesis of Compound 122

1-(5-tert-Butyl-isoxazol-3-yl)-3-[3-(5-morpholin-4-yl-7-oxo-7H-thieno[3,2-b]pyran-3-yl)-phenyl]-urea (compound 122)

3-Bromo-5-morpholin-4-yl-thieno[3,2-b]pyran-7-one (compound 126) (412 mg, 1.3 mmol) and 3-aminophenyl boronic acid (232 mg, 1.67 mmol) were dissolved in 1,4-dioxane (6 mL) and treated with 2 M aqueous Na2CO3 (2 mL). The resulting mixture was degassed with nitrogen for 10 minutes. This was treated with Pd[Ph3P]4 (20 mg, 0.017 mmol) and the resulting mixture was heated to 95° C. for 6 hrs under a nitrogen atmosphere. The reaction mixture was cooled, diluted with ethyl acetate (20 mL) and filtered through Celite. The filtrate was washed with water (20 mL) and the organic phase was separated, dried (Na2SO4), filtered and concentrated in vacuo to yield the crude amine (618 mg). The crude compound was purified on silica gel column chromatography, eluting first with toluene to remove the triphenylphosphine oxide impurity, followed by elution with a 1-4% methanol in ethyl acetate gradient. The purification yielded 3-(3-Amino-phenyl)-5-morpholin-4-yl-thieno[3,2-b]pyran-7-one (Compound 11) (380 mg, 1.16 mmol, 89%). HPLC (254 nm)—Rt 2.88 min. MS (ESI) m/z 329.1.14 [M+H]+. Purity>98% by UV (254 nm).

3-(3-Amino-phenyl)-5-morpholin-4-yl-thieno[3,2-b]pyran-7-one (Compound 11) (40 mg, 0.122 mmol) from the previous step was dissolved in 1,2-dichloroethane (7 mL) and treated with 5-tert-butyl-3-isocyanato-isoxazole (21 mg, 0.122 mmol) and the solution was heated to 50° C. for 15 hours. The reaction was cooled to room temperature, treated with methanol (2 mL) and stirred for 2 hours. The volatiles were removed in vacuo and the crude residue was purified by preparative thin layer chromatography (TLC) plates on silica gel (1000 μm) eluting with a 95:5 v/v mixture of CH2Cl2 and methanol, respectively. The product, Compound 122, was obtained as an off-white solid. Yield=10 mg (0.02 mmol, 17%). HPLC (254 nm)—Rt 3.23 min. MS (ESI) m/z 495.4 [M+H]+. Purity>98% by UV (254 nm). Proton NMR (400 MHz—DMSO-d6) δ 9.58 (s, 1H); 8.94 (s, 1H); 8.18 (s, 1H); 8.10 (m, 1H); 7.43 (t, J=6.6 Hz, 1H); 7.36 (d, J=6.6 Hz, 1H); 7.26 (d, J=6.6 Hz, 1H); 6.51 (s, 1H); 5.53 (s, 1H); 3.72 (t, J=4.0 Hz, 4H); 3.47 (t, J=4.0 Hz, 4H); 1.30, (s, 9H).

Example 18. Synthesis of Compound 123

1-(4-Chloro-3-trifluoromethyl-phenyl)-3-[3-(5-morpholin-4-yl-7-oxo-7H-thieno[3,2-b]pyran-3-yl)-phenyl]-urea (Compound 123)

3-(3-Amino-phenyl)-5-morpholin-4-yl-thieno[3,2-b]pyran-7-one (compound 11) (40 mg, 0.122 mmol) was dissolved in 1,2-dichloroethane (7 mL) and treated with 1-chloro-4-isocyanato-2-trifluoromethyl-benzene (27 mg, 0.122 mmol) and the solution was heated to 50° C. for 15 hours. The reaction was cooled to room temperature, treated with methanol (10 mL) and refluxed for 1 hour. Upon cooling, the white precipitate was filtered and dried under vacuum to afford product Compound 123 as a white solid. Yield=25 mg (0.045 mmol, 37%). HPLC (254 nm)—Rt 3.41 min. MS (ESI) m/z 550.4 [M+H]+. Purity>98% by UV (254 nm). Proton NMR (400 MHz—DMSO-d6) δ 9.21 (s, 1H); 8.98 (s, 1H); 8.16 (s, 2H); 8.12 (br, 1H); 7.62 (m, 2H); 7.43 (br t, J=6.4 Hz, 1H); 7.35 (br d, J=6.0 Hz, 1H); 7.25 (br d, J=6.0 Hz, 1H); 5.53 (s, 1H); 3.69 (br, 4H); 3.47 (br, 4H); 1.30, (s, 9H).

Example 19. Synthesis of Compound 129

5-Morpholino-3-(2H-pyrazol-3-yl)-4-oxa-1-thia-7-Indenone (compound 129)

3-Bromo-5-morpholino-4-oxa-1-thia-7-indenone (Compound 126) (48 mg, 0.15 mmol), 1H-pyrazole-5-boronic acid (21 mg, 0.18 mmol), Pd[PPh3]4 (20 mg., 0.015 mmol) were taken into a mixture of toluene (0.8 mL), H2O/EtOH 1:1 (0.9 mL) under stirring and heated to 80° C. for 18 hours.

Then the reaction mixture was cooled and diluted with ethyl acetate (30 mL) and filtered. The filtrate was washed with water, dried (Na2SO4), filtered and concentrated to yield a crude solid product (40 mg). The crude was purified by preparative TLC plate on silica gel, eluting with 30:70 v/v ethyl acetate:CH2Cl2 yielding (8 mg, 0.026 mmol, 18%) of the final compound 129. HPLC (254 nm)—Rt 0.65 min. MS (ESI) m/z 304.1[M+H]$^+$. Purity=>95% by UV (254 nm).

Example 20. Synthesis of Compound 130

3-(1-Methyl-1H-indazol-6-yl)-5-morpholino-4-oxa-1-thia-7-Indenone (compound 130)

3-Bromo-5-morpholino-4-oxa-1-thia-7-indenone (Compound 126) (53 mg, 0.17 mmol), 4,4,5,5-tetramethyl-2-(1-methyl-1H-indazol-6-yl)-1,3,2-dioxaborolane (87 mg, 0.34 mmol), were dissolved in toluene/EtOH (1.7 mL of a 2:1 v/v mixture) and treated with 2 M aqueous Na2CO3 (0.6 mL). The resulting mixture was degassed with nitrogen for 10 minutes. This was treated with Pd[Ph3P]4 (10 mg, 8.4 μmol) and the resulting mixture was heated to 90° C. for 2 hours under a nitrogen atmosphere. The reaction mixture was cooled, diluted with ethyl acetate (20 mL) and filtered through a pad of Celite. The filtrate was washed with water (20 mL) and the organic phase was separated, dried (Na2SO4), filtered and concentrated in vacuo to yield the crude material. This was purified by preparative TLC plate eluting with ethyl acetate. The plate was run three times. 3-(1-Methyl-1H-indazol-6-yl)-5-morpholino-4-oxa-1-thia-7-indenone (Compound 130) was obtained as a white solid (4 mg, 0.01 mmol, 6%). HPLC (254 nm)—Rt 3.09 min. MS (ESI) m/z 368.3 [M+H]$^+$. Purity=94.6% by UV (254 nm).

Example 21. Synthesis of Compound 131

3-(3-Methyl-1H-indazol-6-yl)-5-morpholino-4-oxa-1-thia-7-Indenone (Compound 131)

3-Bromo-5-morpholino-4-oxa-1-thia-7-indenone (compound 126)(100 mg, 0.3 mmol) and 3-methyl-1H-indazole-6-boronic acid (72 mg, 0.4 mmol) were dissolved in DMF (2 mL) and treated with 2 M aqueous Na2CO3 (1 mL). The resulting mixture was degassed with nitrogen for 10 minutes. This was treated with Pd[Ph3P]4 (5 mg, 4.7 μmol) and the resulting mixture was heated to 80° C. for 3 hours under a nitrogen atmosphere. The reaction mixture was cooled, diluted with ethyl acetate (20 mL) and filtered through Celite. The filtrate was washed with water (20 mL) and the organic phase was separated, dried (Na2SO4), filtered and concentrated in vacuo to yield the crude amine (75 mg). The crude compound was purified by preparative TLC using hexane/ethylacetate (50:50) The purification yielded 3-(3-Methyl-1H-indazol-6-yl)-5-morpholino-4-oxa-1-thia-7-indenone (5.1 mg, 0.01 mmol, 4.3%). HPLC (254 nm)—Rt 0.48 min. MS (ESI) m/z 368.2 [M+H]$^+$. Purity>86.1% by UV (254 nm).

Example 22. Synthesis of Compound 132

3-[p-(5-Methyl-1,3,4-oxadiazol-2-yl)phenyl]-5-morpholino-4-oxa-1-thia-7-indenone (compound 132)

3-Bromo-5-morpholino-4-oxa-1-thia-7-indenone (compound 126) (100 mg, 0.3 mmol) and 4-(5-methyl-1,3,4-oxadiazol-2-yl)phenylboronic acid (83 mg, 0.4 mmol) were dissolved in acetonitrile (2 mL) and treated with 2 M aqueous Na2CO3 (1 mL). The resulting mixture was degassed with nitrogen for 10 minutes. This was treated with Pd[Ph3P]4 (5.4 mg, 4.7 μmol) and the resulting mixture was heated to 80° C. for 3 hours under a nitrogen atmosphere. The reaction mixture was cooled, diluted with ethyl acetate (20 mL) and filtered through Celite. The filtrate was washed with water (20 mL) and the organic phase was separated, dried (Na2SO4), filtered and concentrated in vacuo to yield the crude amine (65 mg). The crude compound was purified by preparative TLC using hexane/ethylacetate (50:50) The purification yielded 3-[p-(5-methyl-1,3,4-oxadiazol-2-yl) phenyl]-5-morpholino-4-oxa-1-thia-7-indenone (compound 132) (5.2 mg, 0.01 mmol, 4%). HPLC (254 nm)—Rt 0.29 min. MS (ESI) m/z 396.2 [M+H]$^+$. Purity>99.9% by UV (254 nm).

Example 23. Synthesis of Compound 133

3-[m-(3-Methylureido)phenyl]-5-morpholino-4-oxa-1-thia-7-indenone (compound 133)

3-(3-Amino-phenyl)-5-morpholin-4-yl-thieno[3,2-b] pyran-7-one (compound 11) (60 mg, 0.183 mmol) was dissolved in CH2Cl2 (2 mL) and treated with methyl isocyanate (36 mg, 0.555 mmol) and the solution was stirred at RT overnight. The next day, the solid product was filtered and triturated with a mixture of CH2Cl2 and MeOH three times. Solids were filtered and dried to yield the final desired compound 133 (25 mg, 36%). HPLC (254 nm)—Rt 3.83 min. MS (ESI) m/z 386.3 [M+H]. Purity=99% by UV (254 nm). $^1$H NMR (400 MHz—DMSO-d6) δ 8.62 (s, 1H); 8.12 (s, 1H); 8.09 (t, J=1.6 Hz, 1H); 7.33 (t, J=6.0 Hz, 1H); 7.22 (d, J=6.0 Hz, 1H); 7.17 (d, J=6.0 Hz, 1H); 6.05 (m, 1H); 5.52 (s, 1H); 3.72 (t, J=4.0 Hz, 4H); 3.47 (t, J=4.0 Hz, 4H); 2.65, (d, J=4.0 Hz, 3H).

Example 24. Synthesis of Compound 134

3-[m-(3,3-Dimethylureido)phenyl]-5-morpholino-4-oxa-1-thia-7-indenone (compound 134)

3-(3-Amino-phenyl)-5-morpholin-4-yl-thieno[3,2-b] pyran-7-one (Compound 11)(240 mg, 0.73 mmol) was dissolved in DMA (3 mL) and treated with dimethylcarbamyl chloride (120 mg, 1.1 mmol) and Hunig's base (0.325 mL, 1.84 mmol). Mixture was heated to 90° C. overnight. Next morning, reaction was cooled and diluted with ethyl acetate (30 mL), washed with water, 1N HCl aqueous and brine. The organic layer was dried (Na2SO4), filtered and concentrated in vacuo. The crude was purified by preparative thin layer chromatography on silica-gel, eluting with a 95:5 v/v mixture of CH2Cl2 and MeOH, respectively, yielding the pure urea as a tan solid (92.0 mg, 31%). HPLC (254 nm)—Rt 3.80 min. MS (ESI) m/z 400.2 [M+H]$^+$. Purity=96.4% by UV (254 nm). $^1$HNMR (400 MHz—DMSO-d6) δ 8.39 (s, 1H); 8.11 (s, 1H); 8.05 (br s, 1H); 7.40-7.33 (m, 2H); 7.25 (d, J=4.8 Hz, 1H); 5.52 (s, 1H); 3.72 (t, J=4.0 Hz, 4H); 3.47 (t, J=4.0 Hz, 4H); 2.94, (s, 6H).

Example 25. Synthesis of Compound 135

5-Morpholino-3-{m-[3-(m-tolyl)ureido]phenyl}-4-oxa-1-thia-7-indenone (compound 135)

3-(3-Amino-phenyl)-5-morpholin-4-yl-thieno[3,2-b] pyran-7-one (compound 11) (60 mg, 0.183 mmol) was dissolved in CH2Cl2 (2 mL) and treated with 3-methylphenyl isocyanate (34 mg, 0.183 mmol) and the solution was stirred at RT overnight. The next day, the solid product was filtered and triturated with a mixture of CH2Cl2 and MeOH three times. Solids were filtered and dried to yield the final desired compound 135 (35 mg, 41%). HPLC (254 nm)—Rt 3.16 min. MS (ESI) m/z 462.3 [M+H]$^+$. Purity=99% by UV (254 nm). Proton HNMR (400 MHz—DMSO-d6) δ 8.77 (s, 1H); 8.63 (s, 1H); 8.16 (s, 1H); 8.15 (s, 1H); 7.41 (t, J=6.6 Hz, 1H); 7.39 (br s, 1H); 7.30 (d, J=6.6 Hz, 1H); 7.22-7.15 (m, 3H); 6.80 (d, J=5.6 Hz, 1H); 5.53 (s, 1H); 3.71 (br, 4H); 3.49 (br, 4H); 2.28 (s, 3H).

Example 26. Synthesis of Compound 136

5-Morpholino-3-(m-{3-[m-(trifluoromethyl)phenyl]ureido}phenyl)-4-oxa-1-thia-7-Indenone (compound 136)

3-(3-Amino-phenyl)-5-morpholin-4-yl-thieno[3,2-b]pyran-7-one (compound 11) (60 mg, 0.183 mmol) was dissolved in CH2Cl2 (2 mL) and treated with 3-trifluoromethylphenyl isocyanate (35 mg, 0.183 mmol) and the solution was stirred at RT overnight. The next day, the solid product was filtered and triturated with a mixture of CH2Cl2 and MeOH three times. Solids were filtered and dried to yield the final desired Compound 136 (28 mg, 30%). HPLC (254 nm)—Rt 4.16 min. MS (ESI) m/z 516.5 [M+H]$^+$. Purity >99% by UV (254 nm). 1HNMR (400 MHz—DMSO-d6) δ 9.09 (s, 1H); 8.92 (s, 1H); 8.17 (s, 1H); 8.15 (br s, 1H); 8.08 (br s, 1H); 7.53 (m, 2H); 7.43 (t, J=6.6 Hz, 1H); 7.33 (m, 2H); 7.23 (d, J=6.6 Hz, 1H); 5.53 (s, 1H); 3.70 (t, J=4.0 Hz, 4H); 3.48 (t, J=4.0 Hz, 4H).

Example 27. Synthesis of Compound 137

5-Morpholino-3-{m-[3-(2,5-xylyl)ureido]phenyl}-4-oxa-1-thia-7-indenone (compound 137)

3-(3-Amino-phenyl)-5-morpholin-4-yl-thieno[3,2-b]pyran-7-one (compound 11) (71 mg, 0.216 mmol) was dissolved in CH2Cl2 (4 mL) and treated with 2,5-dimethylphenyl isocyanate (32 mg, 0.216 mmol) and the solution was stirred at room temperature overnight. The next day, the solid product was filtered and triturated with a mixture of CH2Cl2 and MeOH three times. Solids were filtered and dried to yield the final desired compound 137 (26 mg, 25%). HPLC (254 nm)—Rt 4.30 min. MS (ESI) m/z 476.4 [M+H]$^+$. Purity=99% by UV (254 nm). 1HNMR (400 MHz—DMSO-d6) δ 9.14 (s, 1H); 8.20 (s, 1H); 8.16 (s, 1H); 7.90 (s, 1H); 7.71 (s, 1H); 7.41 (t, J=6.0 Hz, 1H); 7.31 (d, J=6.0 Hz, 1H); 7.18 (d, J=6.0 Hz, 1H); 7.05 (d, J=6.0 Hz, 1H); 6.77 (d, J=6.0 Hz, 1H); 5.53 (s, 1H); 3.70 (t, J=4.0 Hz, 4H); 3.49 (t, J=4.0 Hz, 4H); 2.25, (s, 3H); 2.20 (s, 3H).

TABLE 3

Structures of compounds and PC3 pAKT IC50 and BRD4 Docking Energy

| Cmpd No. | Chemical Structure | PC3 pAKT IC50 (μMolar) | BRD4 Docking Energy |
|---|---|---|---|
| LY294002 | 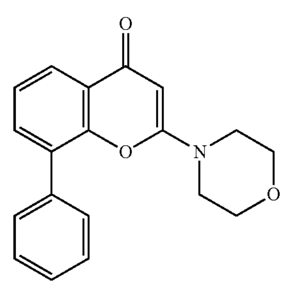 [SMILES: O=c1cc(N2CCOCC2)oc2c(-c3ccccc3)cccc12] | ND | −22.61 |
| | | ND | −30.91 |

TABLE 3-continued

Structures of compounds and PC3 pAKT IC50 and BRD4 Docking Energy

| Cmpd No. | Chemical Structure | PC3 pAKT IC50 (μMolar) | BRD4 Docking Energy |
| --- | --- | --- | --- |
| 1 | 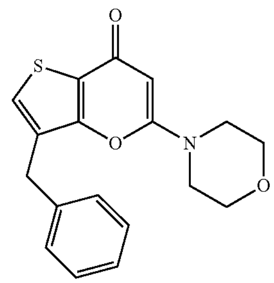 [SMILES: O=c1cc(N2CCOCC2)oc2c(Cc3ccccc3)csc12] | 0.864 | −10.44 |
| 2 | 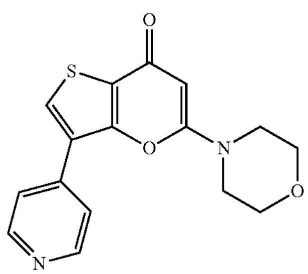 [SMILES: O=c1cc(N2CCOCC2)oc2c(-c3ccncc3)csc12] | 3.031 | −18.24 |
| 3 | 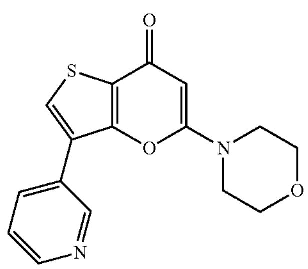 [SMILES: O=c1cc(N2CCOCC2)oc2c(-c3cccnc3)csc12] | 4.872 | −17.58 |
| 4 | 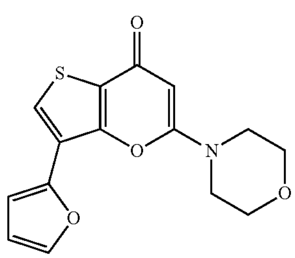 [SMILES: O=c1cc(N2CCOCC2)oc2c(-c3ccco3)csc12] | 0.93 | −12.31 |
| 5 | 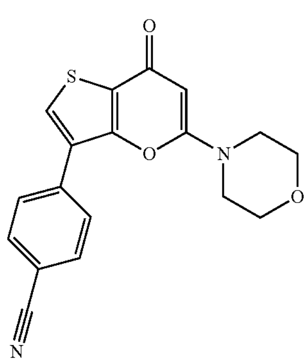 [SMILES: N#Cc1ccc(-c2csc3c(=O)cc(N4CCOCC4)oc23)cc1] | 7.3 | −15.60 |

TABLE 3-continued

Structures of compounds and PC3 pAKT IC50 and BRD4 Docking Energy

| Cmpd No. | Chemical Structure | PC3 pAKT IC50 (μMolar) | BRD4 Docking Energy |
|---|---|---|---|
| 6 | 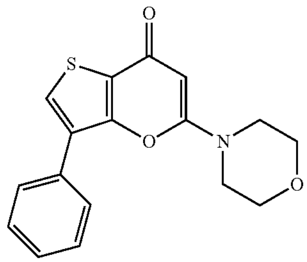 [SMILES: O=c1cc(N2CCOCC2)oc2c(-c3ccccc3)csc12] | 0.55 | −19.30 |
| 7 | 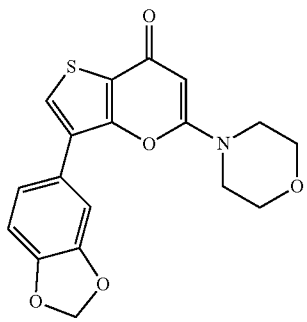 [SMILES: O=c1cc(N2CCOCC2)oc2c(-c3ccc4c(c3)OCO4)csc12] | 0.54 | −19.85 |
| 8 | 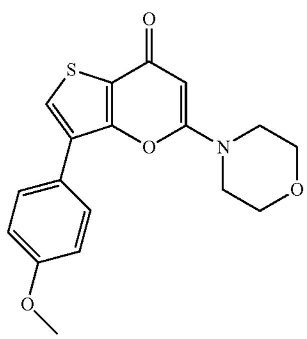 [SMILES: COc1ccc(-c2csc3c(=O)cc(N4CCOCC4)oc23)cc1] | 0.98 | −17.89 |
| 9 | 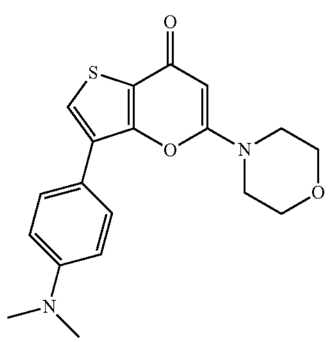 [SMILES: CN(C)c1ccc(-c2csc3c(=O)cc(N4CCOCC4)oc23)cc1] | 0.78 | −19.96 |
| 10 | 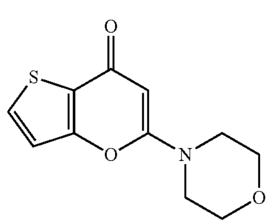 [SMILES: O=c1cc(N2CCOCC2)oc2ccsc12] | ND | −9.20 |

TABLE 3-continued

Structures of compounds and PC3 pAKT IC50 and BRD4 Docking Energy

| Cmpd No. | Chemical Structure | PC3 pAKT IC50 (μMolar) | BRD4 Docking Energy |
|---|---|---|---|
| 11 | 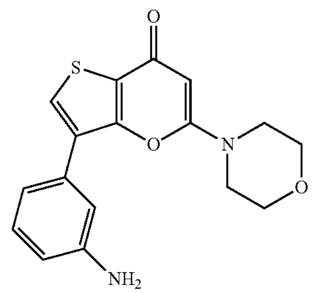 [SMILES: Nc1cccc(-c2csc3c(=O)cc(N4CCOCC4)oc23)c1] | 6.317 | −23.39 |
| 12 | 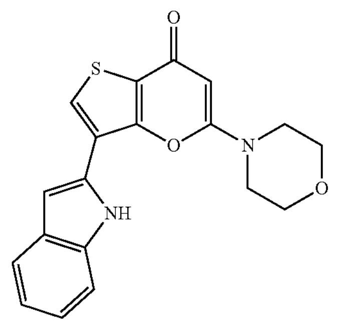 [SMILES: O=c1cc(N2CCOCC2)oc2c(-c3cc4ccccc4[nH]3)csc12] | 1.574 | −28.22 |
| 14 | 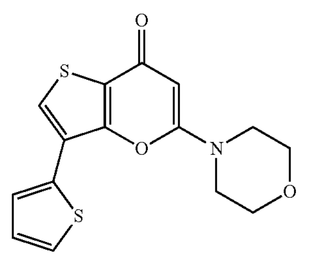 | 1.021 | −14.91 |
| 15 | 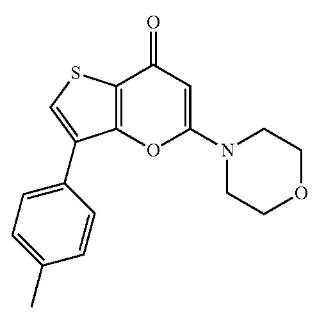 [SMILES: Cc1ccc(-c2csc3c(=O)cc(N4CCOCC4)oc23)cc1] | 0.948 | −18.85 |
| 16 | 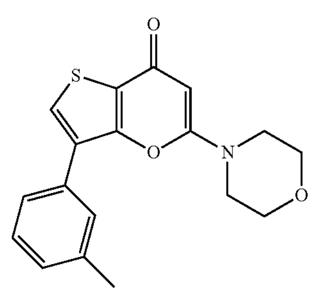 [SMILES: Cc1cccc(-c2csc3c(=O)cc(N4CCOCC4)oc23)c1] | 1.229 | −17.36 |

TABLE 3-continued

Structures of compounds and PC3 pAKT IC50 and BRD4 Docking Energy

| Cmpd No. | Chemical Structure | PC3 pAKT IC50 (μMolar) | BRD4 Docking Energy |
|---|---|---|---|
| 17 | 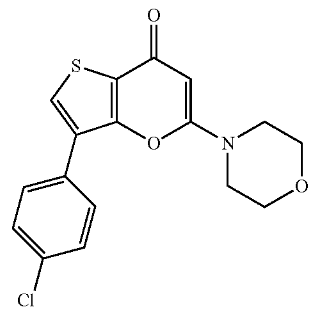 [SMILES: O=c1cc(N2CCOCC2)oc2c(-c3ccc(Cl)cc3)csc12] | 1.41 | −18.73 |
| 18 | 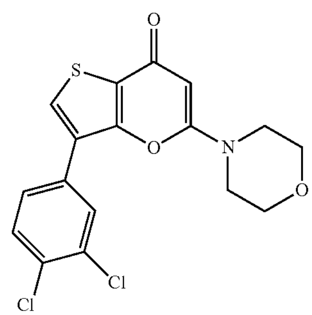 [SMILES: O=c1cc(N2CCOCC2)oc2c(-c3ccc(Cl)c(Cl)c3)csc12] | 0.913 | −17.67 |
| 19 | 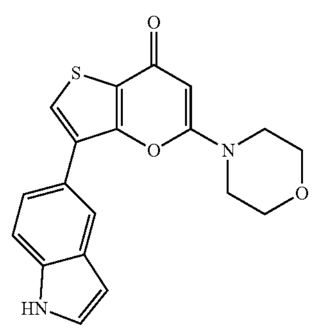 [SMILES: O=c1cc(N2CCOCC2)oc2c(-c3ccc4[nH]ccc4c3)csc12] | 0.901 | −21.96 |
| 20 | 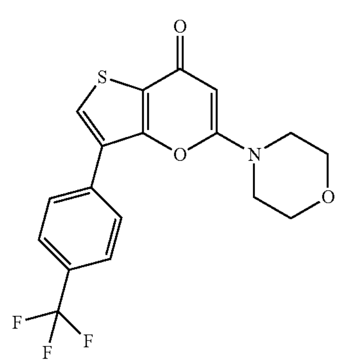 [SMILES: O=c1cc(N2CCOCC2)oc2c(-c3ccc(C(F)(F)F)cc3)csc12] | ND | −16.74 |

TABLE 3-continued

Structures of compounds and PC3 pAKT IC50 and BRD4 Docking Energy

| Cmpd No. | Chemical Structure | PC3 pAKT IC50 (µMolar) | BRD4 Docking Energy |
|---|---|---|---|
| 21 | 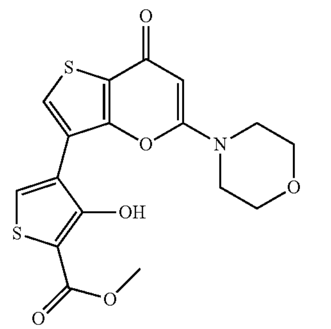 [SMILES: COC(=O)c1scc(-c2csc3c(=O)cc(N4CCOCC4)oc23)c1O] | 1.038 | −19.76 |
| 22 | 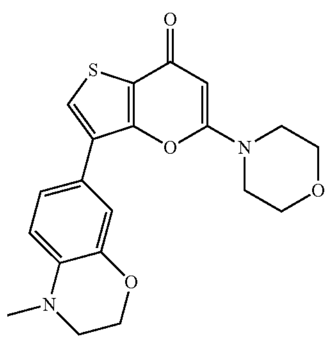 [SMILES: CN1CCOc2cc(-c3csc4c(=O)cc(N5CCOCC5)oc34)ccc21] | 0.609 | −23.22 |
| 23 | 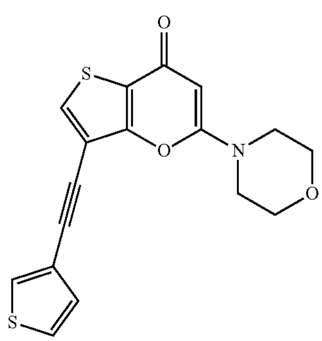 [SMILES: O=c1cc(N2CCOCC2)oc2c(C#Cc3ccsc3)csc12] | 1.274 | −11.26 |
| 24 | 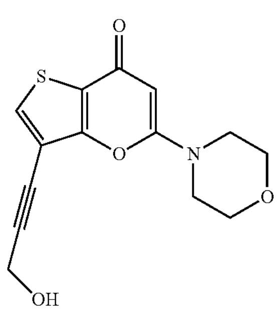 [SMILES: O=c1cc(N2CCOCC2)oc2c(C#CCO)csc12] | 4.606 | −8.39 |

TABLE 3-continued

Structures of compounds and PC3 pAKT IC50 and BRD4 Docking Energy

| Cmpd No. | Chemical Structure | PC3 pAKT IC50 (µMolar) | BRD4 Docking Energy |
|---|---|---|---|
| 26 | 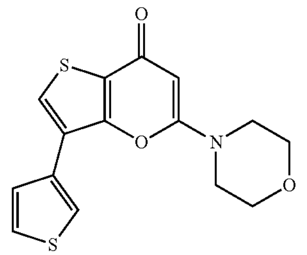 [SMILES: O=c1cc(N2CCOCC2)oc2c(-c3ccsc3)csc12] | 1.558 | −14.68 |
| 27 | 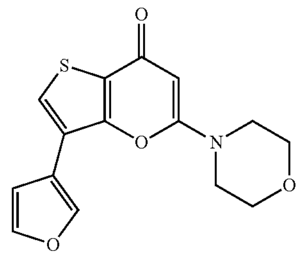 [SMILES: O=c1cc(N2CCOCC2)oc2c(-c3ccoc3)csc12] | 3.235 | −12.36 |
| 28 | 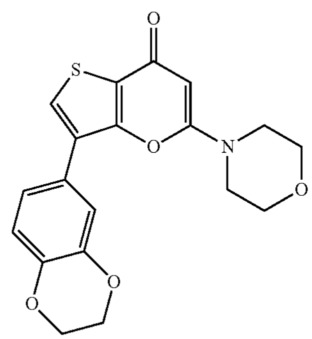 [SMILES: O=c1cc(N2CCOCC2)oc2c(-c3ccc4c(c3)OCCO4)csc12] | 0.161–0.44 | −18.81 |
| 29 | 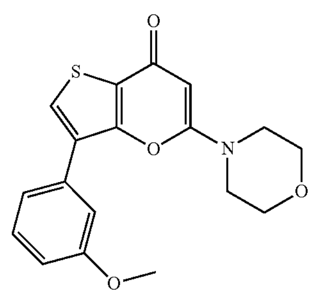 [SMILES: COc1cccc(-c2csc3c(=O)cc(N4CCOCC4)oc23)c1] | 1.067 | −19.48 |
| 32 | 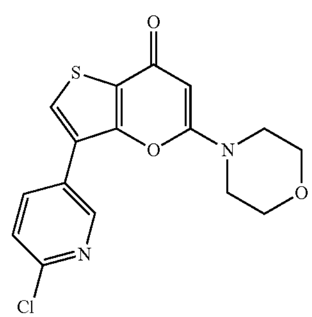 [SMILES: O=c1cc(N2CCOCC2)oc2c(-c3ccc(Cl)nc3)csc12] | ND | −17.32 |

TABLE 3-continued

Structures of compounds and PC3 pAKT IC50 and BRD4 Docking Energy

| Cmpd No. | Chemical Structure | PC3 pAKT IC50 (μMolar) | BRD4 Docking Energy |
|---|---|---|---|
| 35 | 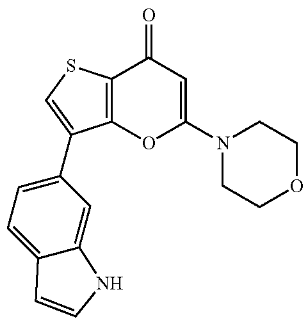 [SMILES: O=c1cc(N2CCOCC2)oc2c(-c3ccc4cc[nH]c4c3)csc12] | ND | −25.41 |
| 41 | 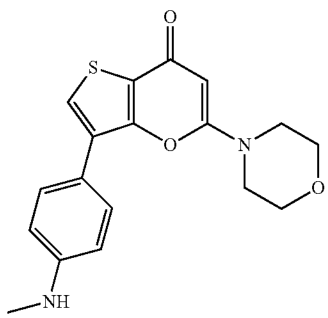 [SMILES: CNc1ccc(-c2csc3c(=O)cc(N4CCOCC4)oc23)cc1] | ND | −19.31 |
| 42 | 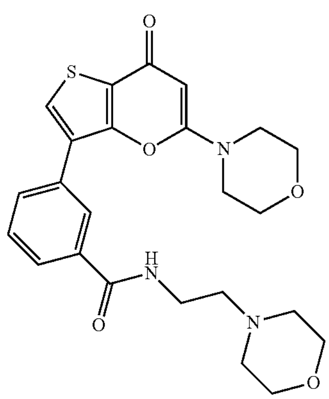 [SMILES: O=C(NCCN1CCOCC1)c1cccc(-c2csc3c(=O)cc(N4CCOCC4)oc23)c1] | ND | −24.09 |
| 45 | 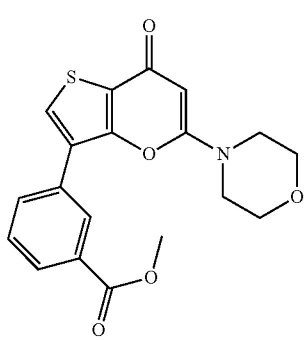 [SMILES: COC(=O)c1cccc(-c2csc3c(=O)cc(N4CCOCC4)oc23)c1] | ND | −22.90 |

TABLE 3-continued
Structures of compounds and PC3 pAKT IC50 and BRD4 Docking Energy
| Cmpd No. | Chemical Structure | PC3 pAKT IC50 (μMolar) | BRD4 Docking Energy |
|---|---|---|---|
| 47 | 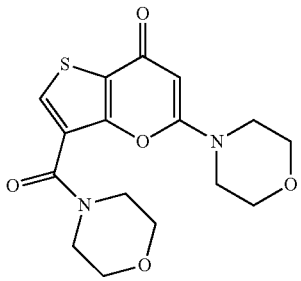 [SMILES: O=C(c1csc2c(=O)cc(N3CCOCC3)oc12)N1CCOCC1] | ND | −13.83 |
| 48 | 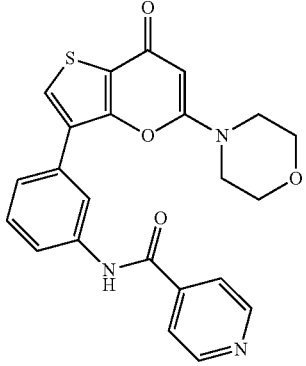 [SMILES: O=C(Nc1cccc(-c2csc3c(=O)cc(N4CCOCC4)oc23)c1)c1ccncc1] | ND | −16.86 |
| 49 | 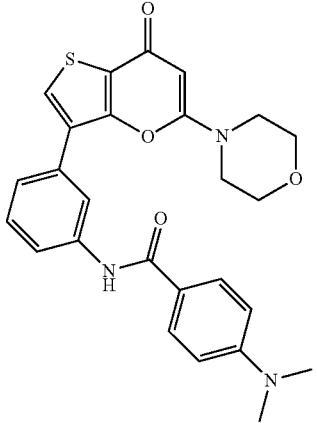 [SMILES: CN(C)c1ccc(C(=O)Nc2cccc(-c3csc4c(=O)cc(N5CCOCC5)oc34)c2)cc1] | ND | −10.07 |
| 51 | 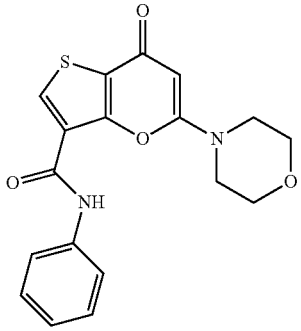 [SMILES: O=C(Nc1ccccc1)c1csc2c(=O)cc(N3CCOCC3)oc12] | ND | −24.06 |

TABLE 3-continued

Structures of compounds and PC3 pAKT IC50 and BRD4 Docking Energy

| Cmpd No. | Chemical Structure | PC3 pAKT IC50 (µMolar) | BRD4 Docking Energy |
|---|---|---|---|
| 52 | 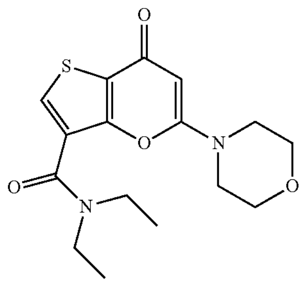 [SMILES: CCN(CC)C(=O)c1csc2c(=O)cc(N3CCOCC3)oc12] | ND | −4.91 |
| 56 | 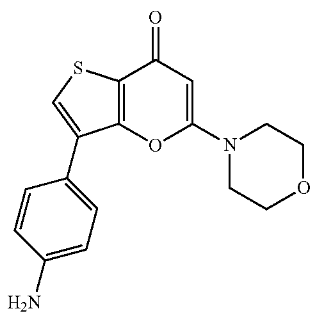 [SMILES: Nc1ccc(-c2csc3c(=O)cc(N4CCOCC4)oc23)cc1] | ND | −18.47 |
| 63 | 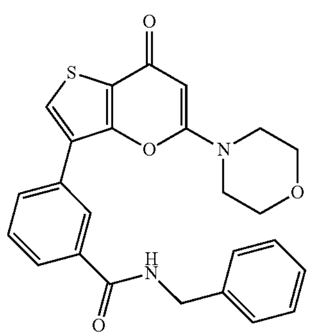 [SMILES: O=C(NCc1ccccc1)c1cccc(-c2csc3c(=O)cc(N4CCOCC4)oc23)c1] | ND | −24.13 |
| 64 | 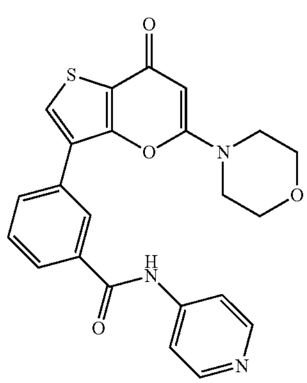 [SMILES: O=C(Nc1ccncc1)c1cccc(-c2csc3c(=O)cc(N4CCOCC4)oc23)c1] | ND | −24.97 |

TABLE 3-continued

Structures of compounds and PC3 pAKT IC50 and BRD4 Docking Energy

| Cmpd No. | Chemical Structure | PC3 pAKT IC50 (µMolar) | BRD4 Docking Energy |
|---|---|---|---|
| 66 | 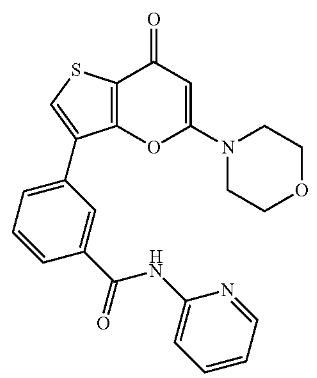 [SMILES: O=C(Nc1ccccn1)c1cccc(-c2csc3c(=O)cc(N4CCOCC4)oc23)c1] | ND | −27.07 |
| 85 | 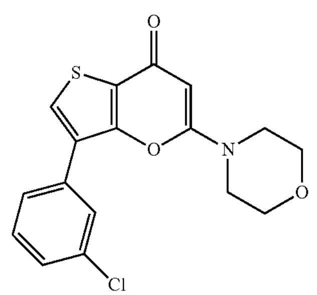 [SMILES: O=c1cc(N2CCOCC2)oc2c(-c3cccc(Cl)c3)csc12] | ND | −17.89 |
| 86 | 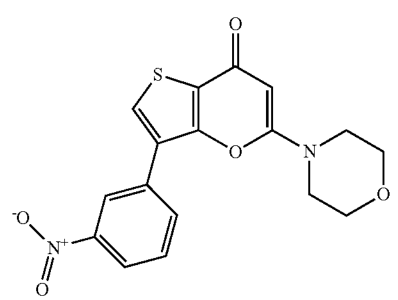 | ND | −25.04 |
| 88 | 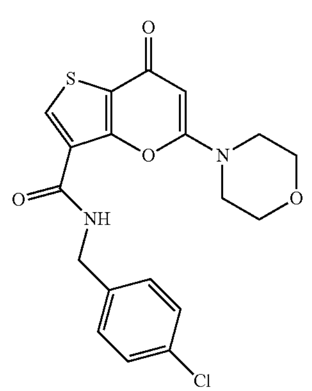 [SMILES: O=C(NCc1ccc(Cl)cc1)c1csc2c(=O)cc(N3CCOCC3)oc12] | ND | −19.12 |

TABLE 3-continued

Structures of compounds and PC3 pAKT IC50 and BRD4 Docking Energy

| Cmpd No. | Chemical Structure | PC3 pAKT IC50 (µMolar) | BRD4 Docking Energy |
|---|---|---|---|
| 89 | 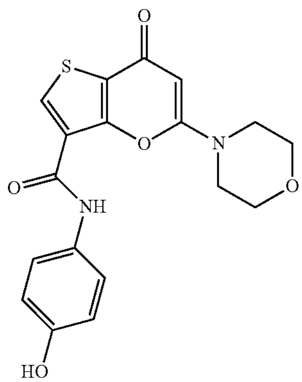 [SMILES: O=C(Nc1ccc(O)cc1)c1csc2c(=O)cc(N3CCOCC3)oc12] | ND | −11.43 |
| 90 | 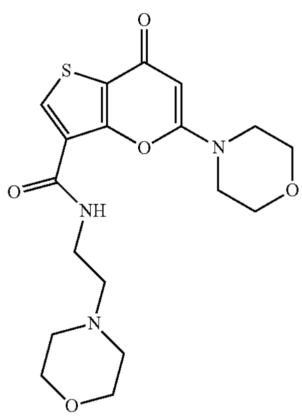 [SMILES: O=C(NCCN1CCOCC1)c1csc2c(=O)cc(N3CCOCC3)oc12] | ND | −16.43 |
| 91 | 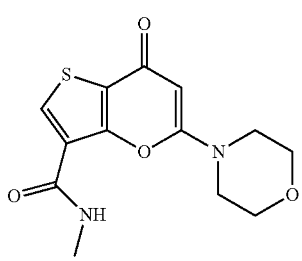 [SMILES: CNC(=O)c1csc2c(=O)cc(N3CCOCC3)oc12] | ND | −20.48 |
| 92 | 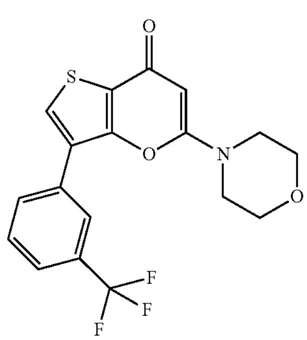 [SMILES: O=c1cc(N2CCOCC2)oc2c(-c3cccc(C(F)(F)F)c3)csc12] | ND | −19.16 |

TABLE 3-continued

Structures of compounds and PC3 pAKT IC50 and BRD4 Docking Energy

| Cmpd No. | Chemical Structure | PC3 pAKT IC50 (μMolar) | BRD4 Docking Energy |
|---|---|---|---|
| 93 | 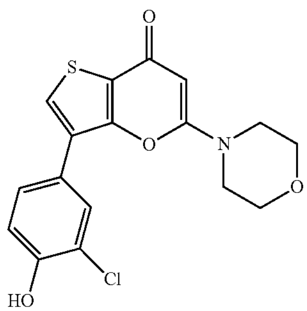 [SMILES: O=c1cc(N2CCOCC2)oc2c(-c3ccc(O)c(Cl)c3)csc12] | ND | −16.39 |
| 94 | 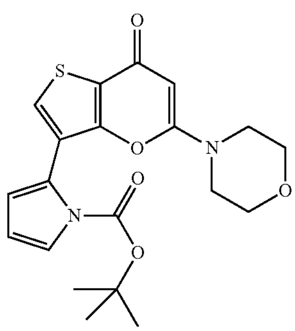 [SMILES: CC(C)(C)OC(=O)n1cccc1-c1csc2c(=O)cc(N3CCOCC3)oc12] | ND | −18.49 |
| 95 | 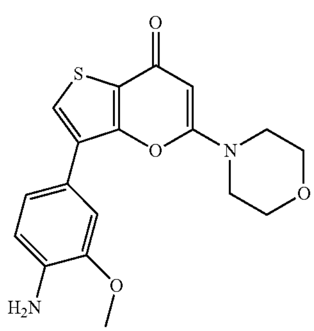 [SMILES: COc1cc(-c2csc3c(=O)cc(N4CCOCC4)oc23)ccc1N] | ND | −18.10 |
| 97 | 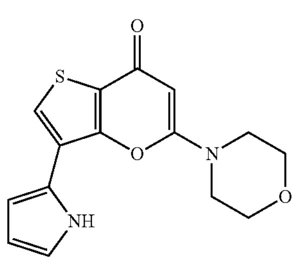 [SMILES: O=c1cc(N2CCOCC2)oc2c(-c3ccc[nH]3)csc12] | ND | −24.37 |

TABLE 3-continued

Structures of compounds and PC3 pAKT IC50 and BRD4 Docking Energy

| Cmpd No. | Chemical Structure | PC3 pAKT IC50 (μMolar) | BRD4 Docking Energy |
|---|---|---|---|
| 98 | 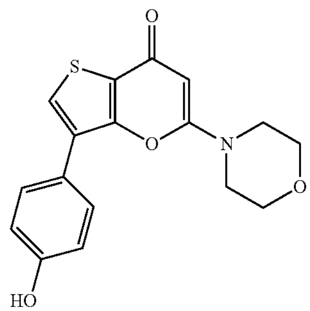 | ND | −14.81 |
| 99 | 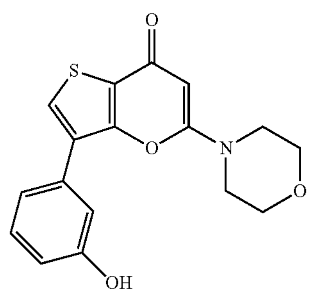 [SMILES: O=c1cc(N2CCOCC2)oc2c(-c3cccc(O)c3)csc12] | ND | −22.67 |
| 100 | 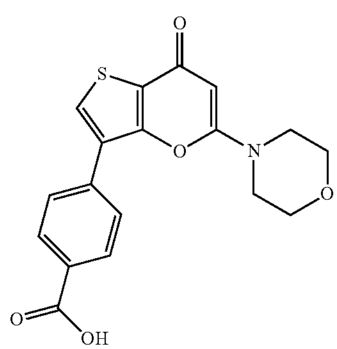 [SMILES: O=C(O)c1ccc(-c2csc3c(=O)cc(N4CCOCC4)oc23)cc1] | ND | −15.82 |
| 101 | 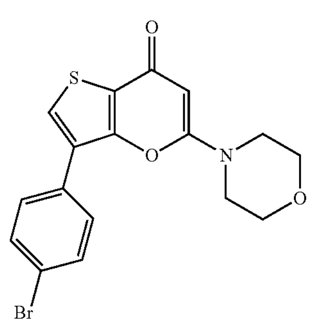 [SMILES: O=c1cc(N2CCOCC2)oc2c(-c3ccc(Br)cc3)csc12] | ND | −18.67 |

TABLE 3-continued

Structures of compounds and PC3 pAKT IC50 and BRD4 Docking Energy

| Cmpd No. | Chemical Structure | PC3 pAKT IC50 (µMolar) | BRD4 Docking Energy |
|---|---|---|---|
| 102 | 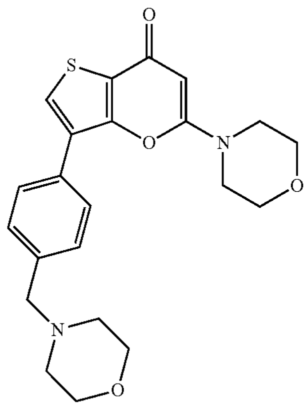 [SMILES: O=c1cc(N2CCOCC2)oc2c(-c3ccc(CN4CCOCC4)cc3)csc12] | ND | −16.70 |
| 103 | 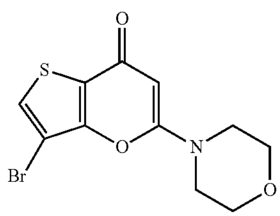 [SMILES: O=c1cc(N2CCOCC2)oc2c(Br)csc12] | ND | −9.77 |
| 105 | 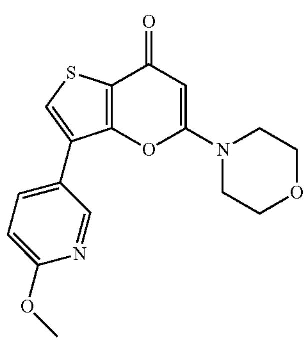 [SMILES: COc1ccc(-c2csc3c(=O)cc(N4CCOCC4)oc23)cn1] | ND | −16.49 |
| 107 | 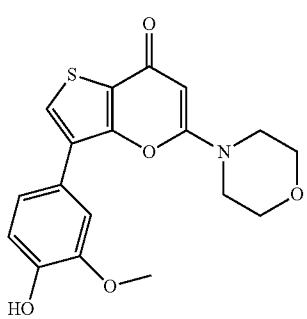 [SMILES: COc1cc(-c2csc3c(=O)cc(N4CCOCC4)oc23)ccc1O] | ND | −14.61 |

TABLE 3-continued

Structures of compounds and PC3 pAKT IC50 and BRD4 Docking Energy

| Cmpd No. | Chemical Structure | PC3 pAKT IC50 (µMolar) | BRD4 Docking Energy |
|---|---|---|---|
| 108 | 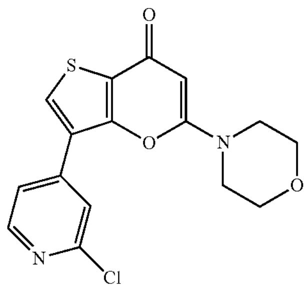 [SMILES: O=c1cc(N2CCOCC2)oc2c(-c3ccnc(Cl)c3)csc12] | ND | −18.61 |
| 110 | 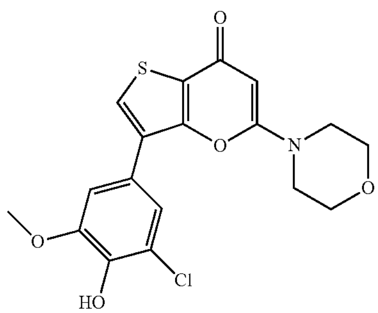 [SMILES: COc1cc(-c2csc3c(=O)cc(N4CCOCC4)oc23)cc(Cl)c1O] | ND | −14.69 |
| 111 | 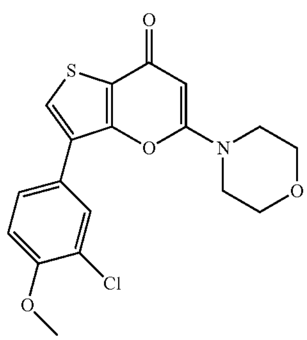 [SMILES: COc1ccc(-c2csc3c(=O)cc(N4CCOCC4)oc23)cc1Cl] | ND | −18.51 |
| 112 | 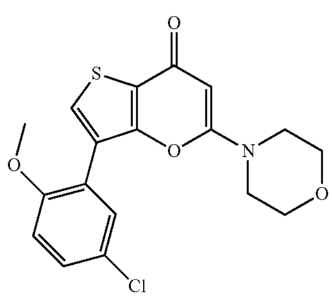 [SMILES: COc1ccc(Cl)cc1-c1csc2c(=O)cc(N3CCOCC3)oc12] | ND | −15.57 |
| 113 | 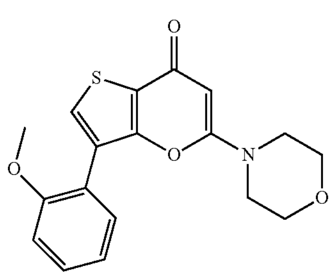 [SMILES: COc1ccccc1-c1csc2c(=O)cc(N3CCOCC3)oc12] | ND | −17.72 |

TABLE 3-continued

Structures of compounds and PC3 pAKT IC50 and BRD4 Docking Energy

| Cmpd No. | Chemical Structure | PC3 pAKT IC50 (μMolar) | BRD4 Docking Energy |
|---|---|---|---|
| 114 | 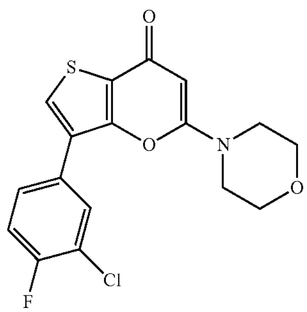 [SMILES: O=c1cc(N2CCOCC2)oc2c(-c3ccc(F)c(Cl)c3)csc12] | ND | −17.78 |
| 115 | 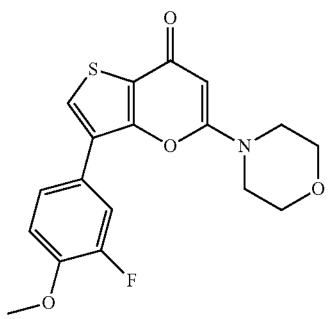 [SMILES: COc1ccc(-c2csc3c(=O)cc(N4CCOCC4)oc23)cc1F] | ND | −18.10 |
| 116 | 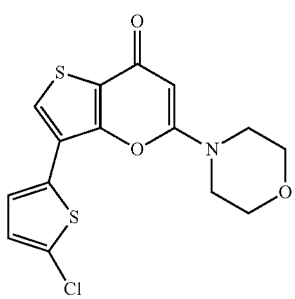 [SMILES: O=c1cc(N2CCOCC2)oc2c(-c3ccc(Cl)s3)csc12] | ND | −11.71 |
| 117 | 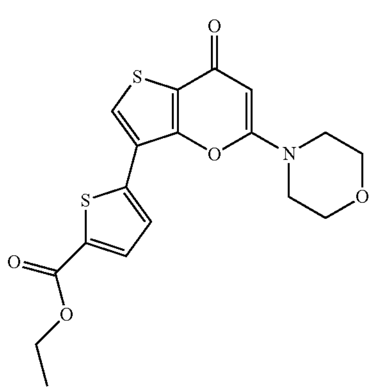 [SMILES: CCOC(=O)c1ccc(-c2csc3c(=O)cc(N4CCOCC4)oc23)s1] | ND | −14.17 |

TABLE 3-continued
Structures of compounds and PC3 pAKT IC50 and BRD4 Docking Energy
| Cmpd No. | Chemical Structure | PC3 pAKT IC50 (μMolar) | BRD4 Docking Energy |
|---|---|---|---|
| 118 | 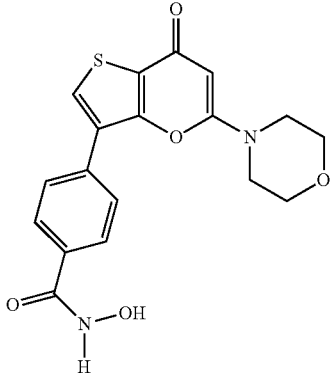 | ND | ND |
| 119 (SF1126) | 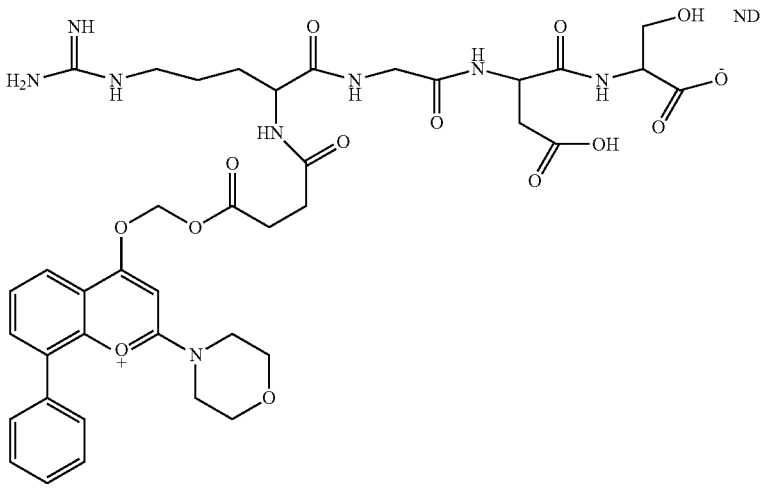 | ND | ND |
| 120 | 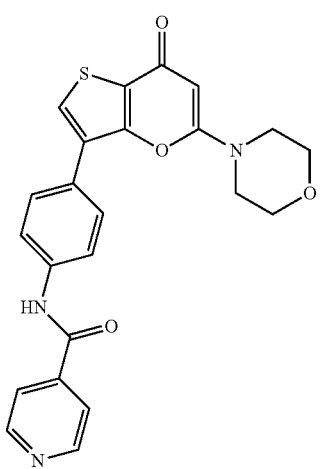 [SMILES: O=C(Nc1ccc(-c2csc3c(=O)cc(N4CCOCC4)oc23)cc1)c1ccncc1] | ND | ND |

TABLE 3-continued

Structures of compounds and PC3 pAKT IC50 and BRD4 Docking Energy

| Cmpd No. | Chemical Structure | PC3 pAKT IC50 (μMolar) | BRD4 Docking Energy |
|---|---|---|---|
| 121 | 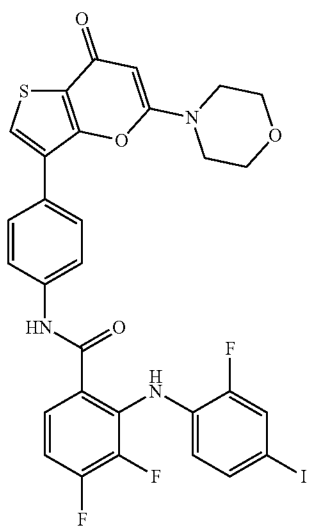 [SMILES: O=C(Nc1ccc(-c2csc3c(=O)cc(N4CCOCC4)oc23)cc1)c1ccc(F)c(F)c1Nc1ccc(I)cc1F] | ND | ND |
| 122 | 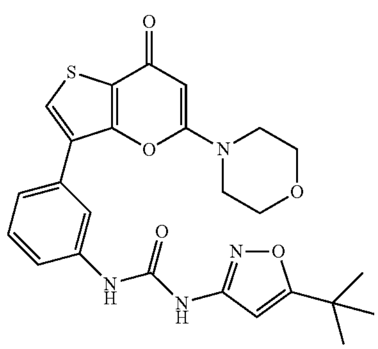 [SMILES: CC(C)(C)c1cc(NC(=O)Nc2cccc(-c3csc4c(=O)cc(N5CCOCC5)oc34)c2)no1] | ND | ND |
| 123 | 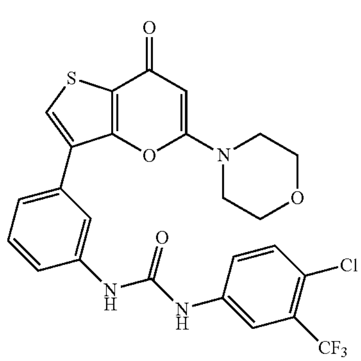 [SMILES: O=C(Nc1cccc(-c2csc3c(=O)cc(N4CCOCC4)oc23)c1)Nc1ccc(Cl)c(C(F)(F)F)c1] | ND | ND |

TABLE 3-continued

Structures of compounds and PC3 pAKT IC50 and BRD4 Docking Energy

| Cmpd No. | Chemical Structure | PC3 pAKT IC50 (μMolar) | BRD4 Docking Energy |
|---|---|---|---|
| 124 | 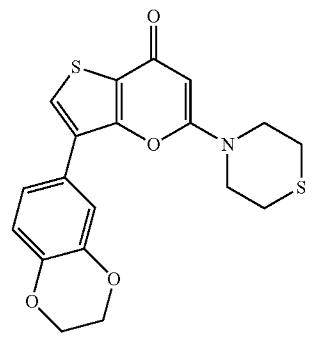 [SMILES: O=c1cc(N2CCSCC2)oc2c(-c3ccc4c(c3)OCCO4)csc12] | ND | ND |
| 125 | 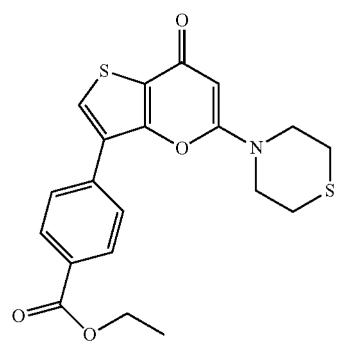 [SMILES: CCOC(=O)c1ccc(-c2csc3c(=O)cc(N4CCSCC4)oc23)cc1] | ND | ND |
| 126 | 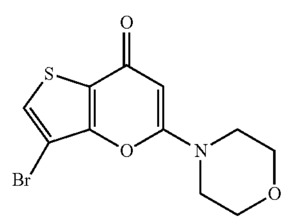 | ND | ND |
| 127 | 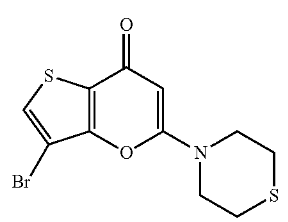 [SMILES: O=c1cc(N2CCSCC2)oc2c(Br)csc12] | ND | ND |
| 128 | 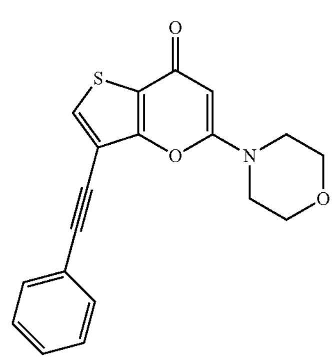 [SMILES: O=c1cc(N2CCOCC2)oc2c(C#Cc3ccccc3)csc12] | ND | ND |

TABLE 3-continued
Structures of compounds and PC3 pAKT IC50 and BRD4 Docking Energy
| Cmpd No. | Chemical Structure | PC3 pAKT IC50 (µMolar) | BRD4 Docking Energy |
|---|---|---|---|
| 129 | 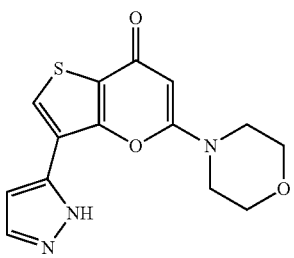 [SMILES: O=c1cc(N2CCOCC2)oc2c(-c3ccn[nH]3)csc12] | ND | ND |
| 130 | 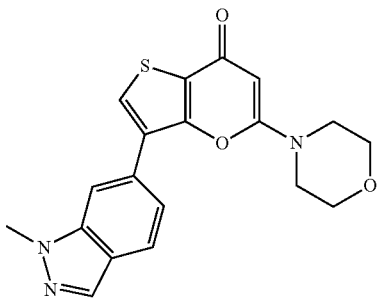 [SMILES: Cn1ncc2ccc(-c3csc4c(=O)cc(N5CCOCC5)oc34)cc21] | ND | ND |
| 131 | 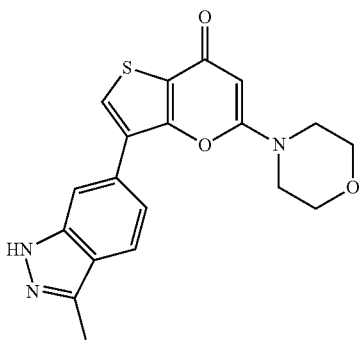 [SMILES: Cc1n[nH]c2cc(-c3csc4c(=O)cc(N5CCOCC5)oc34)ccc12] | ND | ND |
| 132 | 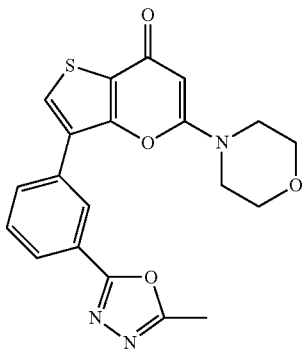 [SMILES: Cc1nnc(-c2cccc(-c3csc4c(=O)cc(N5CCOCC5)oc34)c2)o1] | ND | ND |

TABLE 3-continued

Structures of compounds and PC3 pAKT IC50 and BRD4 Docking Energy

| Cmpd No. | Chemical Structure | PC3 pAKT IC50 (μMolar) | BRD4 Docking Energy |
|---|---|---|---|
| 133 | 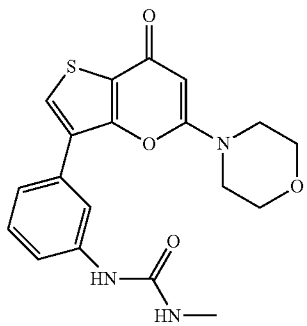 [SMILES: CNC(=O)Nc1cccc(-c2csc3c(=O)cc(N4CCOCC4)oc23)c1] | ND | ND |
| 134 | 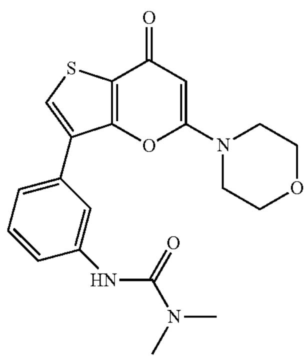 [SMILES: CN(C)C(=O)Nc1cccc(-c2csc3c(=O)cc(N4CCOCC4)oc23)c1] | ND | ND |
| 135 | 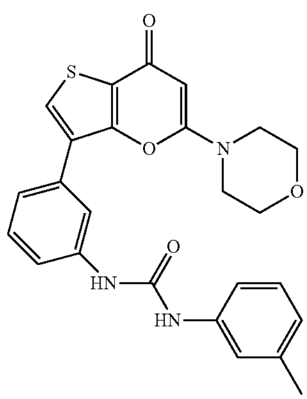 [SMILES: Cc1cccc(NC(=O)Nc2cccc(-c3csc4c(=O)cc(N5CCOCC5)oc34)c2)c1] | ND | ND |
| 136 | 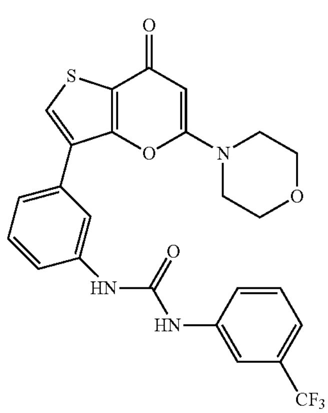 [SMILES: O=C(Nc1cccc(-c2csc3c(=O)cc(N4CCOCC4)oc23)c1)Nc1cccc(C(F)(F)F)c1] | ND | ND |

TABLE 3-continued

Structures of compounds and PC3 pAKT IC50 and BRD4 Docking Energy

| Cmpd No. | Chemical Structure | PC3 pAKT IC50 (µMolar) | BRD4 Docking Energy |
|---|---|---|---|
| 137 | 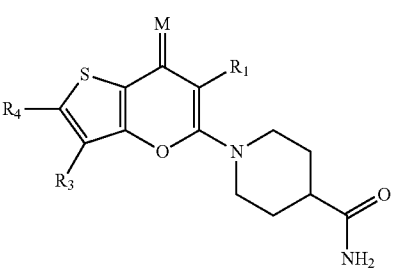 | ND | ND |

What is claimed is:

1. A method for treating a disease in a human selected from cancer, non-cancer proliferative disease, sepsis, autoimmune disease, viral infection, atherosclerosis, Type I or 2 diabetes, obesity, inflammatory disease, or Myc-dependent disorder comprising administering a compound of Formula I-IX:

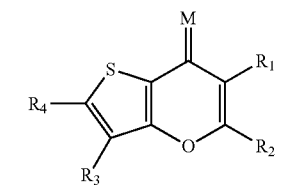

Formula I

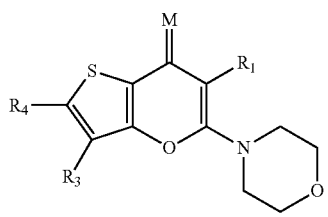

Formula II

Formula III

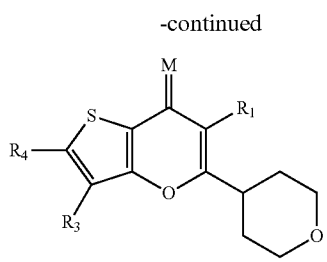

Formula IV

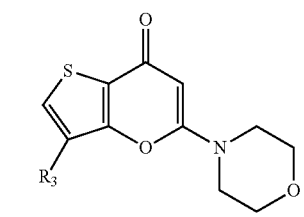

Formula V

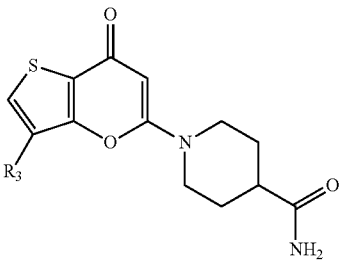

Formula VI

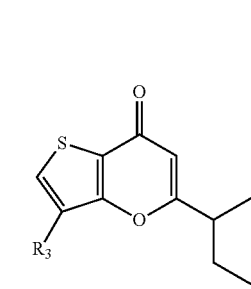

Formula VII

-continued

Formula VIII

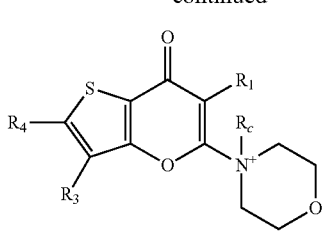

Formula IX

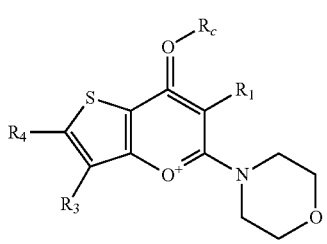

wherein M is oxygen (O) or sulfur (S);
R1 is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;
R2 is selected from R1 or

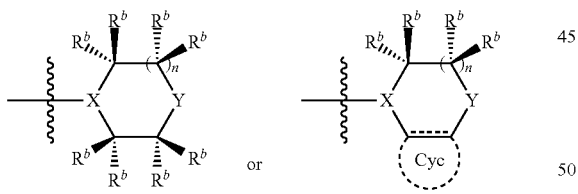

where X is C, N, P, P(O), SiR$^b$;
n is 0, 1, or 2;
Y is C—R1, O, S, NR$^a$, —C(O)(NH$_2$), —P(Z)$_m$R$^a$, SiR$^a$R$^b$, BR$^b$;
Z is O or S;
m=0 or 1;
R$^a$ is hydrogen (H) or independently at each instance any group defined in R1;
R$^b$ is hydrogen (H) or independently at each instance any group defined in R1;
R3 is selected from R1;
R4 is selected from R1; and
Cyc is an aryl, substituted aryl, heterocycle, substituted heterocycle, carbocycle, and substituted carbocycle; and wherein said cancer is selected from adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangio sarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor; and wherein said non-cancer proliferative disease is selected from meningioma, cerebri, seborrheic keratoses, stomach polyps, thyroid nodules, cystic neoplasms of the pancreas, hemangiomas, multiple endocrine neoplasia, nasal polyps, pituitary tumors, juvenile polyposis syndrome, prolactinoma, pseudotumor benign soft tissue tumors, bone tumors, brain and spinal tumors, eyelid and orbital tumors, granuloma, lipoma, vocal cord nodules, polyps, and cysts, chronic pilonidal disease, dermatofibroma, pilar cyst, pyogenic granuloma, and Castleman disease; and wherein said inflammatory disease is selected from appendicitis, pancreatitis, cholecystitis, agammaglobulinemia, psoriasis, allergy, Crohn's disease, irritable bowel syndrome, ulcerative colitis, inflammatory pelvic disease, urethritis, skin sunburn, sinusitis, pneumonitis, encephalitis, meningitis, myocarditis, nephritis, osteomyelitis, myositis, asthma, allergic rhinitis, chronic obstructive pulmonary disease, autoimmune polyglandular disease/syndrome, autoimmune alopecia, pernicious anemia, glomerulonephritis, dermatomyositis, multiple sclerosis, scleroderma, hepatitis, gastritis, enteritis, dermatitis, gingivitis, Sjogren's disease, tissue graft rejection, hyperacute rejection of transplanted organs, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus, rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Graves' disease, Guillain-Barre syndrome, Behcet's disease, scleracierma, mycosis fungoides, graft versus host disease, irritable bowel syndrome, psoriasis, acute respiratory distress syndrome and ischemia/reperfusion injury; and wherein said Myc-dependent disorder is selected from CLL, multiple myeloma, neuroblastoma, and medulloblastoma.

2. A method as in claim 1 wherein said disease is associated with aberrant PI3K and/or bromodomain protein activity and said compound is selected from

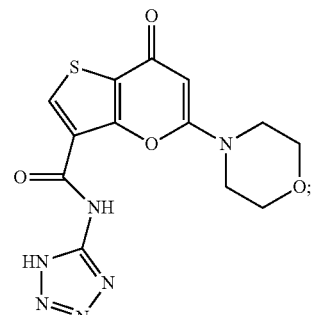

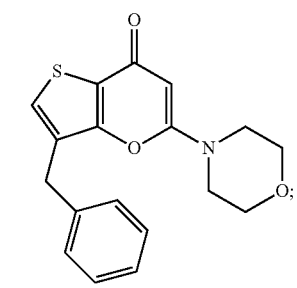

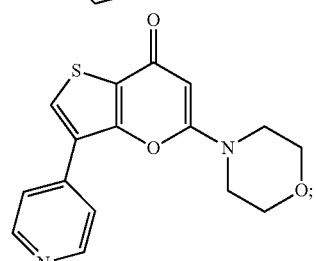

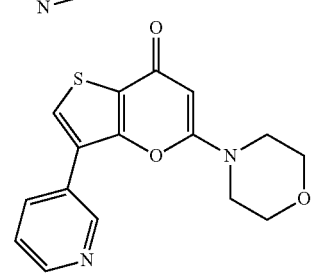

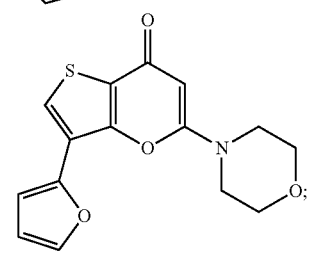

-continued
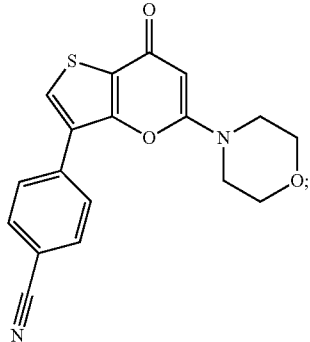
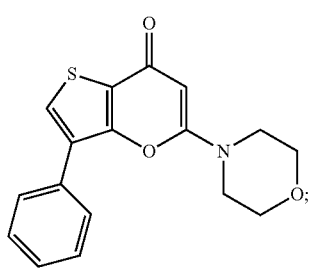
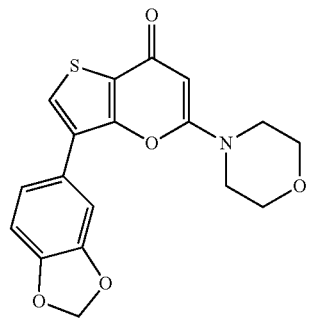
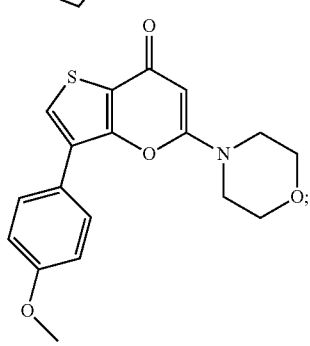
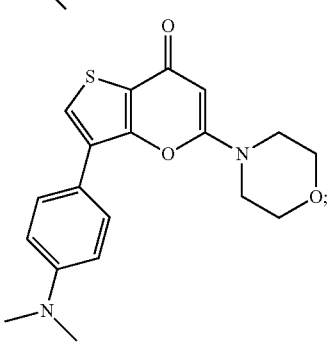
-continued
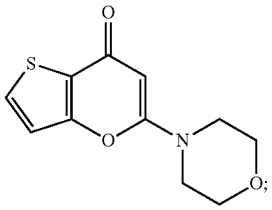
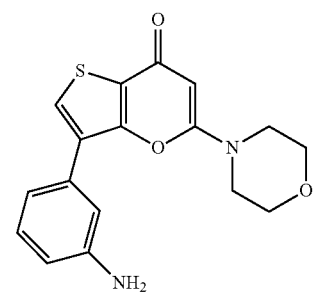
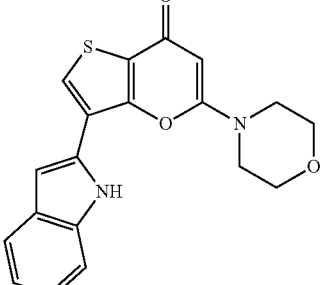
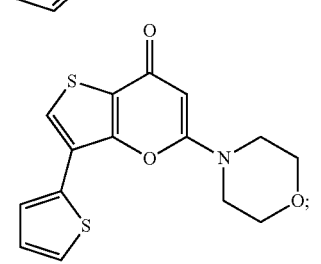
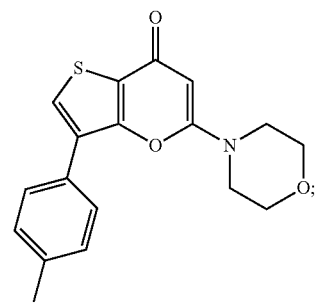
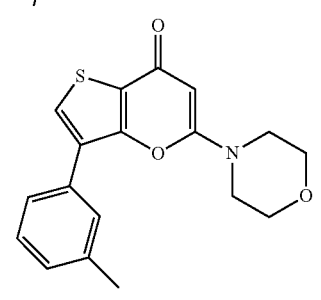

-continued
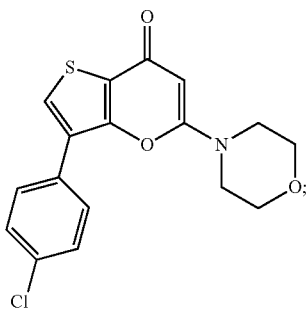
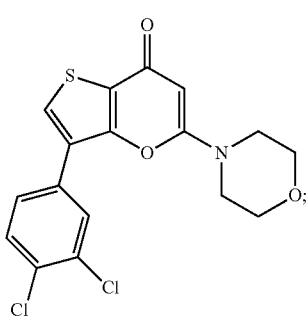
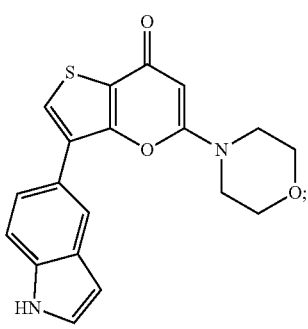
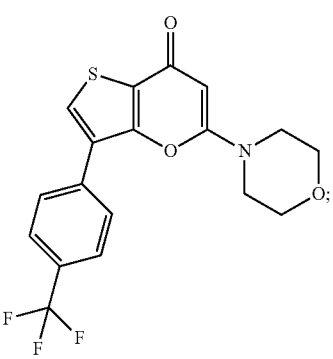
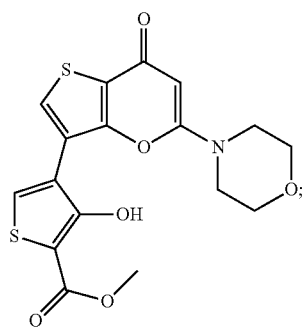
-continued
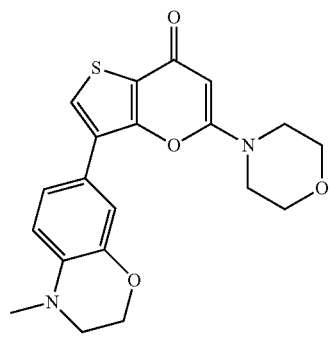
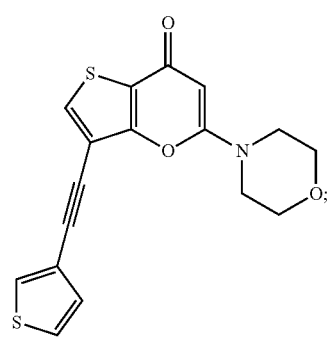
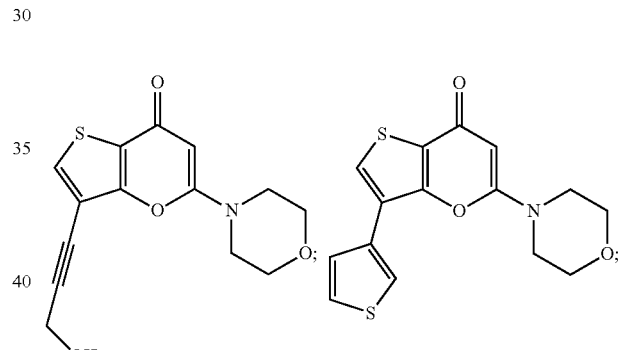
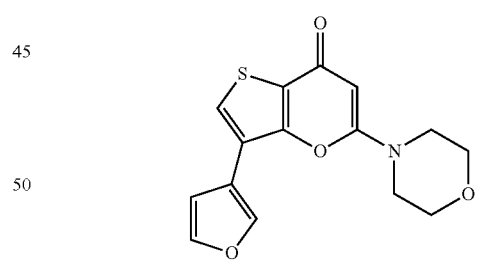
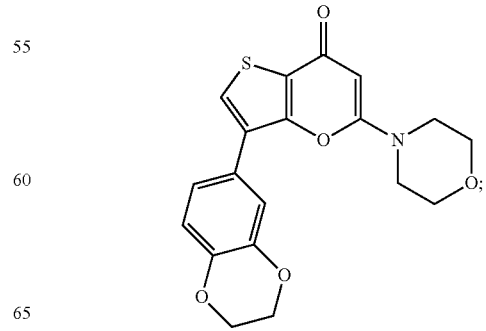

-continued
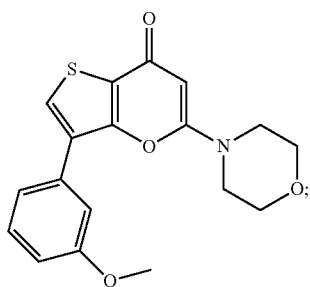
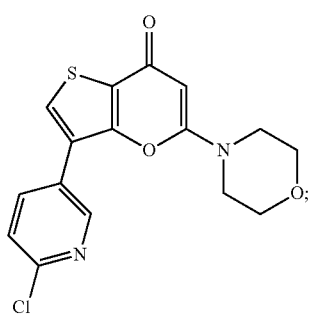
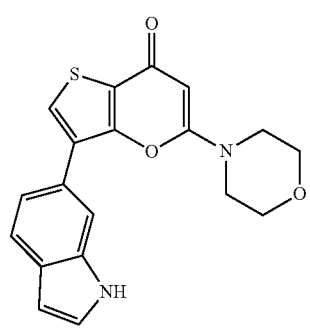
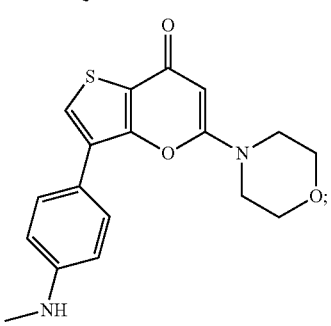
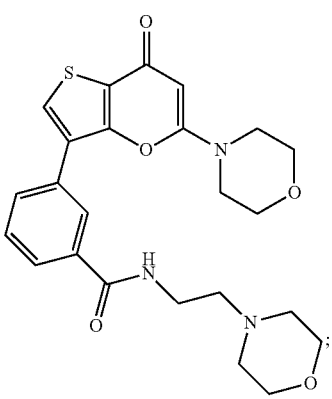
-continued
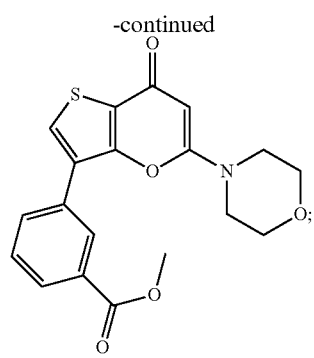
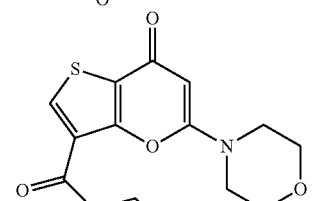
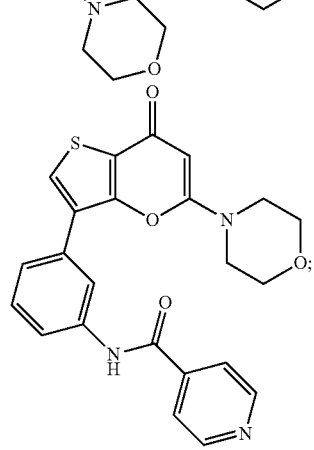
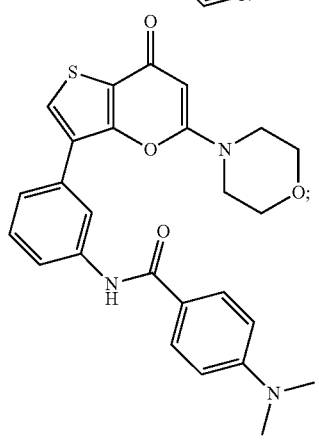
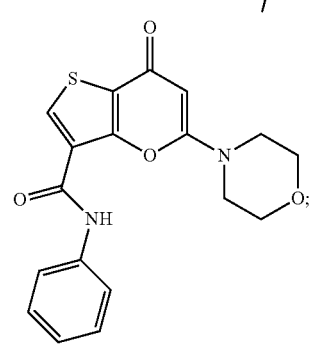

107
-continued
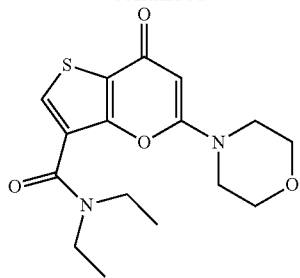
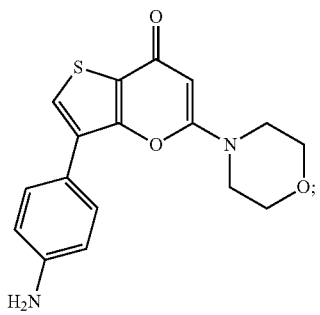
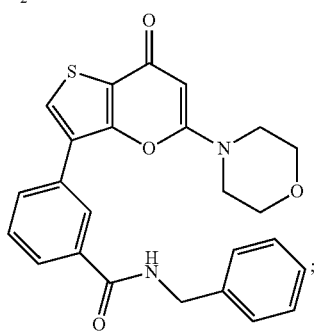
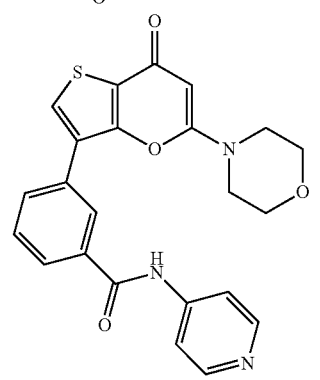
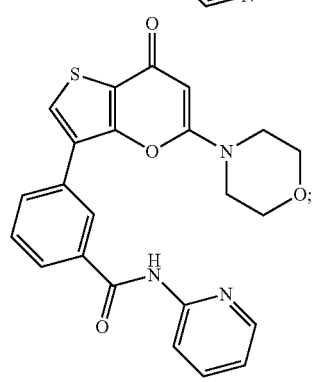
108
-continued
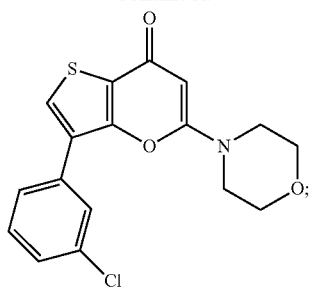
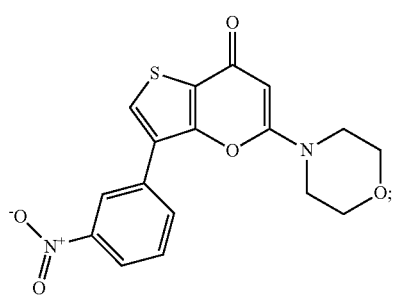
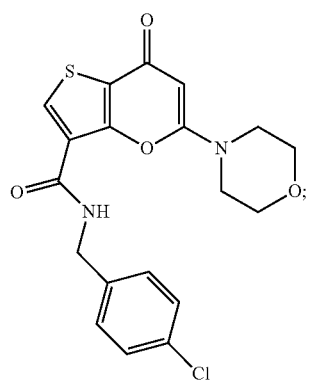
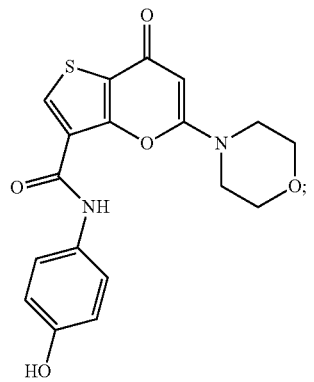

109
-continued
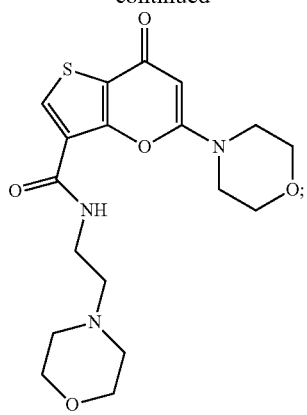
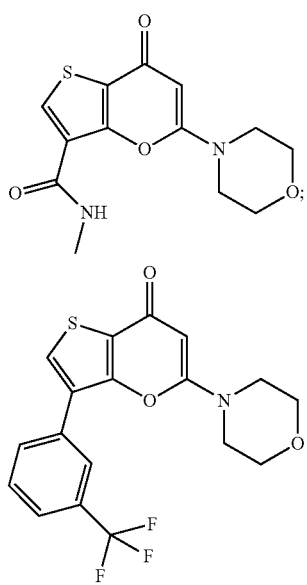
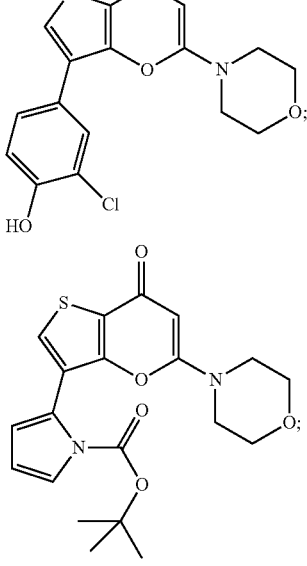
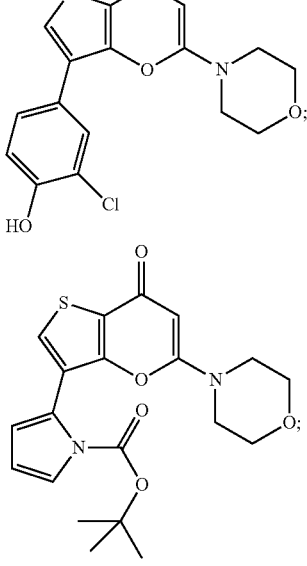
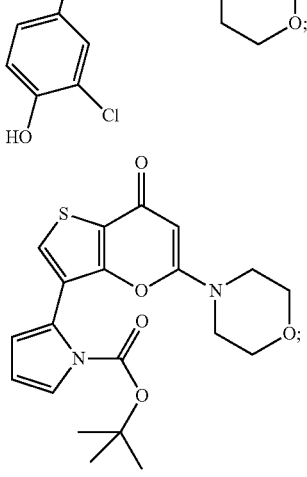
110
-continued
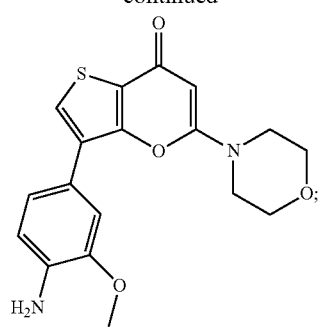
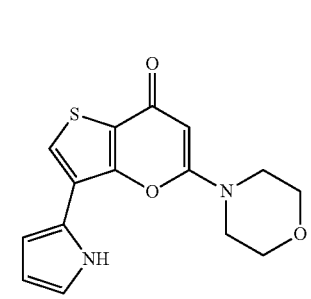
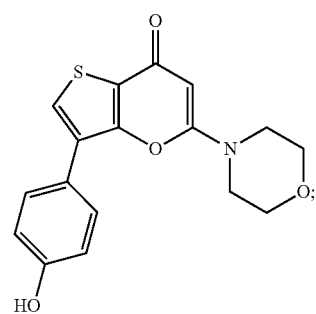
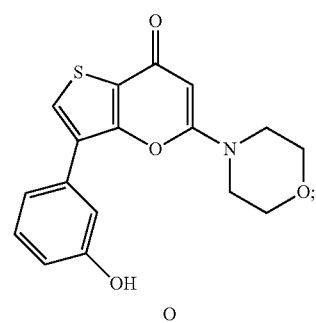
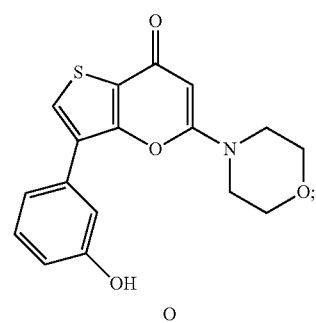

111
-continued
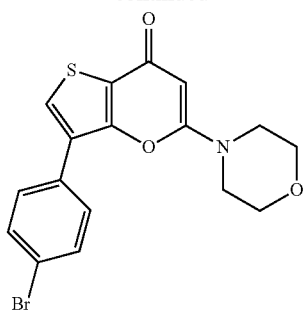
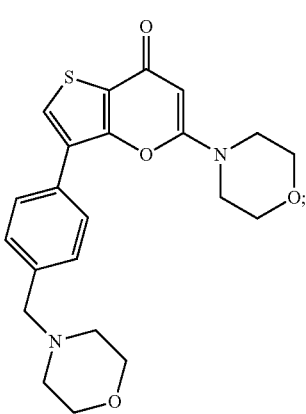
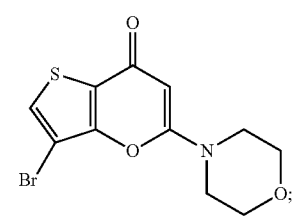
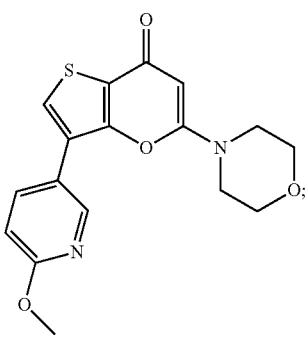
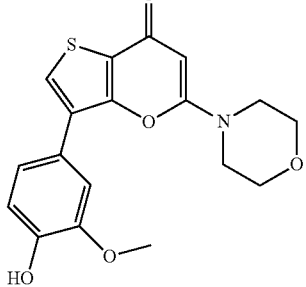
112
-continued
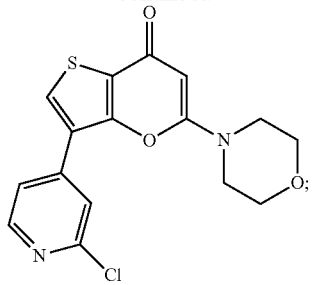
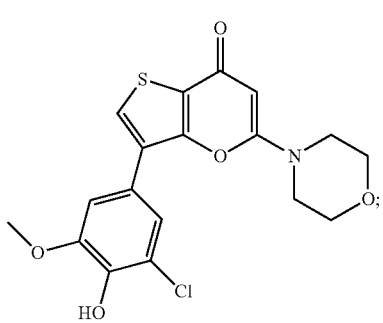
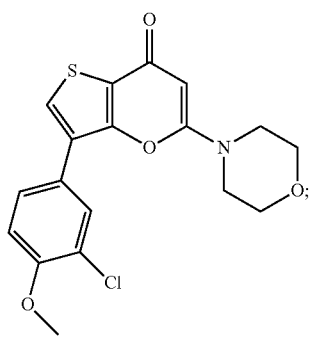
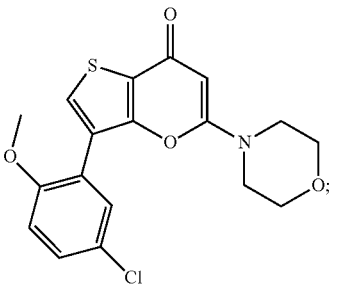
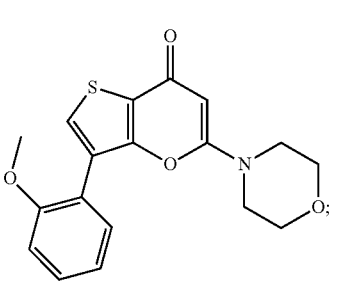

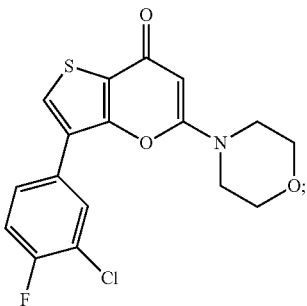
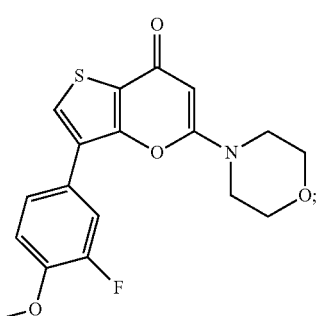
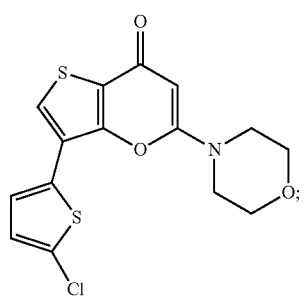
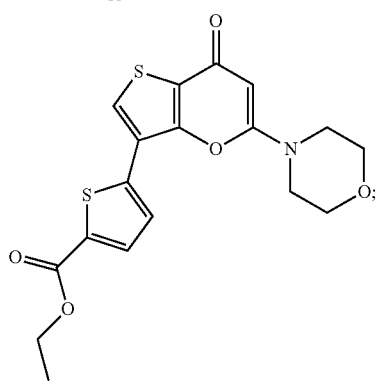
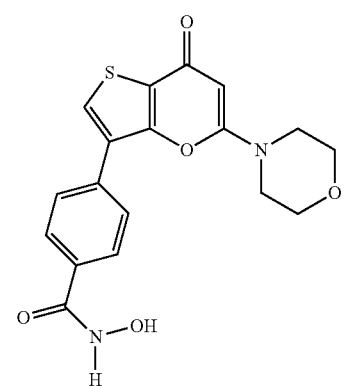
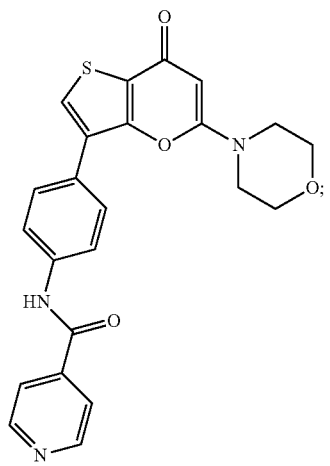
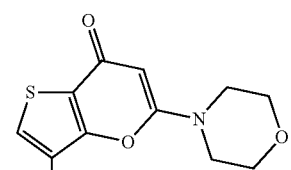
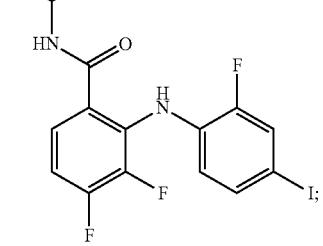
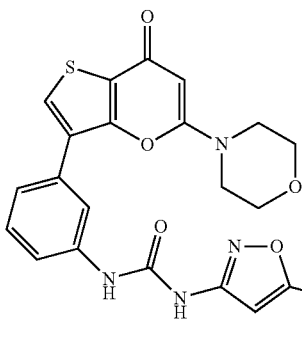
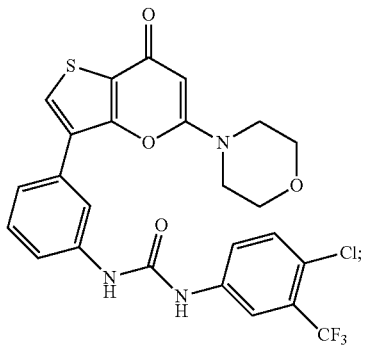

-continued
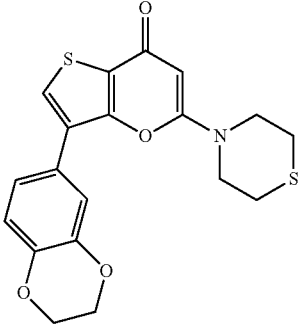
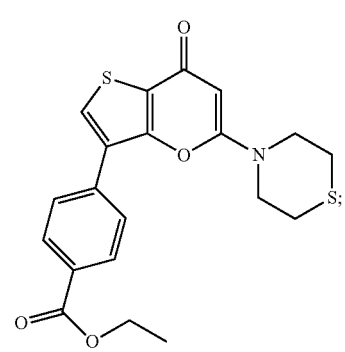
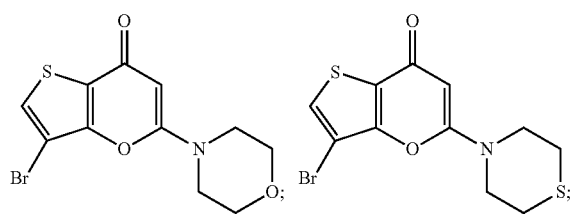
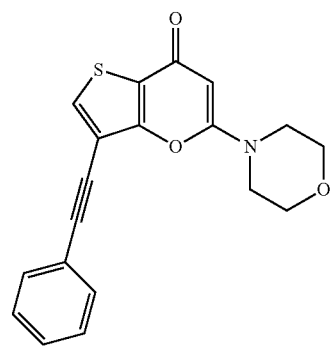
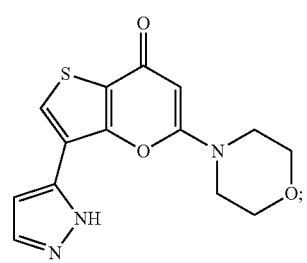
-continued
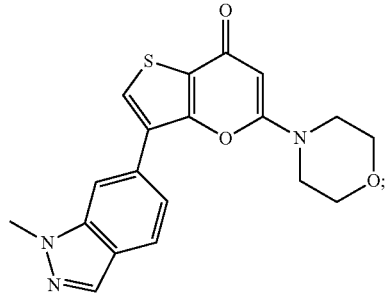
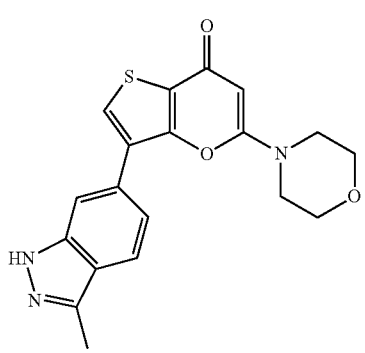
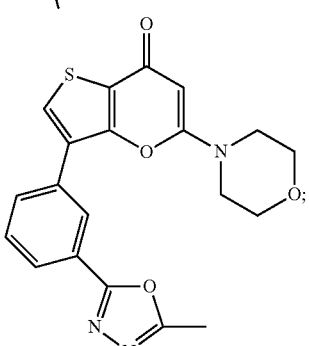
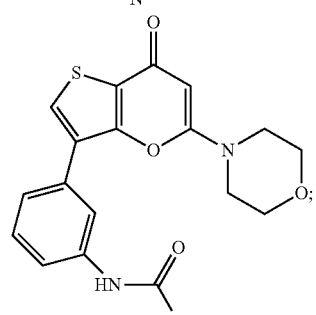
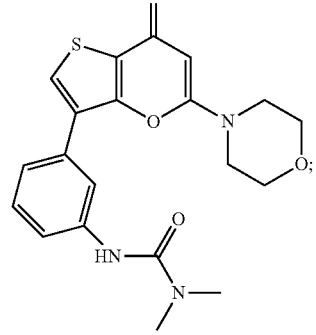

-continued
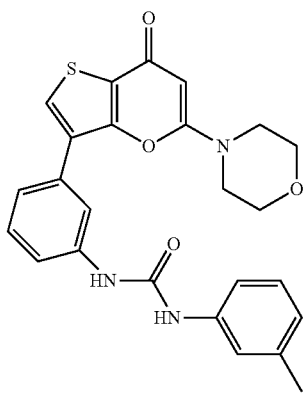
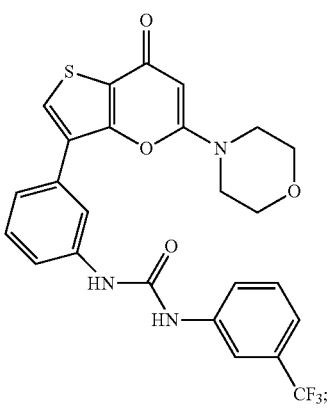
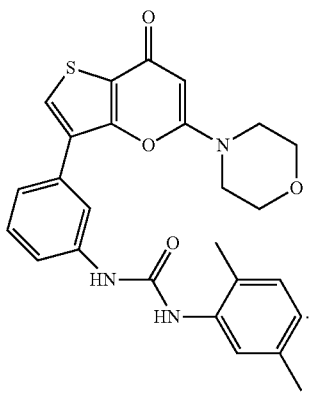
3. A method of claim 1 wherein said compound is selected from
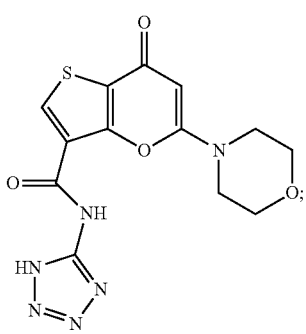
-continued
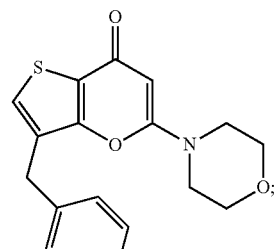
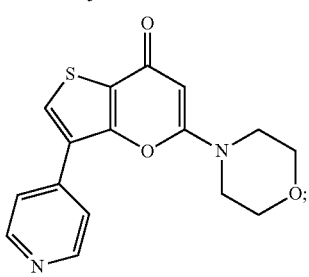
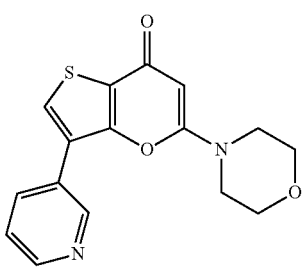
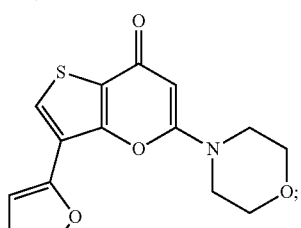
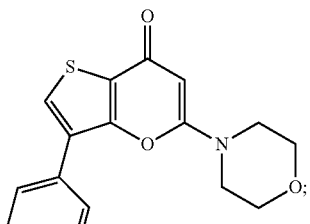
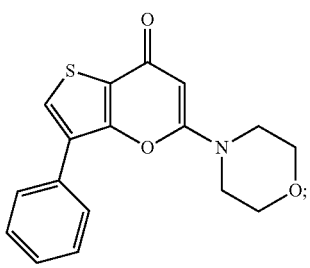

119
-continued
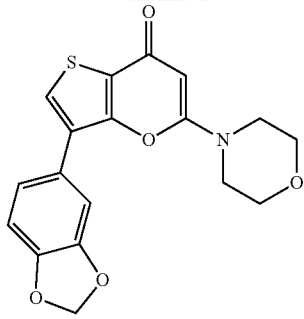
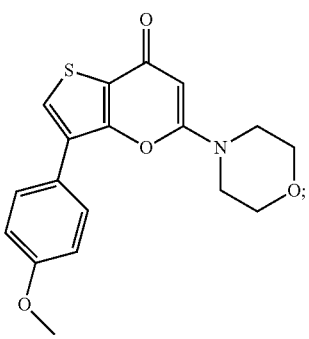
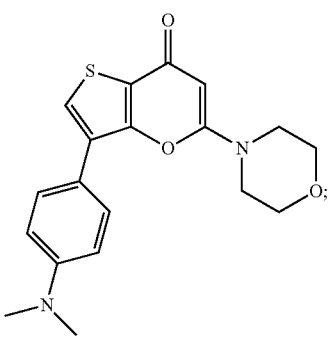
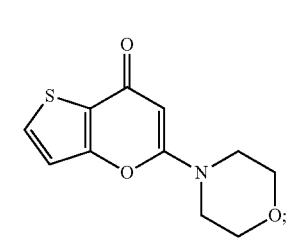
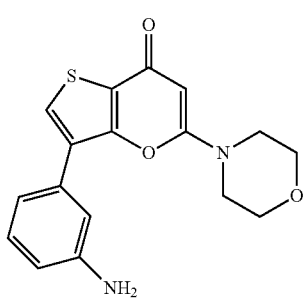
120
-continued
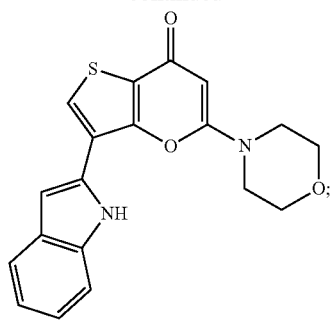
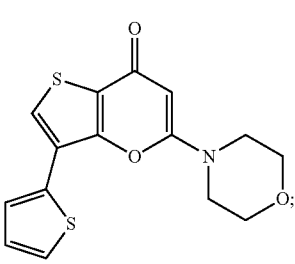
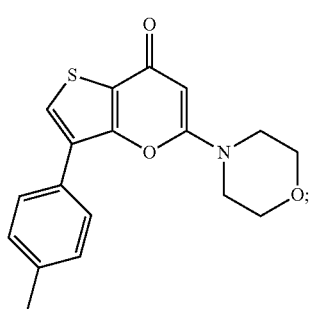
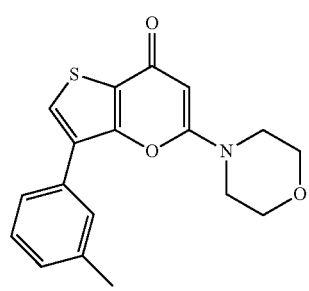
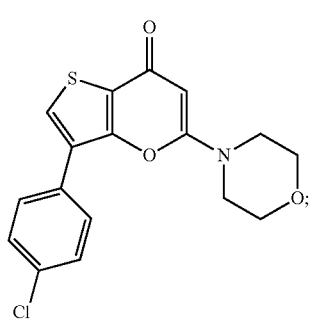

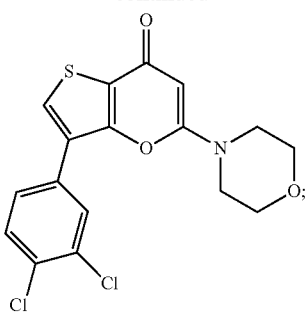
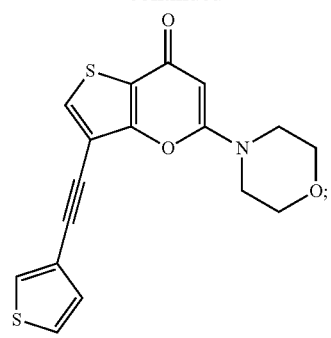
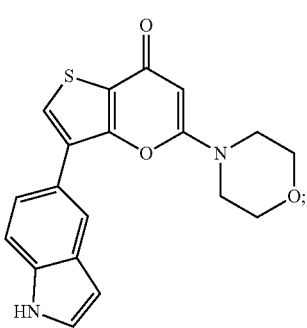
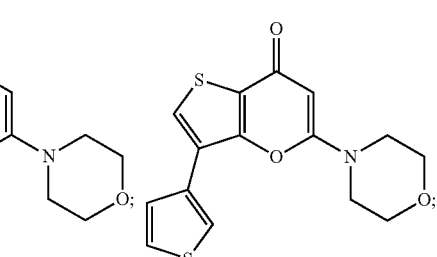
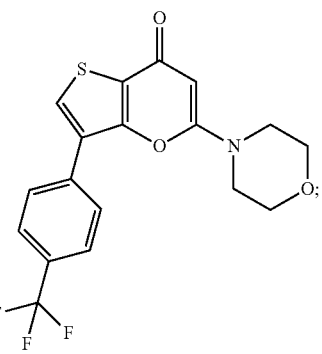
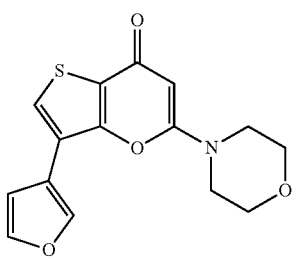
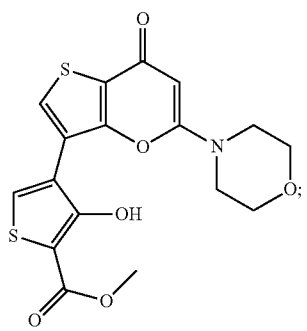
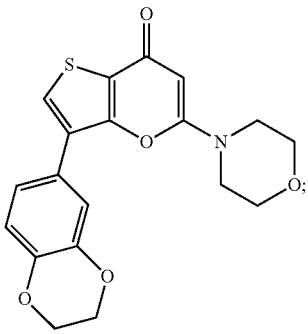
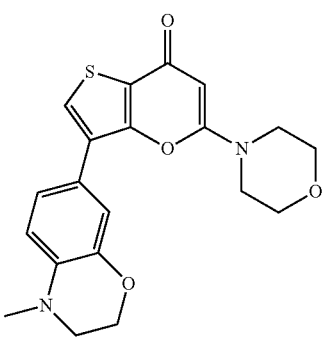
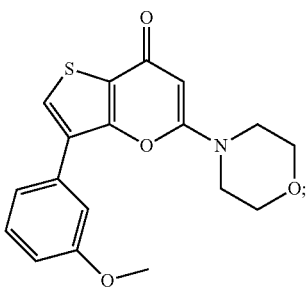

123
-continued
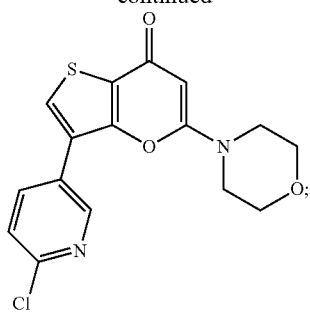
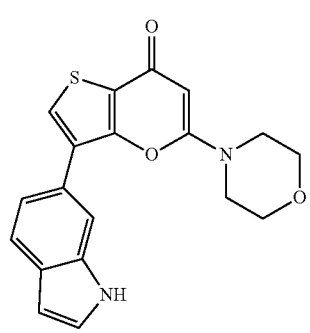
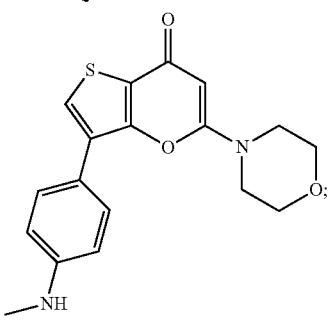
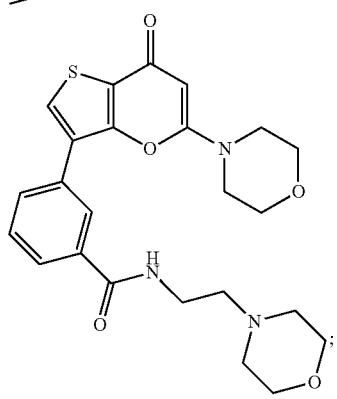
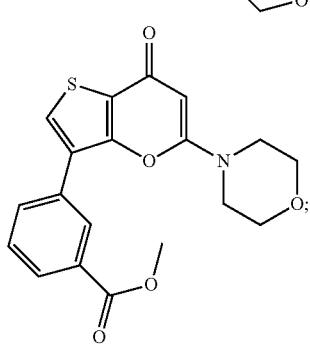
124
-continued
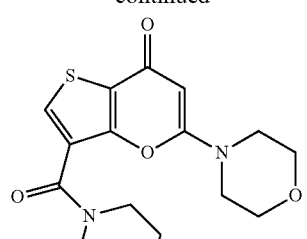
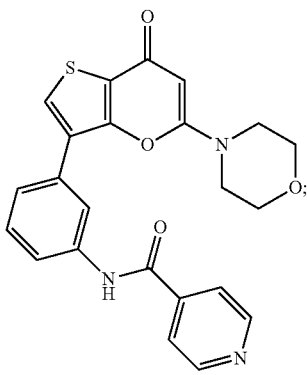
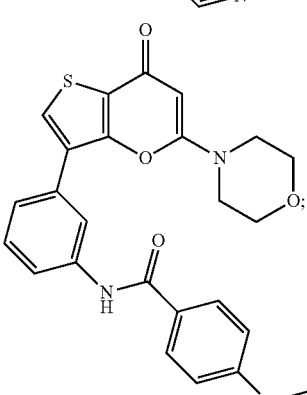
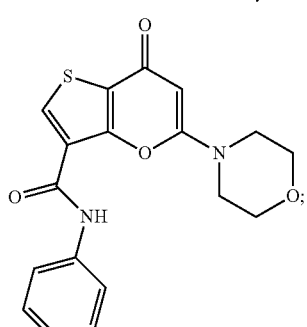
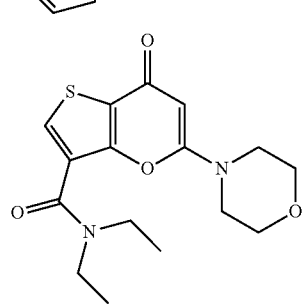

-continued
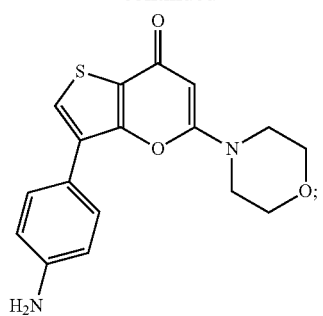
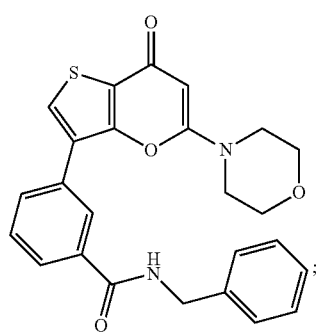
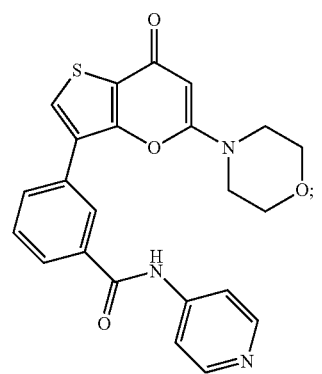
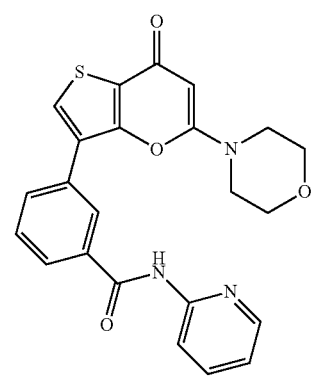
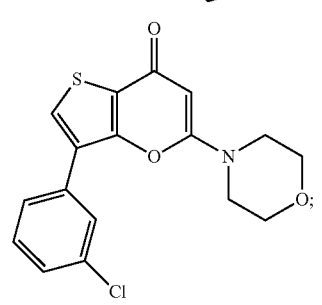
-continued
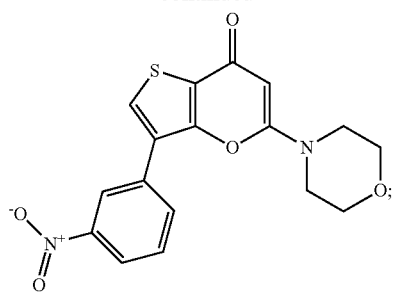
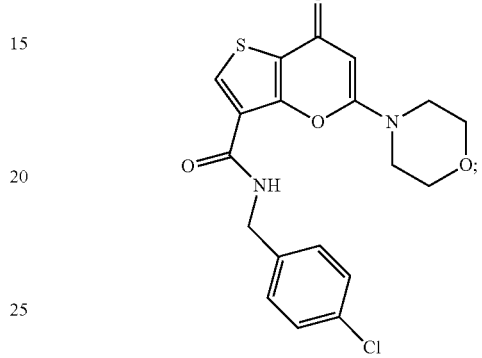
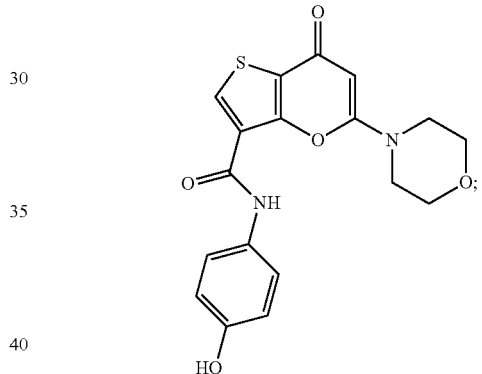
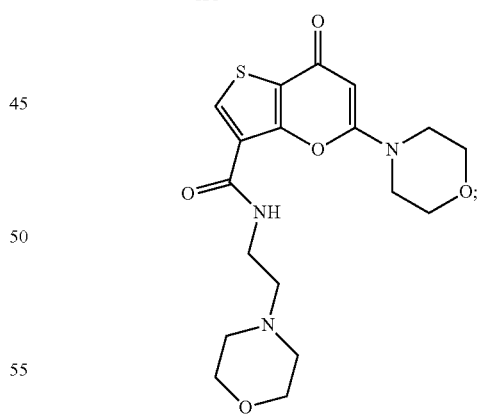
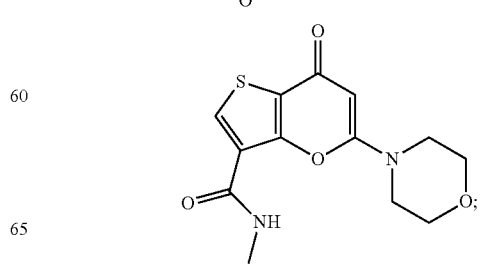

127
-continued
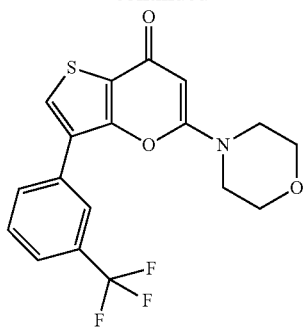
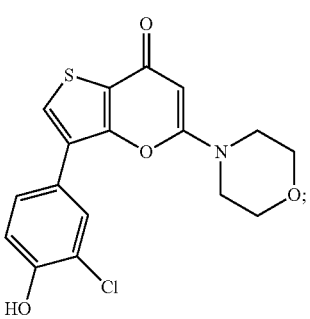
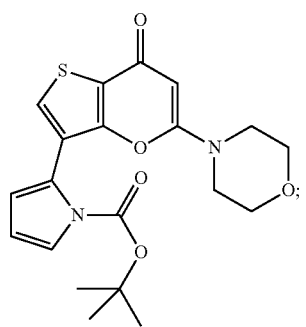
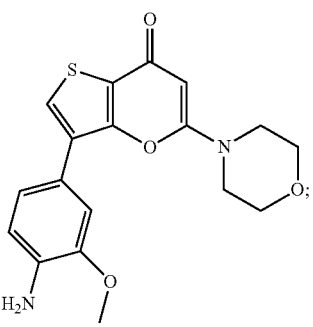
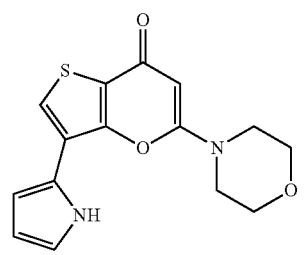
128
-continued
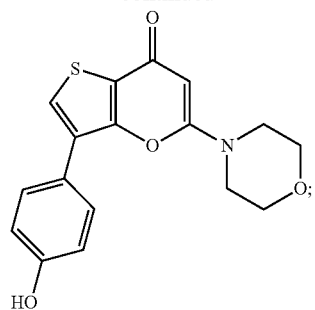
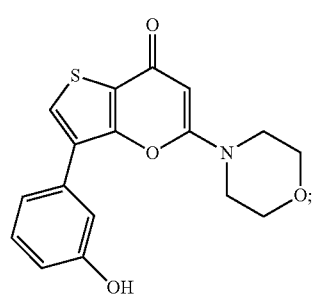
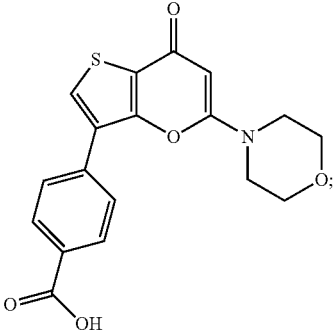
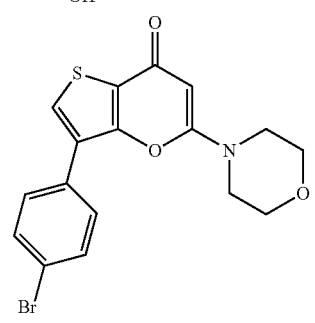
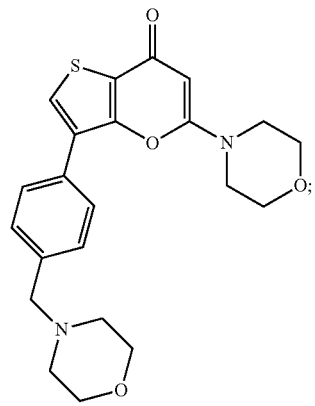

129
-continued
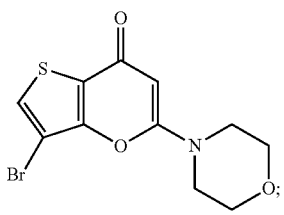
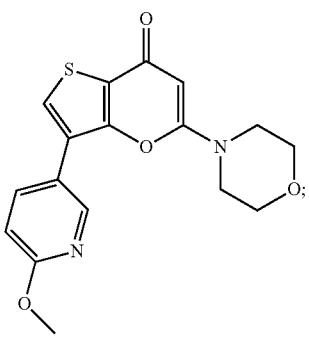
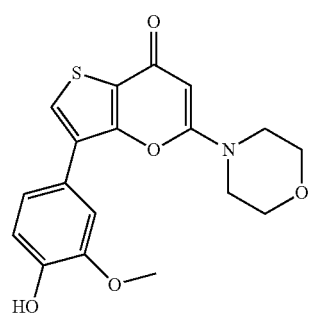
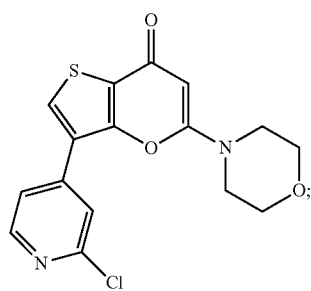
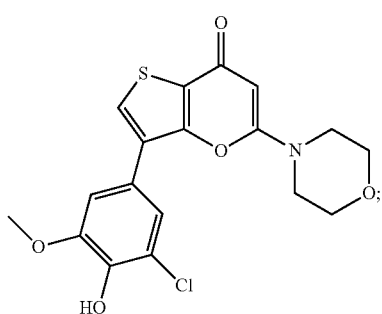
130
-continued
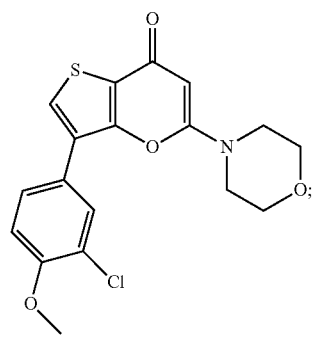
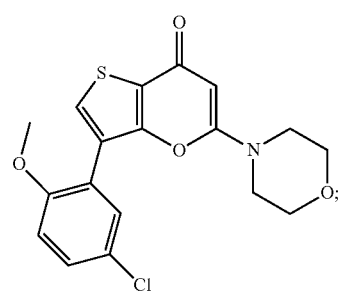
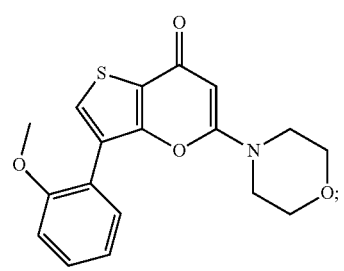
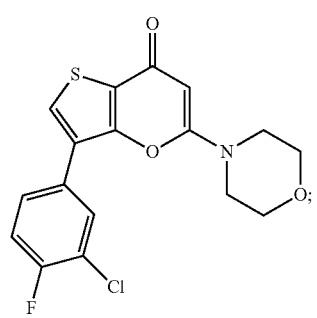
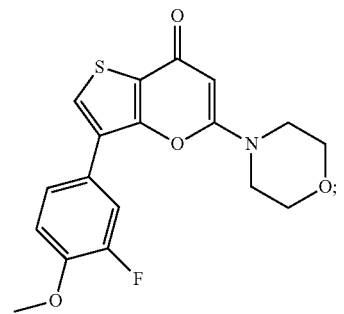

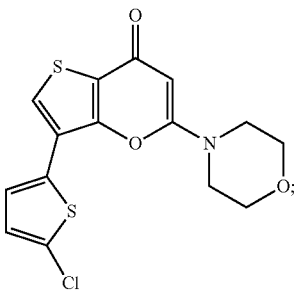
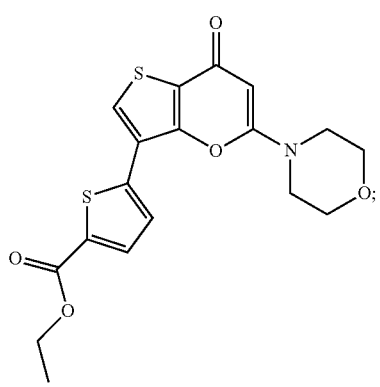
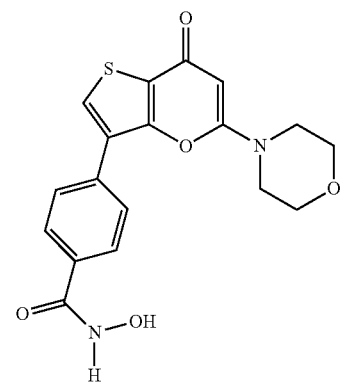
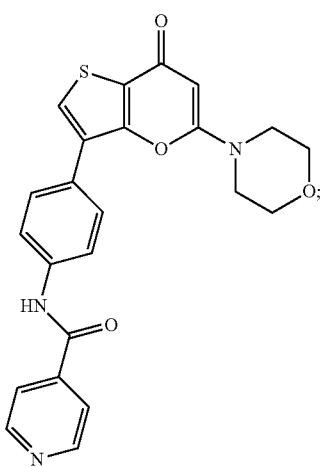
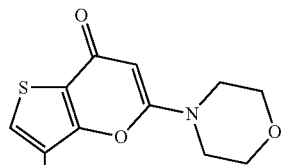
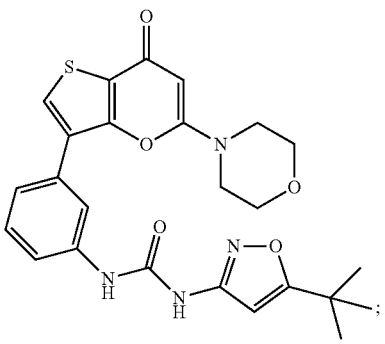
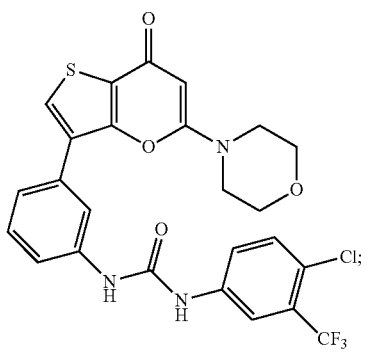
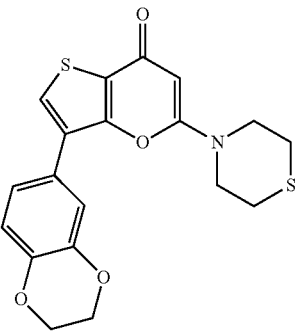

133
-continued
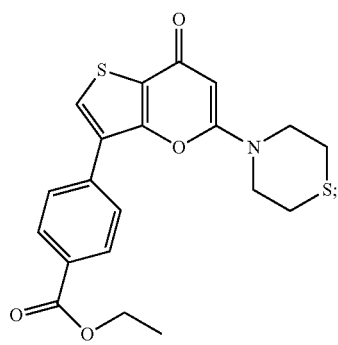
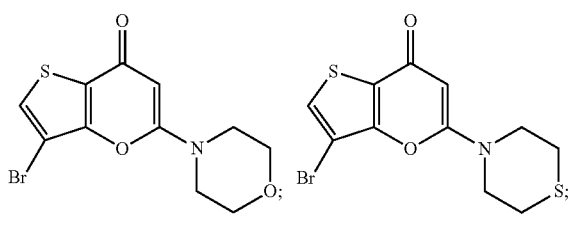
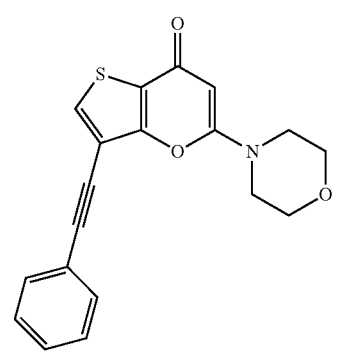
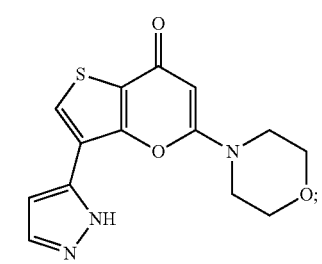
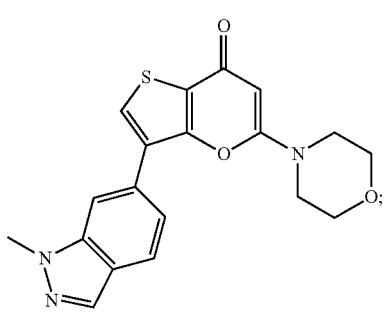
134
-continued
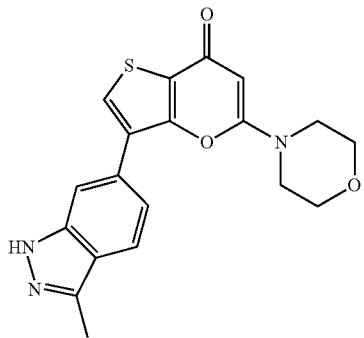
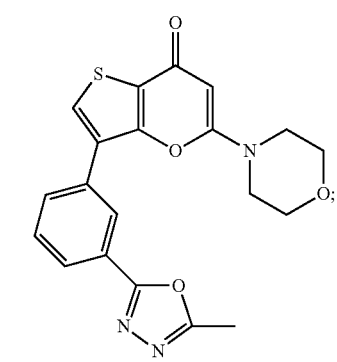
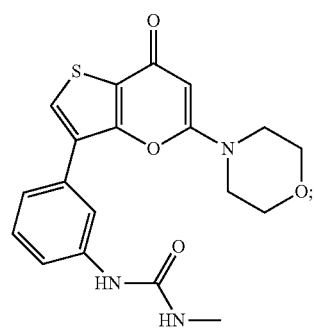
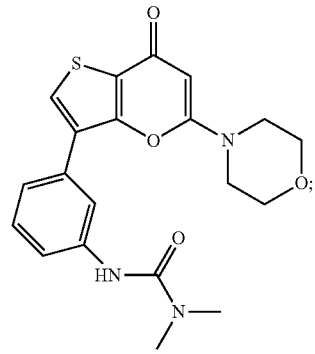

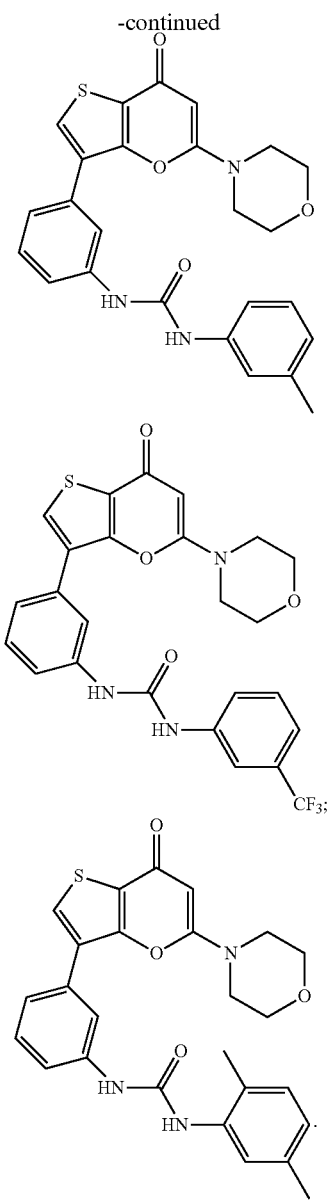

4. A method as in claim 2 wherein said disease is associated with aberrant bromodomain protein activity.

5. A method of claim 4 wherein the bromodomain protein is a BET protein.

6. A method of claim 5 wherein the BET protein is BRD4.

7. A method of claim 1 wherein said disease is cancer selected from adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangio sarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

8. A method of claim 1 wherein said disease is non-cancer proliferative disease selected from meningioma, cerebri, seborrheic keratoses, stomach polyps, thyroid nodules, cystic neoplasms of the pancreas, hemangiomas, multiple endocrine neoplasia, nasal polyps, pituitary tumors, juvenile polyposis syndrome, prolactinoma, pseudotumor benign soft tissue tumors, bone tumors, brain and spinal tumors, eyelid and orbital tumors, granuloma, lipoma, vocal cord nodules, polyps, and cysts, chronic pilonidal disease, dermatofibroma, pilar cyst, pyogenic granuloma, and Castleman disease.

9. A method of claim 1 wherein said disease is inflammatory disease selected from appendicitis, pancreatitis, cholecystitis, agammaglobulinemia, psoriasis, allergy, Crohn's disease, irritable bowel syndrome, ulcerative colitis, inflammatory pelvic disease, urethritis, skin sunburn, sinusitis, pneumonitis, encephalitis, meningitis, myocarditis, nephritis, osteomyelitis, myositis, asthma, allergic rhinitis, chronic obstructive pulmonary disease, autoimmune polyglandular disease/syndrome, autoimmune alopecia, pernicious anemia, glomerulonephritis, dermatomyositis, multiple sclerosis, scleroderma, hepatitis, gastritis, enteritis, dermatitis, gingivitis, Sjogren's disease, tissue graft rejection, hyperacute rejection of transplanted organs, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus, rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Graves' disease, Guillain-Barre syndrome, Behcet's disease, scleracierma, mycosis fungoides, graft versus host disease, irritable bowel syndrome, psoriasis, acute respiratory distress syndrome and ischemia/reperfusion injury.

10. A method of claim 1 wherein said disease is Myc-dependent disorder selected from CLL, multiple myeloma, neuroblastoma, or medulloblastoma.

11. A method of claim 1 wherein the administration of a compound of Formula I-IX is in combination with an additional anticancer agent.

\* \* \* \* \*